(12) United States Patent
Johnson et al.

(10) Patent No.: US 9,649,243 B2
(45) Date of Patent: May 16, 2017

(54) BODY LIFT-ASSIST WALKER DEVICE

(71) Applicant: Lite Run, Inc., Minneapolis, MN (US)

(72) Inventors: Douglas E. Johnson, Minneapolis, MN (US); John A. Hauck, Shoreview, MN (US); Odd Osland, Apple Valley, MN (US); Mark T. Johnson, Mounds View, MN (US); Peter M. Bobgan, Maple Grove, MN (US)

(73) Assignee: Lite Run, Inc., Minneapolis, MN (US)

( * ) Notice: Subject to any disclaimer, the term of this patent is extended or adjusted under 35 U.S.C. 154(b) by 0 days.

(21) Appl. No.: 14/884,353

(22) Filed: Oct. 15, 2015

(65) Prior Publication Data
US 2016/0166454 A1    Jun. 16, 2016

Related U.S. Application Data

(63) Continuation-in-part of application No. 13/839,204, filed on Mar. 15, 2013, now Pat. No. 9,561,149.
(Continued)

(51) Int. Cl.
*A61H 3/04* (2006.01)
*A61H 9/00* (2006.01)
(Continued)

(52) U.S. Cl.
CPC ............. *A61H 3/04* (2013.01); *A61F 5/0102* (2013.01); *A61H 3/008* (2013.01); *A61H 9/0078* (2013.01);
(Continued)

(58) Field of Classification Search
CPC ........ A61H 1/00; A61H 1/005; A61H 1/0229; A61H 1/0262; A61H 9/005; A61H 3/00;
(Continued)

(56) References Cited

U.S. PATENT DOCUMENTS 3,778,052 A * 12/1973 Andow ................... A61H 3/008
135/67
4,557,257 A * 12/1985 Fernandez ............ A61F 5/0102
602/19

(Continued)

*Primary Examiner* — Valerie L Woodward
(74) *Attorney, Agent, or Firm* — DeWitt Ross & Stevens SC

(57) ABSTRACT

The present invention provides a body lift-assist walker device for gait training is provided by the invention. The patient wears a pressurized body suit over all or a portion of his lower body, and the suit is attached to the walker device. A positive pressure or vacuum condition is applied to the interior of the suit, so that the differential pressure condition across the suit offloads a portion of the patient's body weight to the ground through the supportive walker device to make it easier for him to walk or run. The walker device also includes a lift-assisted body weight support device operated by a constant force mechanism like a pneumatic air cylinder that can lift the patient from a sitting position to a standing position with minimal physical effort. The device provides a portable and convenient system for persons undergoing physical therapy for treatment of gait or balance problems following an injury, stroke, or neurological disorder, or for use by elderly or disabled persons who have encounter difficulties in the sit-to-stand movement or walking.

43 Claims, 54 Drawing Sheets

Related U.S. Application Data which is a continuation-in-part of application No. 13/573,692, filed on Oct. 3, 2012, now Pat. No. 9,554,964, which is a continuation-in-part of application No. 12/456,196, filed on Jun. 12, 2009, now Pat. No. 8,663,133, which is a continuation-in-part of application No. 12/319,463, filed on Jan. 7, 2009, now abandoned.

(60) Provisional application No. 61/626,749, filed on Oct. 3, 2011, provisional application No. 61/010,034, filed on Jan. 7, 2008, provisional application No. 61/131,919, filed on Jun. 13, 2008.

(51) Int. Cl.

| | | |
|---|---|---|
| *A63B 21/00* | (2006.01) | |
| *A63B 69/00* | (2006.01) | |
| *A61H 3/00* | (2006.01) | |
| *A61F 5/01* | (2006.01) | |
| *A63B 71/00* | (2006.01) | |
| *A61H 1/02* | (2006.01) | |
| *A63B 22/02* | (2006.01) | |
| *A63B 22/20* | (2006.01) | |
| *A63B 22/00* | (2006.01) | |
| *A61B 5/11* | (2006.01) | |
| *A63B 21/055* | (2006.01) | |
| *A63B 21/068* | (2006.01) | |
| *A63B 23/04* | (2006.01) | |

(52) U.S. Cl.
CPC .... *A63B 21/00181* (2013.01); *A63B 69/0064* (2013.01); *A61B 5/112* (2013.01); *A61H 1/024* (2013.01); *A61H 1/0266* (2013.01); *A61H 3/00* (2013.01); *A61H 2201/163* (2013.01); *A61H 2201/165* (2013.01); *A61H 2201/1616* (2013.01); *A61H 2201/1621* (2013.01); *A61H 2201/1642* (2013.01); *A61H 2201/5071* (2013.01); *A61H 2203/03* (2013.01); *A61H 2205/08* (2013.01); *A61H 2205/10* (2013.01); *A61H 2209/00* (2013.01); *A63B 21/00069* (2013.01); *A63B 21/0552* (2013.01); *A63B 21/068* (2013.01); *A63B 21/154* (2013.01); *A63B 21/4009* (2015.10); *A63B 21/4011* (2015.10); *A63B 21/4025* (2015.10); *A63B 21/4035* (2015.10); *A63B 22/02* (2013.01); *A63B 22/20* (2013.01); *A63B 23/0405* (2013.01); *A63B 23/047* (2013.01); *A63B 23/0482* (2013.01); *A63B 69/0028* (2013.01); *A63B 71/0009* (2013.01); *A63B 71/0054* (2013.01); *A63B 2022/0094* (2013.01); *A63B 2071/0018* (2013.01); *A63B 2208/05* (2013.01); *A63B 2208/053* (2013.01); *A63B 2208/14* (2013.01); *A63B 2209/10* (2013.01); *A63B 2225/09* (2013.01); *A63B 2225/62* (2013.01)

(58) Field of Classification Search
CPC .... A61H 3/04; A61H 3/008; A61H 2201/165; A61H 2201/1652; A61H 2203/0487; A63B 21/00181; A63B 2208/05; A63B 2208/053; A63B 2208/056; A61D 3/00; B25J 9/0006; A61G 10/023; A61G 10/026

See application file for complete search history.

(56) References Cited

U.S. PATENT DOCUMENTS

| | | | | |
|---|---|---|---|---|
| 5,133,339 | A * | 7/1992 | Whalen | A61H 9/005 128/202.12 |
| 5,398,678 | A * | 3/1995 | Gamow | A61G 10/026 128/202.12 |
| 7,341,543 | B2 * | 3/2008 | Dandy | A63B 22/20 280/271 |
| 7,591,795 | B2 * | 9/2009 | Whalen | A61G 10/023 128/202.12 |
| 8,840,572 | B2 * | 9/2014 | Whalen | A61G 10/023 601/11 |
| 2002/0025889 | A1 * | 2/2002 | Egger | A61H 1/0214 482/57 |
| 2003/0032904 | A1 * | 2/2003 | Egger | A61H 36/00 601/151 |
| 2005/0070405 | A1 * | 3/2005 | Egger | A61H 9/005 482/78 |
| 2007/0054783 | A1 * | 3/2007 | Egger | A61H 1/0237 482/57 |
| 2007/0181121 | A1 * | 8/2007 | Whalen | A61G 10/023 128/202.12 |
| 2009/0014004 | A1 * | 1/2009 | Whalen | A61G 10/023 128/205.26 |
| 2009/0018571 | A1 * | 1/2009 | Whalen | A61G 10/023 606/201 |
| 2009/0082700 | A1 * | 3/2009 | Whalen | A61G 10/023 600/595 |
| 2011/0098157 | A1 * | 4/2011 | Whalen | A63B 21/00181 482/52 |
| 2011/0120567 | A1 * | 5/2011 | Kuehne | A63B 21/00181 137/14 |
| 2012/0238921 | A1 * | 9/2012 | Kuehne | A61H 1/0229 601/5 |

\* cited by examiner

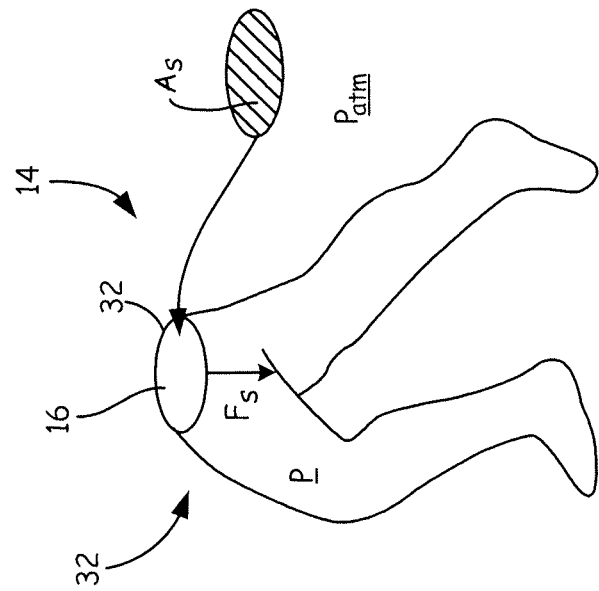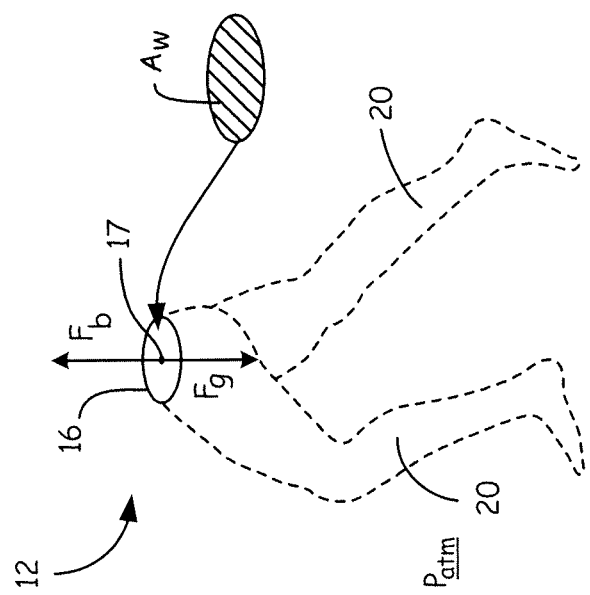
FIG. 2b
FIG. 2a

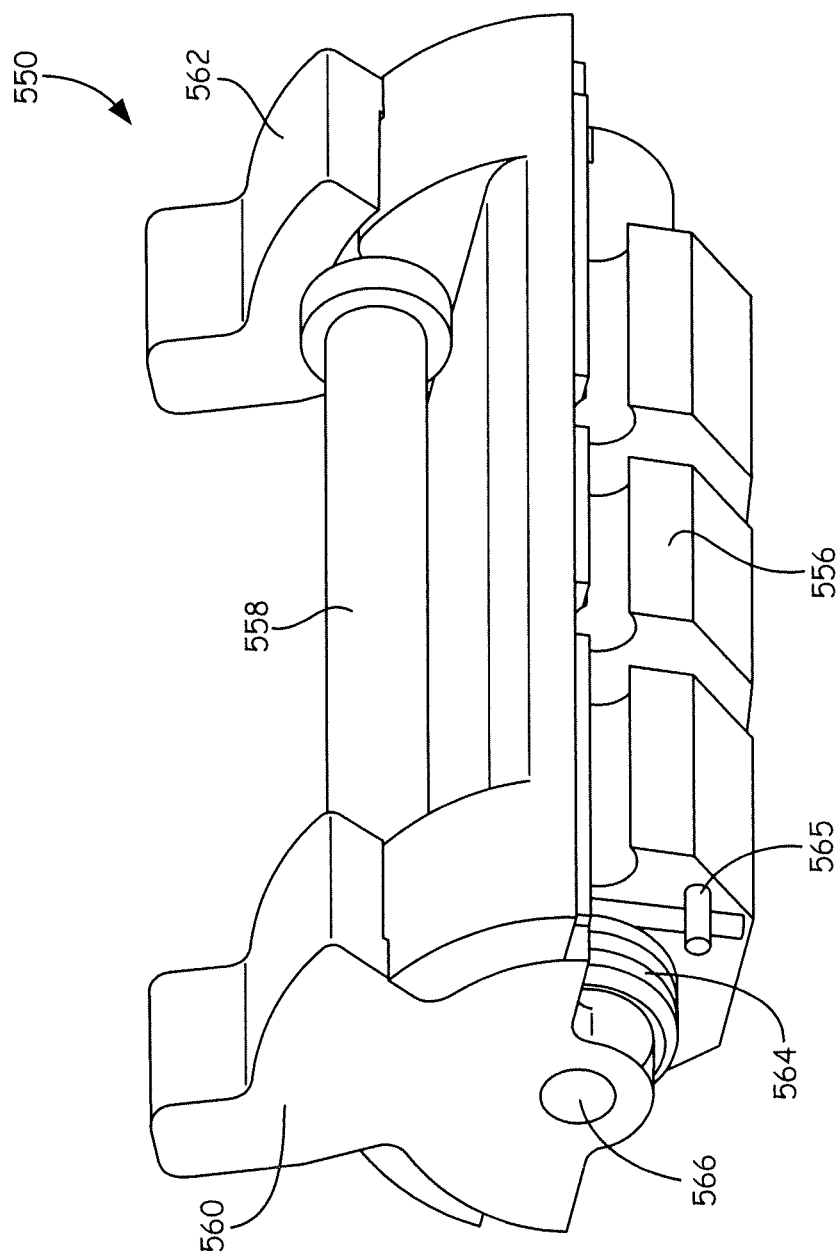

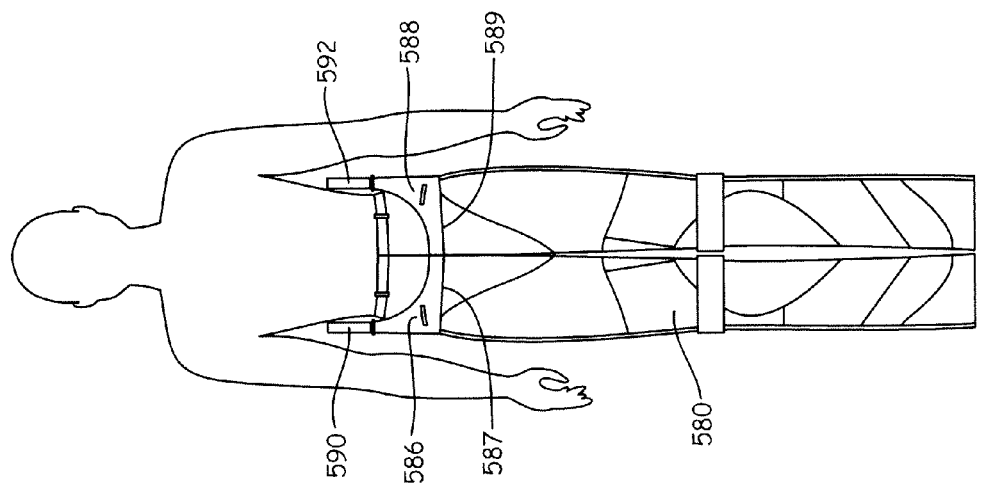
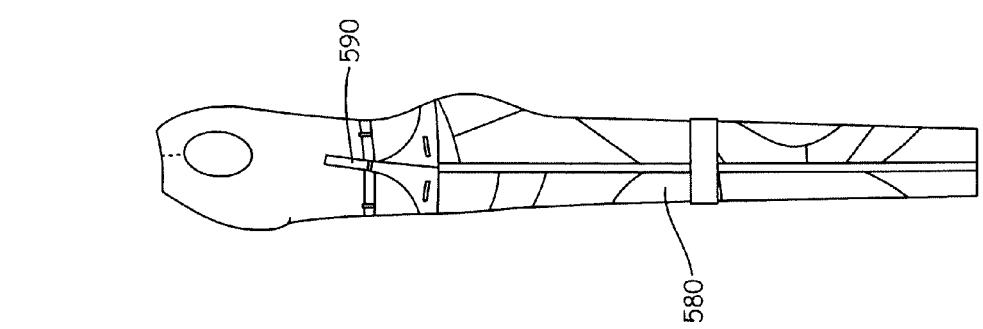
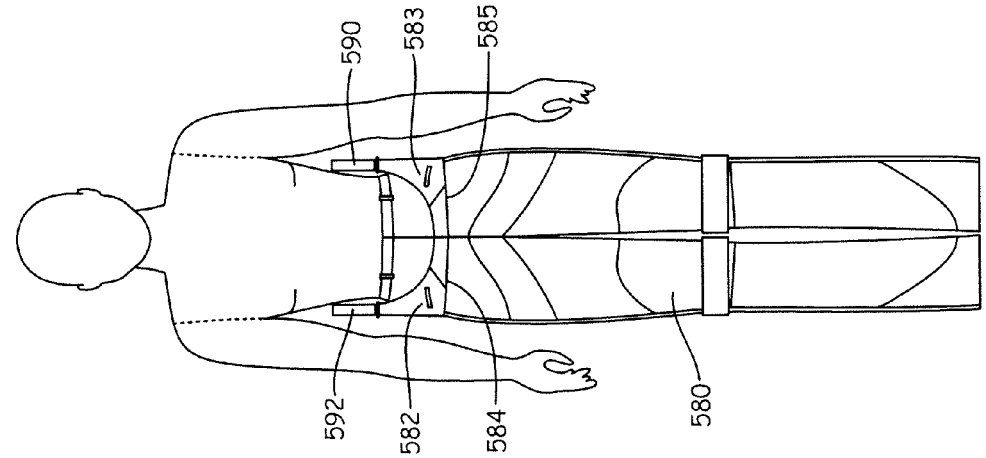

BODY LIFT-ASSIST WALKER DEVICE

CROSS-REFERENCE TO RELATED APPLICATION

This application is a continuation-in-part of U.S. Ser. No. 13/839,204 filed on Mar. 15, 2013, which claims the benefit of the U.S. provisional application No. 61/626,749 entitled "Suspension and Body Attachment System and Differential Pressure Suit for Body Support Devices" filed on Oct. 3, 2011, and is a continuation-in-part of U.S. Ser. No. 13/573, 692 filed on Oct. 3, 2012, which is a continuation-in part of U.S. Ser. No. 12/456,196 filed on Jun. 12, 2009, which is a continuation-in-part of U.S. Ser. No. 12/319,463 filed on Jan. 7, 2009, which claims the benefit of U.S. provisional application Nos. 61/010,034 filed on Jan. 7, 2008, and 61/131,919 filed on Jun. 13, 2008, all of which are hereby incorporated in their entirety by reference.

FIELD OF THE INVENTION

This invention relates generally to the motion and physical health of the mammalian body, and more specifically to portable walker devices having a lift-assist assembly for assisting humans undergoing sit-to-stand movement physical therapy or gait therapy.

BACKGROUND OF THE INVENTION

Vertebrate animals feature a flexible, bony skeletal framework that provides the body shape, protects vital organs, and enables the body to move. The human skeleton comprises approximately 206 separate bones. These bones meet at joints, the majority of which are freely movable. The skeleton also contains cartilage for elasticity, and muscular ligaments consisting of strong strips of fibrous connective tissue for holding the bones together at their joints.

The femur, fibula, tibia, and metatarsal bones of the legs and feet support the body and therefore bear its weight. Muscles associated with the ilium, pubis, ischium, patella, tarsal, and phalanges bones provide the necessary bending of the hips, knees, ankles, and toes that are essential for humans to walk, run, climb, and engage in other locomotion activities.

Likewise, the humerus, ulna and radius bones and metacarpal and phalanges bones form the arms and hands, respectively. Muscles associated with the clavicle, scapula, and carpals enable the arm to bend or flex at the shoulder or elbow, and the hand to flex at the wrist and fingers, which is useful for lifting, carrying, and manipulating objects.

Over time, body bones or joints can become damaged. Bones fracture; ligaments tear; cartilage deteriorates. Such damage may result from the aging process, manifested by arthritis, osteoporosis, and slips and falls. But injuries are also caused by sports activities. For example, recreational and competitive running is enjoyed by some 37 million Americans with 25% of them suffering from running injuries annually.

Persons recovering from such injuries often suffer from gait and balance problems that must be addressed through physical therapy. Moreover, strokes and other neurological disorders frequently cause gait and imbalance problems too. Such persons often lack the strength and balance to rise from a sitting to a standing position. Nurses, physical therapists, aids, and other care providers must assist these people first in the simple skills of standing up and then walking. The therapist begins a physical therapy session with the patient seated in a wheelchair or on a chair, bed or therapy table. The patient then must transition to a standing position and then walk using an assistive device. But, the sit-to-stand motion is rapid with the movement typically being completed in less than 2.5 seconds, as shown by kinematic studies. See Kotake T, Dohi N, Kajiware T, Sum N, Koyama Y, Miura T, "An Analysis of Sit-to-Stand Movements", 74 *Archive Physical Medicine and Rehabilitation,* 1095-99 (1993).

Gait therapy typically allows the therapist to assist with the movement of the legs and encourage patients to focus upon correcting their walking or running gait problems. Common physical therapy for such persons requires the therapist to manually manipulate the patient's legs to assist this learning process. But, physical therapists need an assistive device supporting the patient's body weight, while allowing access to the patient's legs during this gait therapy.

A number of different approaches have been taken within the industry and the medical community for treating these injuries or disorders. Exoskeletons entail external support systems made from strong materials like metal or plastic composite fibers shaped for supporting proper posture of the human body. Honda Motor Co. has employed "walking assist devices" for its automotive factory workers to support their bodyweight for reducing the load on assembly line workers' legs while they walk, move up and down stairs, and engage a semi-crouching position throughout a work shift. The U.S. military has experimented with exoskeletons for its soldiers to enable them to carry heavy equipment packs and weapons. However, the body must be connected to the exoskeleton at the limbs and other parts by means of straps and other mechanical attachment devices. The exoskeleton's motor must be regulated by various sensors and controls, and driven by hydraulics, pneumatics, springs, or other motorized mechanical systems. These can be cumbersome and expensive systems that do not necessarily reduce the stress on the body caused by gravity, and are difficult to manipulate during physical therapy or gait therapy sessions.

Athletes and older people suffering from joint injuries have rehabilitated in pools and water tanks. The buoyant property of the water provides an upwardly-directed force to the body that lightens the load otherwise directed to the joints. However, these types of systems are not portable, since the person is confined to the pool or water tank. Moreover, the resistance created by the water may interfere with physical therapy or gait therapy exercises.

Another approach is provided by a harness system exemplified by U.S. Pat. No. 6,302,828 issued to Martin et al. Consisting of an overhead frame to which is connected a raiseable body harness, such a system supports a portion of a person's body weight as he, e.g., walks or runs on a treadmill in order to diminish downward forces on the body joints. But the straps and attachment devices create localized pressure points and stresses on the body, and restrict the range of motion of the body and its limbs. Such a mechanical weight off-loading system may also lack portability. Again, such harness systems connected to stationary devices can interfere with physical therapy or gait therapy exercises.

The National Aeronautics and Space Administration ("NASA") has developed a system that utilizes differential air pressure to provide a uniform "lift" to the body to assist an exercise process. See U.S. Pat. No. 5,133,339 issued to Whalen et al. The differential pressure is applied to the lower half of the person's body that is sealed within a fixed chamber to create a force that partially counteracts the gravitational force on the body. A treadmill contained within the sealed chamber allows the person to exercise. However, this Whalen system requires a large, immobile pressure chamber containing a treadmill. Such a system is expensive and requires cumbersome entry and exit by the person, which will not accommodate physical therapy or gait therapy. The system does not allow the therapist to access and manipulate the legs of the patient to provide this gait therapy.

Various mechanical assistive devices have been developed to assist therapists with the sit-to-stand movement in physical therapy and then function as a supportive walker during the physical therapy session. Ambulatory assist devices such as walkers and rollators are used to assist elderly or physically-impaired people undergoing rehabilitation, or people suffering from gait and balance problems due to strokes, Parkinson's and other neurological disorders. These devices are used to provide balance and some measure of body weight support often by the person using their arms and hands. Use of these devices requires the disabled person raise himself from a sitting position to a standing position in order to use the device to ambulate. However, physically impaired people often lack the upper body strength or balance in order to raise themselves from a sitting to a standing position without assistance. This prevents people from independently using ambulatory assist devices. Also providing personnel for assistance entails additional costs for rehabilitation institutions or in providing home care.

Walker devices that incorporate a means for assisting a seated person to stand are commercially available or otherwise known in the art. For example, U.S. Pat. No. 6,503,176 issued to Kuntz describes a walker-like device with a sling around the user's legs for supporting all or some of the person's weight. The support sling is raised and lowered by air cylinders on the sides of the device to which compressed air from an on-board tank is delivered via valves. But, the front frame of the walker and mechanisms on the front block the patient's legs from fully extending while walking and prevent the therapist from accessing the legs from the front of the device during a physical therapy or gait therapy session. Moreover, the air cylinder lift mechanisms and other components mounted on the sides of the device prevent access by the therapist to the patient's legs. Furthermore, the width of the device is not adjustable to fit a range of patient widths and heights that would be encountered in a physical therapy setting. Additionally, the device requires use of a compressed air cylinder for power, which is inconvenient to a user due to the weight, cost and impracticality of having to transport and refill compressed air tanks.

U.S. Pat. No. 8,468,622 issued to Purwar et al. shows a lifting apparatus that includes six bar mechanism linkages operated by an electro-mechanical actuator that moves in a particular J-shaped path while the patient is lifted from a sitting position to a standing position. However, these linkages are incorporated onto the sides of the device, which restricts access by the therapist to the patient's legs to work with them during gait therapy sessions. Moreover, a system with the electric motors and linkages will not be responsive enough to provide lift to support the patient's weight during over a two-second sit-to-stand lifting motion unless the motors are extremely large and powerful. This would result in a very heavy and bulky system, requiring large motors and heavy batteries. Nor does the front of device provide necessary clearance for the patient's legs to fully extend for longer strides. The device is also not adjustable to fit the range of patients typically encountered in a physical therapy setting. A typical seated height is approximately 18 inches.

U.S. Published Application 2013/0180557 filed by Triolo et al. describes a vertical-lift walker for assisting the patient's sit-to-stand transition motion. It includes a frame assembly having upper and lower frame portions. Wheels are provided beneath the lower frame to enable the walker to be propelled and maneuvered. A supporting upper frame platform fits under the patient's arms to provide support. The lifting force is provided by gas springs, which must be first manually compressed by the patient. The patient must first be in a standing position, and then use his body weight to compress the gas spring cylinders by sitting. But patients who cannot stand without assistance will find it difficult, if not impossible, to first stand up to compress these springs. Furthermore, these gas springs mounted to the sides of the walker block access to the legs of the patient from the sides.

U.S. Pat. No. 5,569,129 issued to Seif-Naraghi et al. describes a movable device for lifting and supporting patients undergoing partial weight support gait training. The device has a U-shaped lower base which is sufficiently wide to fit around a treadmill or wheelchair. The patient wears a harness which is attached to an overhead beam that is raised and lowered by an electric motor and on-board battery. The U-shaped base is very long and wide in comparison with other assistive devices like a walker, thereby making it very hard to navigate and maneuver the device in therapy settings. Other harness-lift systems available in the market include the "New Lift Walker" sold on newliftwalker.com, and the "Lite Gait" system sold by Mobility Research, P.O. Box 3141, Tempe, Ariz. See also U.S. Pat. No. 6,302,828 issued to Martin et al. But these devices tend to be large, bulky, and cumbersome without maneuverability. While the harness systems provide some degree of body weight offloading, the patient still is required to use his upper body strength to physically lift him up from a seated position. However, many physical therapy patients lack this necessary upper body strength. Furthermore, the harness attached to the upper torso of the patient restricts the natural position of the body during running and walking to a forward leaning position, and during the sit-to-stand motion. Because harness systems pull the upper body directly upwards from the chest, they can provide too much stability for balance training. Another issue with the harness-based body weight support is that the harness supporting the subject decreases the need for natural associated postural adjustments ("APAs") that are required for independent gait. The main site for an active control of balance during gait is the step-to-step mediolateral placement of the foot. When supported by a harness during training, any mediolateral movement is restricted by a medially-directed reaction force component that will help stabilize the body in the frontal plane, and decrease or even eliminate the need for APAs, thereby making gait and balance training less effective. Moreover, the straps and attachment devices create localized pressure points and stresses on the body, and restrict the range of motion of the body and its limbs. In particular the straps around the thighs and groin interfere with the back and forth rotation of the legs.

A new alternative to a harness-based body weight support is a close-fitting differential pressure suit as described in this application and in U.S. Published Application 2010/0000547. A differential pressure body suit with external support against body suit migration is provided by the invention. In its preferred embodiment, such body suit may comprise a close-fitting, multi-layered suit sealed against a person's skin to contain the differential pressure, or a looser-fitting space suit that bends at the joints with minimal force. External support means include either fixed or movable mechanical supports attached to the body suit, extraordinary air pressure levels for making the body suit rigid, or exoskeletons attached to the body suit. This differential pressure body suit provides a portable and convenient system for rehabilitating a skeletal joint injury or training for injury prevention or athletic performance. The pressurization reduces the weight of the body to greater or lesser extents, and offloads the weight to the ground through the external support means. The body suit is flexible and has joints that can flex with minimal force even under pressure.

Pressurized bodysuits have also been used within the industry for several different applications. For example, U.S. Published Application 2002/0116741 filed by Young discloses a bodysuit with integral supports and internal air bladders that are filled with pressurized air. This air pressure exerts force against the muscles of a person wearing the suit to tone them during daily activities. U.S. Pat. No. 6,460,195 issued to Wang illustrates exercise shorts with buckled belts, air bags, and a vibrator that directs pulses of pressurized air to the body to work off fat and lift the hips. U.S. Pat. No. 3,589,366 issued to Feather teaches exercise pants from which air is evacuated, so that the pants cling to the body of an exerciser to cause sweating, thereby leading to weight loss.

The U.S. military has also employed pressurized suits of various designs for protecting fighter pilots from debilitating external G-forces. Due to rapid changes in speed and direction, the fighter pilot's body undergoes very high accelerations. This normally forces the pilot's oxygen-laden blood away from the portion of the circulatory system between the heart, lungs and brain, pooling instead toward the blood vessels of the lower extremities. As a result, the pilot can lose situational awareness and spatial orientation. A pilot's bodysuit pressurized against the blood vessels of the legs can force the oxygen-laden blood back to the head and torso of the pilot. See U.S. Pat. No. 2,762,047 issued to Flagg et al.; U.S. Pat. No. 5,537,686 issued to Krutz, Jr. et al.; and U.S. Pat. No. 6,757,916 issued to Mah et al. U.S. Pat. No. 5,997,465 issued to Savage et al. discloses a pants bodysuit made from metal or polymer "memory material" that is heated by electrical current to form around the body, and then cooled to apply pressure for treating this G-forces phenomenon.

Pressurized bodysuits have been used previously for other purposes, such as splinting leg fractures, stopping bleeding from wounds, treating shock, and supporting the posture of partially paralyzed patients. See, e.g., U.S. Pat. No. 3,823,711 issued to Hatton; U.S. Pat. No. 3,823,712 issued to Morel; U.S. Pat. No. 4,039,039 issued to Gottfried; and U.S. Pat. No. 5,478,310 issue to Dyson-Cartwell et al. Bodysuits can also have air between the suit and the body evacuated by vacuum to draw the suit into close contact with the body. See U.S. Pat. No. 4,230,114 issued to Feather; U.S. Pat. No. 4,421,109 issued to Thornton; and U.S. Pat. No. 4,959,047 issued to Tripp, Jr. See also U.S. Published Application 2006/0135889 filed by Egli.

But, such pressurized body suits have not previously been used to rehabilitate skeletal joint injuries. Moreover, they have typically been used only in stationary situations like a sitting pilot due to the problem of air pressure forcing the body suit off the lower torso. In some applications like weight-loss patients, suspender straps have been required to overcome this downwards migration of the bodysuit pants.

In either harness-based or partial pressure differential pressure suit approaches, means are required for attaching the harness, pressure suit or other attaching means to the mechanism that provides the counter-force body weight support. Harness systems use ropes straps and or cables to attach the harness system to the overhead counter-weight system. A natural walking or running gait consists of body movements or rotations about various axes of the body. It is important that the connecting system not unduly restrict these movements. There is a need for body weight support systems that do not restrict natural body movements.

Thus there is a need for a walker device that can provide body weight offloading and lift support throughout the range of the sit-to-stand movement. Once standing, the patient then should be able to walk with the supportive walker device while undergoing gait therapy by the therapist. A pressurized bodysuit that can worn by the patient to apply localized differential pressure to a lower body part, coupled with the walker external support and a pressure condition control system would be beneficial, particularly due to its portable nature. The walker device also should be easily maneuverable by the therapist or patient during the walking portion of gait therapy.

SUMMARY OF THE INVENTION

The present invention provides a body lift-assist walker device for gait training. It comprises a frame with wheels that a patient can lean on while walking. The patient wears a pressurized body suit over all or a portion of his lower body, and the suit is attached to the walker device. In its preferred embodiment, the body suit may comprise a close-fitting, multi-layered suit sealed against the patient's skin to contain the differential pressure, or a looser-fitting space suit that bends at the mammal's joints with minimal force. A positive pressure or vacuum condition is applied to the interior of the suit, so that the differential pressure condition across the suit offloads a portion of the patient's body weight to the ground through the supportive walker device to make it easier for him to walk. At the same time, the walker device acts against body suit migration that is caused along the patient's lower body by the differential pressure condition. Alternatively, the patient may be fitted with a harness system operatively attached to the walker device for offloading a portion of his body weight.

The body suit is attached to the walker device by means of a suitable attachment means that provides sufficient freedom of movement by the patient as he uses the walker, and is reasonably easy to attach and detach. Examples of this attachment means includes a rigid waist band incorporated into the body suit, a cord and pulley system interposed between the waist band and the walker device, or an attachment latch mechanism built into the walker device which cooperates with a latch pin incorporated into webbing extending from the body suit.

The walker device also includes a lift-assisted body weight support device operated by a constant force mechanism like a pneumatic air cylinder that can lift the patient from a seated position on all types of sitting furniture including wheelchairs, chairs, beds, or raised therapy platforms to a standing position. A lift mechanism incorporated into the walker device uses a belt and series of cooperating rollers that raises and lowers lift arms on the walker device to which the body suit is attached in response to the position of the air cylinder. The upwards force delivered to the body suit by this lift mechanism in combination with the offloaded body weight created by the body suit or harness system enables the patient to undergo this sit-to-lift motion with very little physical effort.

This body lift-assist walker device provides a portable and convenient system for persons undergoing physical therapy for treatment of gait or balance problems following an injury, stroke, or neurological disorder, or for use by elderly or disabled persons who encounter difficulties in the sit-to-stand movement. The walker device is easily adjustable by the therapist to fit patients of all sizes and allows full access to the patient's legs during gait training. It is easy to maneuver by the patient or therapist.

BRIEF DESCRIPTION OF THE DRAWINGS

In the accompanying drawings:

FIG. 2a is a schematic view of the legs and feet of a human the forces applied thereto.

FIG. 2b is a schematic view of the pressurized body suit and the forces applied thereto.

FIG. 47 is a perspective view of the attachment latch mechanism for the walker device.

FIG. 48A is front view of an improved suspension system incorporated into a lower body suit which allows unrestricted body and leg movements by the patient, and permits quick attachment and detachment by the patient from the walker device.

FIG. 48B is a left-side view of the lower body suit of FIG. 48A containing the suspension system.

FIG. 48C is a rear view of the lower body suit of FIG. 48A containing the suspension system.

DETAILED DESCRIPTION OF THE PREFERRED EMBODIMENT

Figure 1:
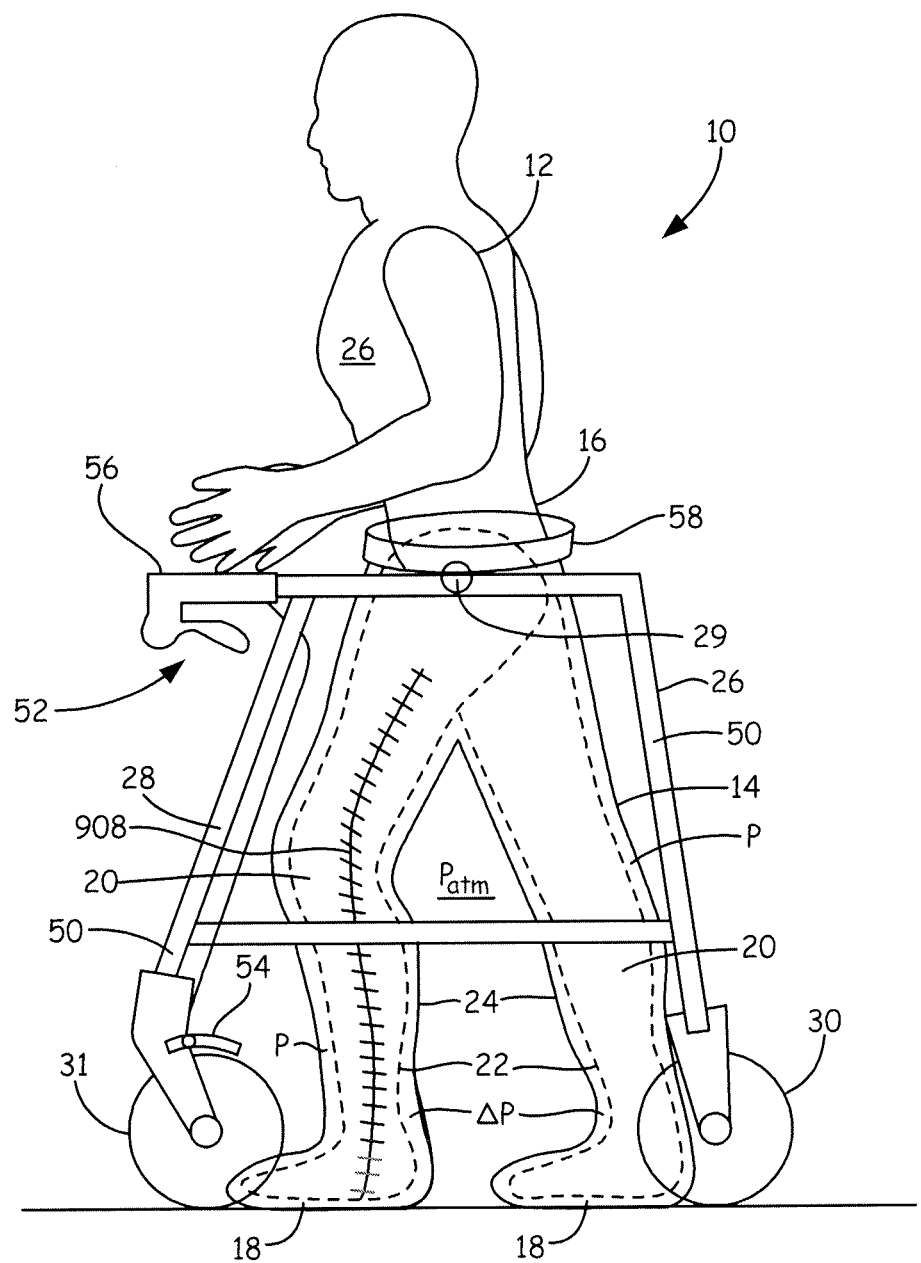
FIG. 1 is a perspective view of a mobile walker support structure used with the pressurized body suit.

A body lift-assist walker device for gait training is provided by the invention. It provides a portable and convenient system for persons undergoing physical therapy for treatment of gait or balance problems following an injury, stroke, or neurological disorder, or for use by elderly or disabled persons who have encounter difficulties in the sit-to-stand movement or walking. The device comprises a frame with wheels that a patient can lean on while walking. The patient wears a pressurized body suit over all or a portion of his lower body, and the suit is attached to the walker device. A positive pressure or vacuum condition is applied to the interior of the suit, so that the differential pressure condition across the suit offloads a portion of the patient's body weight to the ground through the supportive walker device to make it easier for him to walk or run. At the same time, the walker device acts against body suit migration that is caused along the patient's lower body by the differential pressure condition. Alternatively, the patient may be fitted with a harness system operatively attached to the walker device for offloading a portion of his body weight. The walker device also includes a lift-assisted body weight support device operated by a constant force mechanism like a pneumatic air cylinder that can lift the patient from all types of sitting furniture to a standing position. The device is easily adjustable by the therapist to fit patients of all sizes and allows full access to the patient's legs during gait training.

For purposes of the present invention, "differential pressure" means the difference in pressure conditions across opposite sides of the body suit, such as a positive pressure or negative (vacuum) pressure condition contained inside the suit, and an atmospheric pressure condition on the outside of the suit. For example, if atmospheric pressure is equal to 14.7 lbs/in$^2$ ("psi"), and the internal pressurized condition of the body suit is 15.7 psi, then the differential pressure applied by the body suit to the mammal wearing the body suit is 1.0 psi. Such differential pressure can also be represented as $\Delta P$ within this application.

As used within this application, "positive pressure" means any pressure level in excess of atmospheric pressure.

For purposes of this application, "negative pressure" means any pressure level less than atmospheric pressure. A vacuum is an example of such a negative pressure. Partial vacuums are also covered by this invention.

In the context of the present invention, "body portion" means any lower part of the body below the waist to which the differential pressure condition is applied by the body suit. Examples include, without limitation, feet, legs, knees, and hips.

As used within this application, "body suit" means a single or multi-layered, close-fitting or loose-fitting suit capable of containing a positive or vacuum pressure condition that covers a predetermined body portion. Examples include, without limitation, trunks, shorts, longer pants that extend from the waist to the ankles, and full-length pants that cover the feet. The suit is provided with a means for creating the positive or negative (vacuum) pressure condition within the suit. Such a means may be a port connected to an air pressure control system.

In the context of the present invention, "pressure-tight" means with respect to the body suit that the material forming such body suit is capable of containing a positive or negative pressure condition without substantial diminishment over a time period that is relevant to the usage of the body suit. Thus, pressure tightness does not require an absolute absence of any loss of pressure or vacuum, nor does it require maintenance of the positive pressure or vacuum condition within the suit for a time period greater than the time interval during which the suit is worn for an exercise or therapeutic treatment session, or beyond which such positive pressure or vacuum condition can reasonably be replenished within such exercise or therapeutic session.

For purposes of the present invention, "mammal" means any of a class of higher vertebrates comprising humans and all other animals that nourish their young with milk secreted by mammary glands, and have the skin usually more or less covered with hair. Such animals include, without limitation, horses, dogs, and cats.

A human patient will be used as an exemplary mammal for purposes of describing the body lift-assist walker device of the present invention. It is important to appreciate, however, that any other type of mammal for any other kind of exercise, life activity, or rehabilitative activity is covered by this application, as well.

The body lift-assist walker device 10 of the present invention is shown in FIG. 1. Unlike prior art static systems that require a person to use a stationary treadmill, this system is portable, thereby enabling the person 12 sufficient mobility to undergo physical therapy or gait therapy treatment, or to enjoy walking or exercising outdoors on the road or a trail. In this embodiment, the person wears a differential pressurized pant suit 14 that extends downwardly from the person's waist 16 and covers the feet 18. The runner's legs 20 are depicted inside the differential pressurized suit 14 in broken lines 22.

The differential pressurized suit 14 is constructed of air-tight material, and affords easy movement by the body and limbs of person 12 while running. The suit 14 is sealed against the body at the waist 16. When air pressure condition P above atmospheric pressure $P_{atm}$ is added to the volumetric region 24 defined between the person's legs 20 and the suit 14, a differential pressure condition $\Delta P$ is created in which the person's lower body portion contained within the suit 14 experiences a higher pressure condition than the person's upper body 26, which only experiences $P_{atm}$. Due to this pressure differential $\Delta P$, an upwards force is exerted on the person 12 by the higher air pressure contained inside the suit 14, thereby acting to diminish the weight of the person's body. Person 12 thereby experiences a reduced weight on his feet, knees, legs, and lower body when he walks in this differential pressurized suit 14, compared with if he walked without the suit.

FIG. 2 illustrates the various vector forces on the person's body. The person 12 and the differential pressurized suit 14 are depicted separately in FIGS. 2a and 2b, respectively, for ease of understanding. The force from gravity exerted on the person's body mass is shown as $F_g$. In use, the suit 14 is sealed to the person's body at the waist 16, and pressurized to pressure P to create the differential pressure condition ΔP between the upper and lower bodies. The cross-sectional area of the body at waist 16 is depicted as area $A_w$. The positive pressure P is directed against the body and legs 20. The differential pressure condition ΔP results in an upwards-directed resultant force $F_b$ on the body located at the centroid 17 of cross-sectional area $A_w$. This total upwards force $F_b$ is:

$$F_b = \Delta P \times A_w$$

This constitutes the amount of weight that is effectively reduced from the lower body 20 of person 12. For example, a person experiencing a pressure differential ΔP on the lower body of 0.5 psi having a cross-sectional waist area of $A_w$ of 100 square inches would experience a 50 lb reduction in weight due to the differential pressurized suit 14.

FIG. 2b illustrates the various vector forces on the suit 14. The cross-sectional area of the suit at waist 16 is depicted as $A_s$. In the case of a closely-fitting body suit, $A_s$ should approximate $A_w$. The positive pressure differential ΔP also results in a downwards directed force $F_s$ on the suit 14. The amount of this downwards force $F_s$ is:

$$F_s = \Delta P \times A_s.$$

This constitutes the amount of force that pushes the suit down the body. For example, a suit pressurized to a pressure differential ΔP of 0.5 psi having a cross-sectional waist area As of 100 square inches is subject to a 50 lb downwards force. This force $F_s$ would ordinarily cause suit 14 to work its way downwardly along legs 20. Therefore, an important part of the invention is the inclusion of the frame of the walker device 26 to act as a supportive device to prevent the downward migration of the suit. In the case of the embodiment depicted in FIG. 1, the walker device 26 constitutes a frame 28 that is operatively connected to wheels 30. The suit is attached to the frame 28 at attachment points 29. When the differential pressurized suit 14 is connected to frame 28, the downward force $F_s$ exerted on the suit 14 is matched by the upwards reaction force exerted by the supporting structure at the attachment points 29.

In this manner, the supported differential pressurized suit 14 is able to diminish the weight of the person's body without contacting the body. Through the application of differential pressure ΔP, an amount of weight ΔW of the body equal to:

$$\Delta W = W - (\Delta P \times A_w)$$

is transferred from the muscle-skeletal structure of the person's lower body 20 to the frame 28 of the supporting structure 26, and through the frame 28 and wheels 30 to the ground. Moreover, the support structure prevents force $F_s$ from pulling the differential pressurized suit 14 off person 12. Furthermore, because the wheel-based support structure 26 and differential pressurized suit 14 are completely portable in nature, person 12 can go anywhere with the body lift-assist walker device 10, instead of being confined to a stationary or pressure chambers as with prior art systems.

When the person's body is in contact with the ground via feet 18, various amounts of weight can be effectively removed from the body, depending upon the level of positive pressure P introduced to the body suit. For example, for a 180 lb runner having a cross-sectional area $A_w$ of 100 square inches, a differential pressure ΔP of 1 psi would reduce his weight by 100 lbs. The runner's lower body would therefore only need to support a weight of 80 lbs. A 0.5 psi pressure differential ΔP would take off 50 lbs of weight. A 0.25 psi pressure differential would take off 25 lbs of weight.

Figure 3:
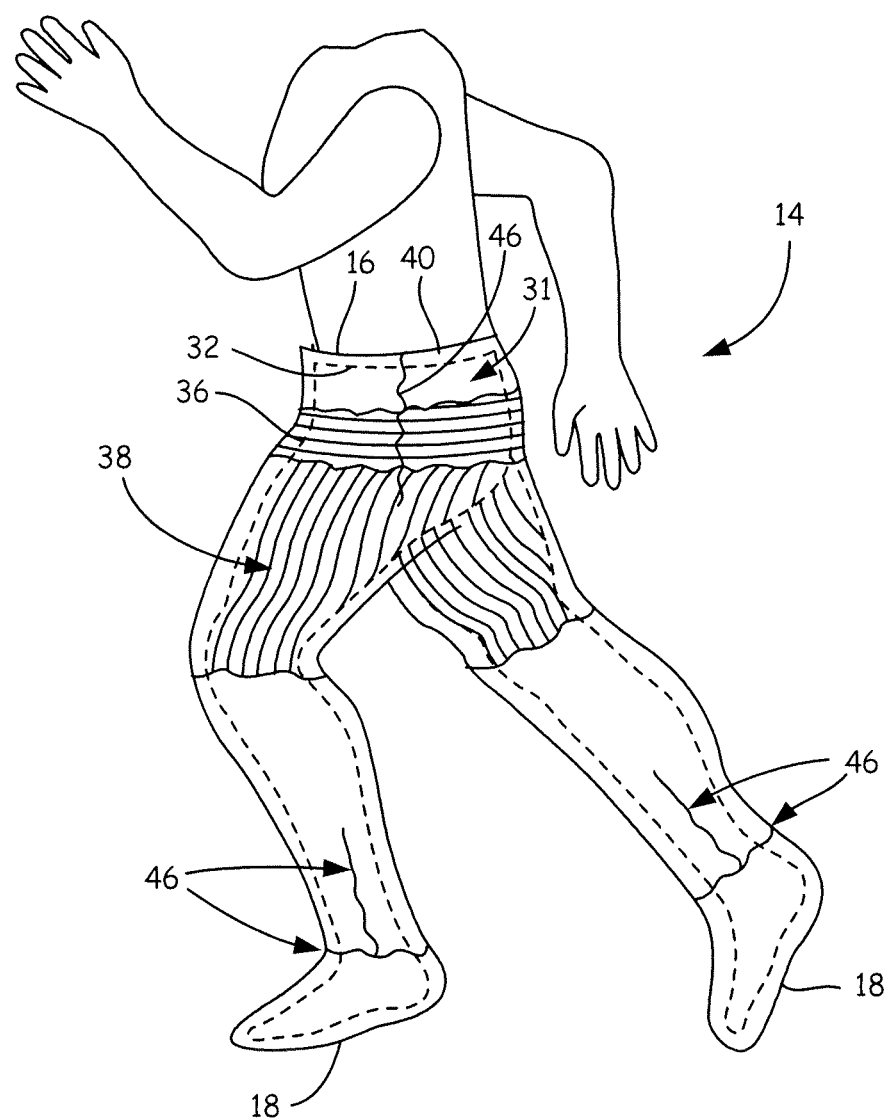
FIG. 3 is a cut-away view of the body suit.
Figure 4:
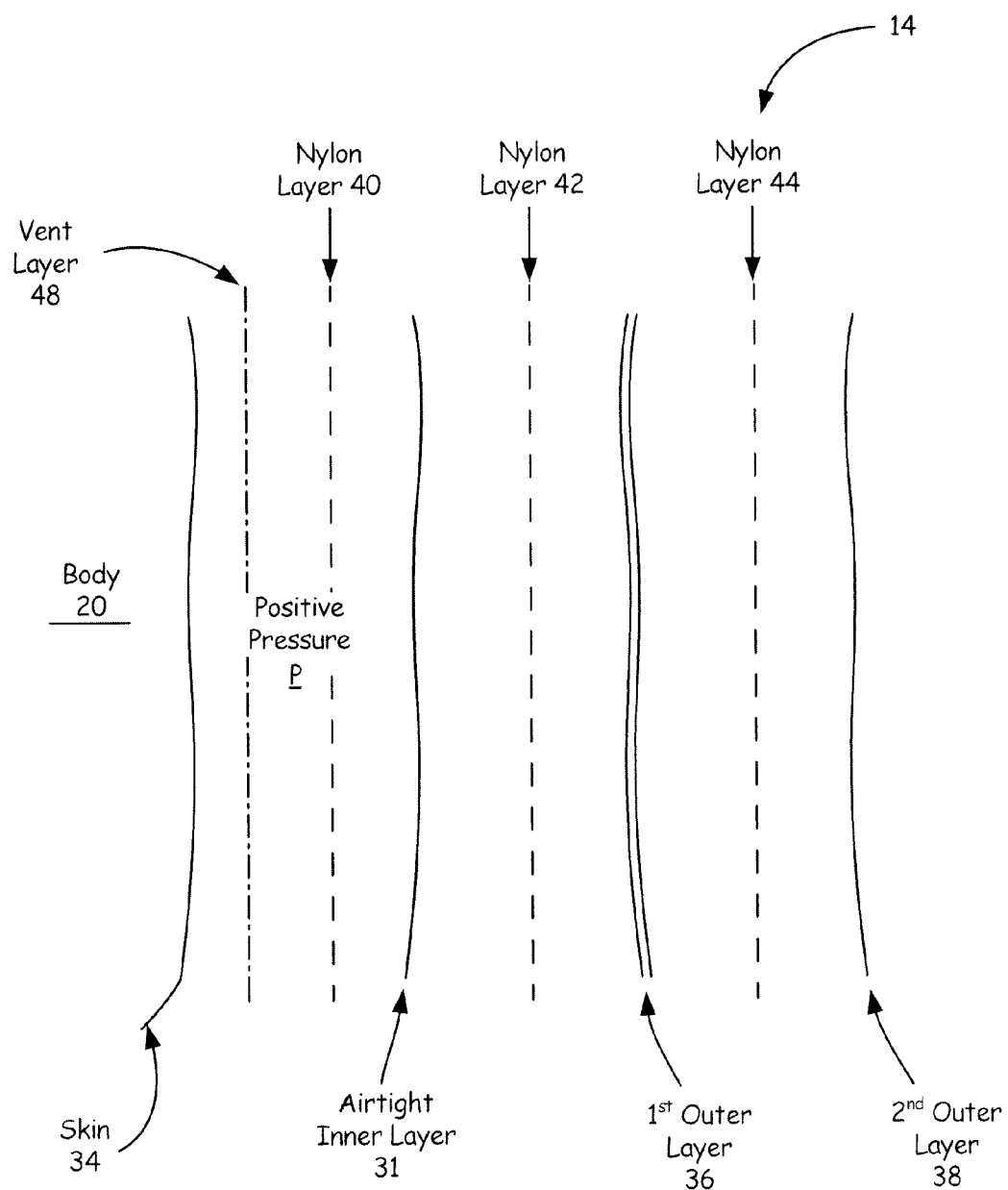
FIG. 4 is a schematic view of the construction of the body suit.

The preferred construction of differential pressurized suit 14 is shown in greater detail in FIGS. 3-4. Close fitting suits provide the advantage of greater mobility for person 12. Suit 14 is constructed from at least three layers of material. FIG. 3 shows a cut-away view of the suit illustrating its different layers.

An air-tight inner layer 31 featuring an airtight seal 32 at the waist 16 of the person's body 20 maintains the positive pressure P condition inside the suit against the person's body skin 34. The fabric for this air-tight layer which is closest to the body may be formed from any pressure-tight material that is also sufficiently flexible to afford mobility by the runner. Examples include, without limitation, latex rubber, neoprene, and air-tight elastic fabrics like latex-coated Lycra. This fabric should be sufficiently thin and elastic to provide comfort without restriction. Preferably, suit 14 is about 0.002-0.040 inch thick, more preferably about 0.005-0.015 inch thick, still more preferably about 0.010 inch thick. The elasticity of the material can be expressed by spring rate, which is the force necessary to double a one-inch-thick strip of fabric. Preferably, this spring rate should be about 0.2-2.0 lbs, more preferably about 0.5-1.5 lbs, still more preferably about 1.0 lb.

Two outer layers 36 and 38 of the differential pressurized suit 14 composition prevent the suit from expanding due to the force applied by positive pressure P, while maintaining the shape of the suit to fit closely to the body. This close fit provides for ease of mobility of the body and its limbs 20. It also prevents the legs of the suit from contacting each other during the walking motion. Moreover, this close fit of the suit reduces the volume of pressurized air or other suitable gas in contact with the body joints in order to facilitate bending of the legs.

The fabric for these first and second outer layers 36 and 38 should be composed of mesh, netting, or other suitable fabric. Suitable mesh material is available from Apex Mills Corporation of Inwood, N.Y. This mesh or netting is constructed to mostly be non-extending along one axis, and elastic or extensible along a second axis perpendicular to the first axis. Exemplary mesh materials include, without limitation, nylon-Lycra that can be knit or braided, or a monofilament like nylon or Dacron.

The first outer layer 36 serves to prevent the suit 14 from expanding circumferentially. The circumferential direction of expansion is perpendicular to the longitudinal axis of the legs and body fabric. The fabric is oriented so that its non-extending axis follows this direction. The fabric can be more specifically oriented so that its non-extending axis follows lines on the body in which the skin does not stretch or extend during bending or other movement. These lines are known within the industry as "lines-of-non-extension." Lines of non-extension run both parallel and perpendicular to the longitudinal axis of the legs and body. This first layer of fabric preferably would follow the perpendicular lines of non-extension.

The second outer layer 38 serves to prevent the suit 14 from expanding longitudinally under pressure. This fabric layer is oriented, so that its axis of non-extension generally follows lines that are generally parallel to the longitudinal axis of the legs and body. Preferably, the fabric can be more specifically oriented in this direction to follow longitudinal lines on the body in which the skin does not stretch or extend during bending or other movement. Where appropriate in sections of the body which do not flex, such as the thigh area or lower calves, cloth, mesh, or net material that is non-extendible along both axes may be used. This second outer fabric layer 38 which is mostly non-extensible in the vertical direction of an upright body effectively carries the vertical downward load on the suit resulting from the positive pressure differential.

Differential pressurized suit 14 may also feature additional layers of nylon 40 between the body 20 and the air-tight inner layer 30, and 42 and 44 between the inner 30 and first outer layer 36, and two outer layers 36 and 38, respectively, in order to enable the suit and layers to slip relative to one another on the body to improve the person's mobility. Air-tight zippers 46 positioned along the suit 14 near its waist 16 and feet 18 portions allow for easy entry and removal of the suit. Such air-tight zippers are available from YKK (U.S.A.) Inc. of Marietta, Ga. Moreover, the suit 14 may feature an inner vent layer 48 that provides airflow and moisture control. In other embodiments these layers can be separately combined into a single layer that provides the same basic functioning as for the separate layers described above.

As discussed above, the walker device 26 can be used to assist the mobility of elderly or physically-disabled people or person's undergoing physical therapy or gait therapy, particularly those recuperating from leg or back injuries. The four-wheeled cart-like support structure 26 of FIG. 1 is utilized as a wheeled walker, commonly called a "Rollator." The above-described wheeled walker is also advantageous for those impaired persons with limited or no use of their hands and arms. When the pressure suit 14 of the present invention 14 is worn by such a person, the support aid provides the necessary support for that person instead of him having to resort to his arms and hands leaning on a conventional walker.

The support aid's frame 50 and front wheels 31 and rear wheels 30 are designed and sized so that the mobile unit has the functionality of standard wheeled walkers. The front wheels turn and pivot to allow for easy turning. All four wheels may also turn and pivot. Typically the wheels 31 and 30 are at least seven inches in diameter—preferably eight inches—to ensure better reliability. A three-wheeled walker may also be utilized. Moreover, to enhance the safety, convenience, and durability of a wheeled walking aid 26 and its parts, the wheeled support aid may utilize tubular seats, back seats, and baskets with spacers and cushions.

The wheeled support aid can be incorporated with hand-operated brake levers 52 and brakes 54. The brakes on the wheeled support walker 26 may constitute locking brakes to allow the person to stand while supported in a stationary position. Other means of braking may be provided for those with limited use of their arms and hands. The wheeled support walker can be designed to enable greater range for rotating the body from side to side to enable the person in the wheeled support walker to turn from side to side and stand facing one side or the other, or even the back. It may also have a seat that will allow for resting. The wheeled support walker will have adjustable height. The wheeled support walker may also be designed with a folding mechanism for compact storage.

The wheeled support walker can feature hand supports 56 for assisting the entry and exit from the support walker. The wheeled support walker can be constructed from lightweight materials such as aluminum or composites. The pressure-assisted wheeled support walker may preferably use tubular seats, back seats and baskets with spacers and cushions. The wheeled support walker can be equipped with a source of pressurized air to control pressurization of the suit, and means for balancing the downwards force of the suit automatically as the pressure is adjusted.

The elderly or disabled person 12 wears a pressurized suit 14 that attaches to the frame of the walker at attachment points 29. The various attachment methods previously described may be utilized. The previously described constant-force adjustment mechanisms may also be incorporated. For walking applications, there is minimal up and down vertical motion of the walker compared with a running motion, so less overall adjustment and force balancing is needed for this embodiment. Various embodiments of the pressurized suit 14 described earlier can be utilized with this wheeled support aid. The suit can be customized for easy entry and exit by physically impaired persons. In particular, the pressure suit can have extra long zippers and an easy entry supporting ring which makes the suit easy to put on for a physically impaired person.

Figure 5:
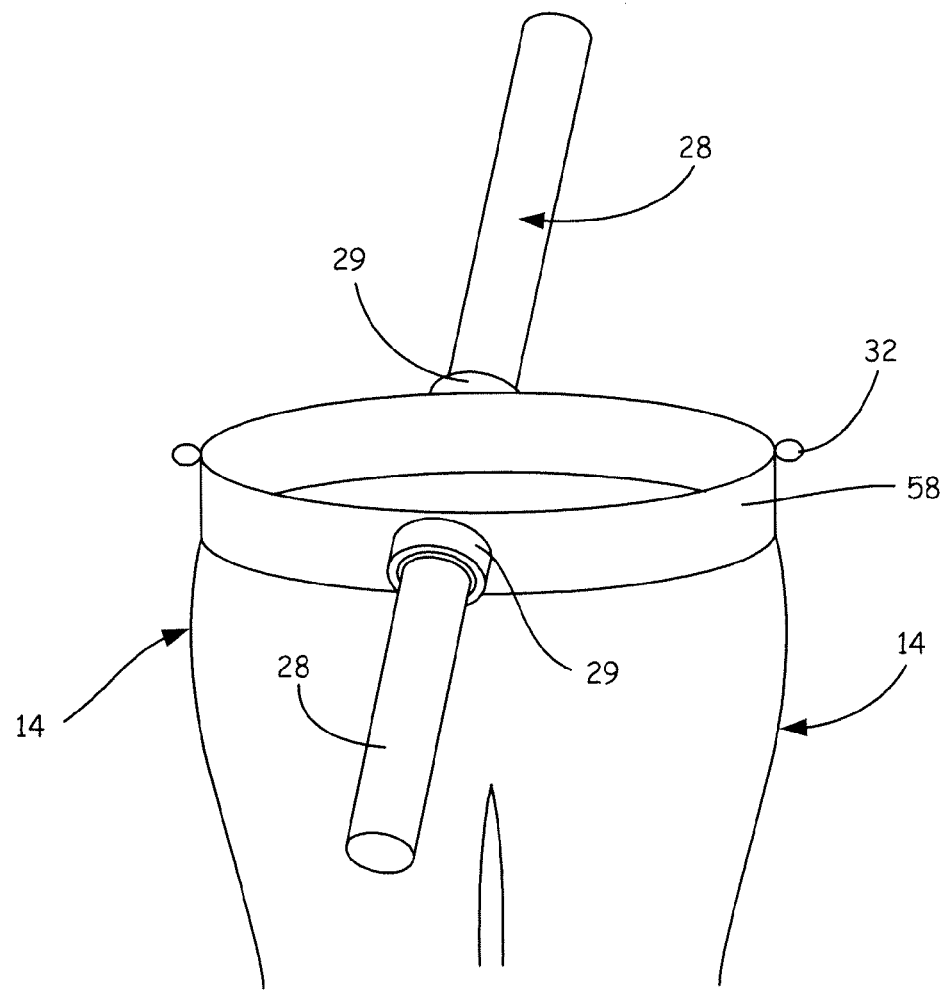
FIG. 5 is a partial view of the body suit connected to a portion of the external frame for the walker support device.

As shown in FIG. 5, a band 58 serves to attach the pressurized body suit 14 to the attachment means 28 (which is shown here schematically as a rod) of frame 50 of the walker device 26. This band is attached to the supporting structure with a fitting 29, such as a threaded collar receiving threaded ends extending from the cross bars 28 of the walker device 26. The band should conform to the generally elliptical shape of waist cross-section $A_w$ that surrounds the suit 14 at the waist 16. This band serves an additional purpose of containing the outward pressure force in order to enhance the radial inward force as the suit is filled with pressure. This assures that the suit will conform closely to the body at the waist 16.

The band 58 may be made from any suitable material that is strong enough to contain this outwardly-directed force, including metal, plastic, or composites. It may be made moldable to the general shape of the runner's waist, using a thermoset plastic material. The band 58 may alternatively be formed from a strong, flexible fabric, such as nylon. The suit 14 may be attached and detached from the band 58, using a Velcro fastening system. Other mechanical fastening systems such as straps, snaps, or hooks engaging eyelets may also be utilized. Alternatively, the band can constitute an integral part of the suit. The band may be in two pieces hinged and fitted with a locking clasp to allow for easy entry.

In the embodiments of the differential pressurized suit 14 shown in FIGS. 1-3, the suit covers the entire lower legs and feet, so that the entire lower body below the waist is airtight. A seal 40 is connected to the waist of suit 14 with an airtight connection, so that air pressure cannot escape between the suit and the seal. While the seal 40 may be positioned at the waist area, it may also be located lower, below the hips, or somewhere in between.

Figure 6:
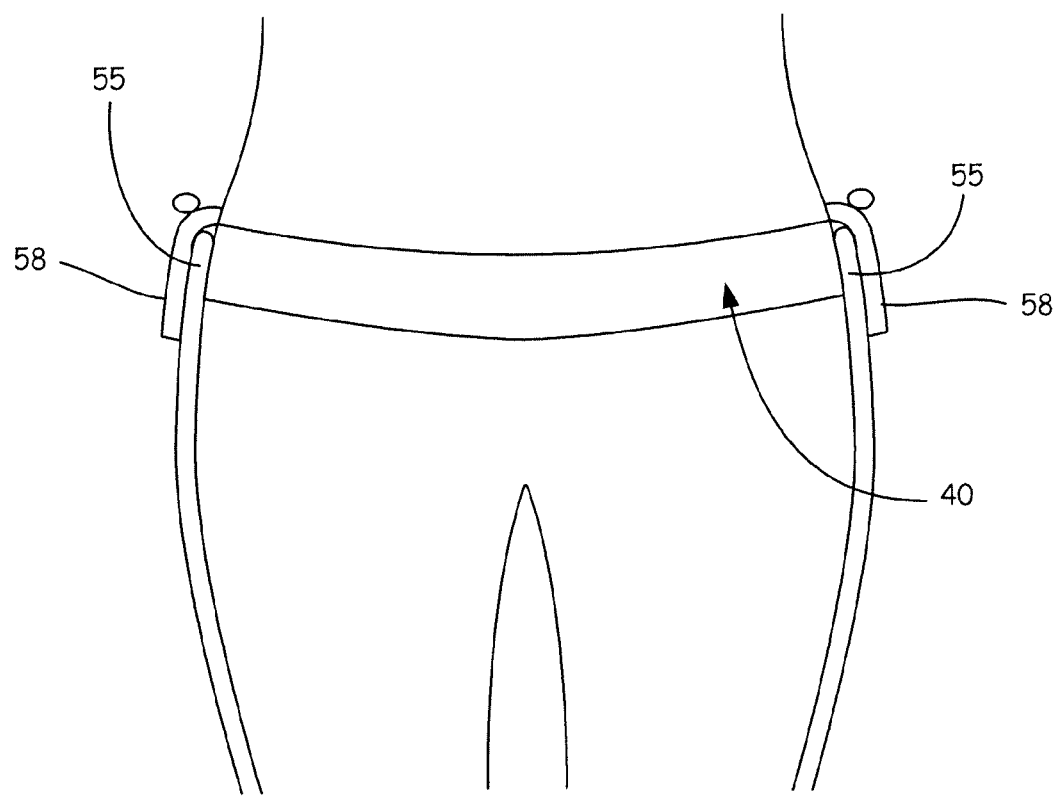
FIG. 6 is a partial front view of a waist seal attached to the interior of the body suit.

The seal 40 constitutes an airtight band of material that fits tightly over the body. As shown more clearly in FIG. 6, it is attached to the suit 14 at 55. This seal 40 is preferably constructed of elastic neoprene, or any other airtight material, such as rubber, latex, or a rubber-coated Lycra. Suitable latex rubber sheeting is available from Rubber Cal of Santa Ana, Calif. The seal should be sufficiently wide across the waist area of the suit to provide for a sufficient airtight closure. The circumference of the seal 40 should be less than the unstretched circumference of the body part that is circumscribed by the seal, so that when the seal 40 is secured around the body part (in this case, the waist area), a positive pressure is applied by the seal to the underlying skin. Combined with the air at pressure P that is introduced into the suit 14 within the volume between the suit's airtight inner layer 30 and the person's body skin, the suit 14 and associated seal 40 maintain a relatively airtight seal in order to confine the volume of air pressure P inside the suit. The seal 40 is sufficiently airtight that it provides enough sealing force to maintain the air pressure inside the suit using the air control system.

Figure 7:
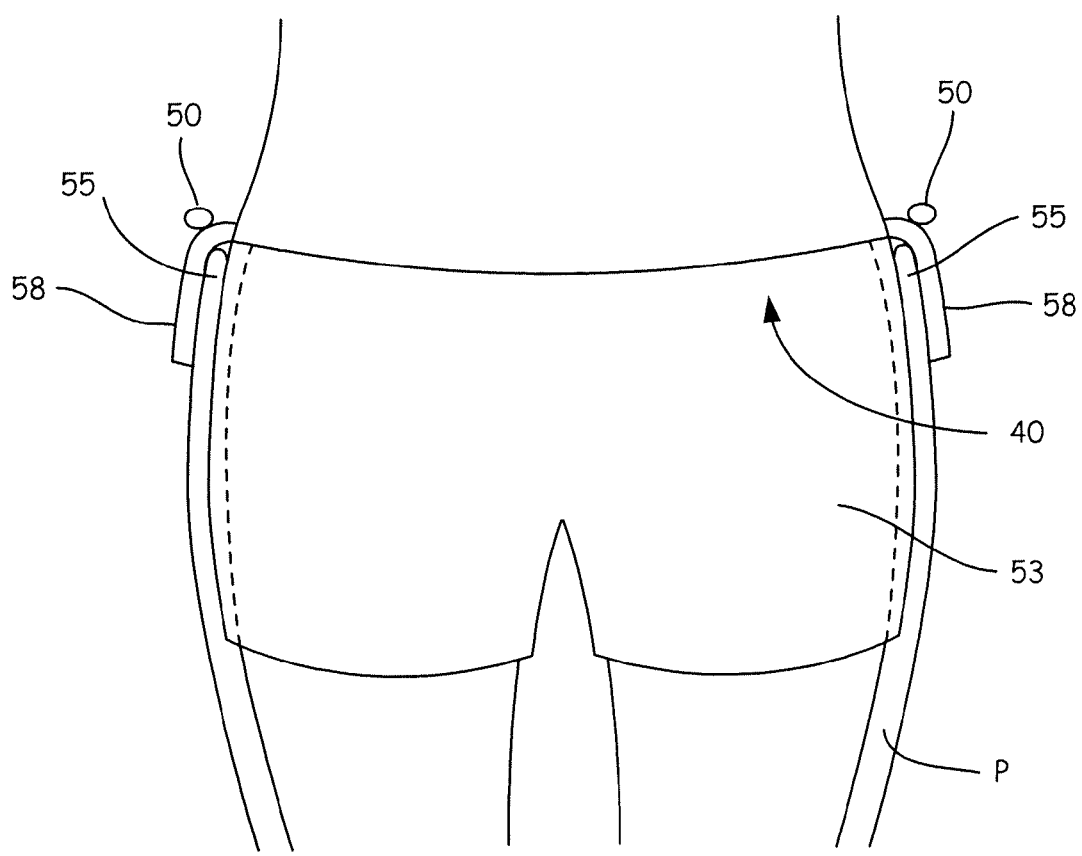
FIG. 7 is a cut-away front view of an alternative airtight shorts embodiment of a waist seal for the body suit.

FIG. 7 shows another embodiment of a waist seal for suit 14. In another embodiment of the differential pressurized suit 14 of the present invention, the waist seal can comprise an airtight pair of shorts 53 that are connected to the interior of the suit. Such shorts can be tight-fitting, airproof neoprene compression shorts that provide a tight fit against the body. These shorts can be connected to the suit at the waist by means of an airproof zipper. The shorts can also consist of a tight-fitting, breathable fabric that has a band of airproof latex or rubber coating at the top or bottom portion to provide the airproof seal against the body.

Figure 8:
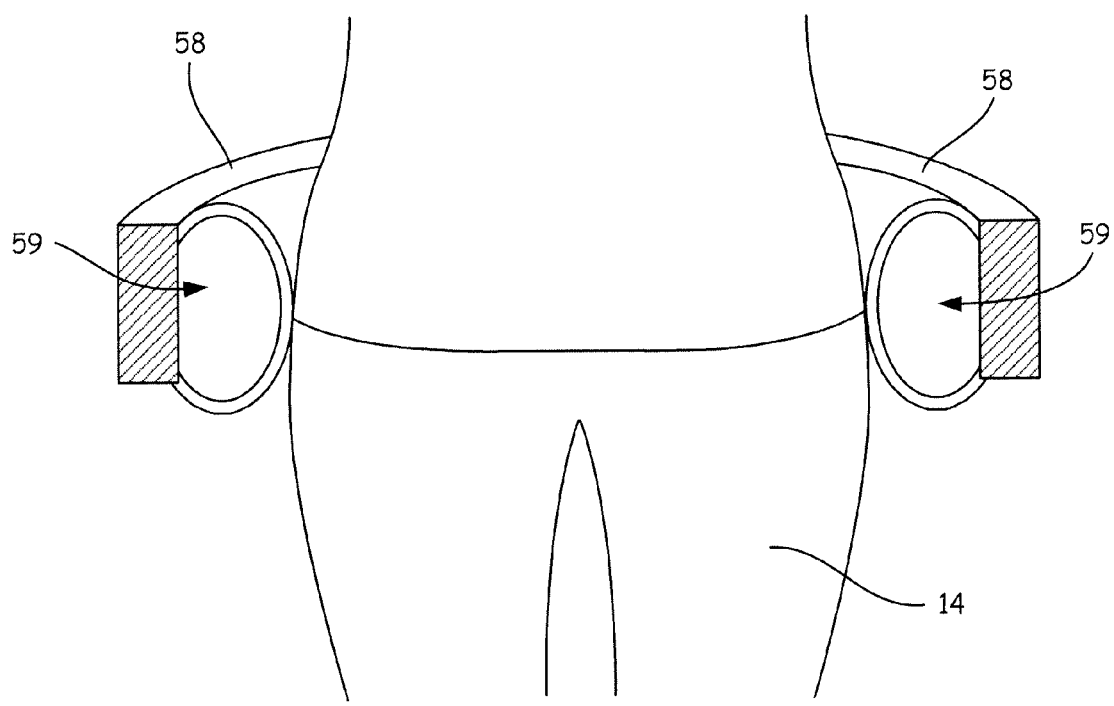
FIG. 8 is a cut-away front view of an inflatable air tube seal for the body suit.

In yet another alternative embodiment, the seal can consist of an inflatable air tube seal 59, as shown in FIG. 8. This inflatable tube seal circumscribes the waist, and is attached via an airtight connection to the exterior of the suit. When inflated with air, the tube seal 59 expands and applies an inwardly directed force to the waist to compress it against the skin to confine the air pressure P condition inside the suit.

Figure 9:
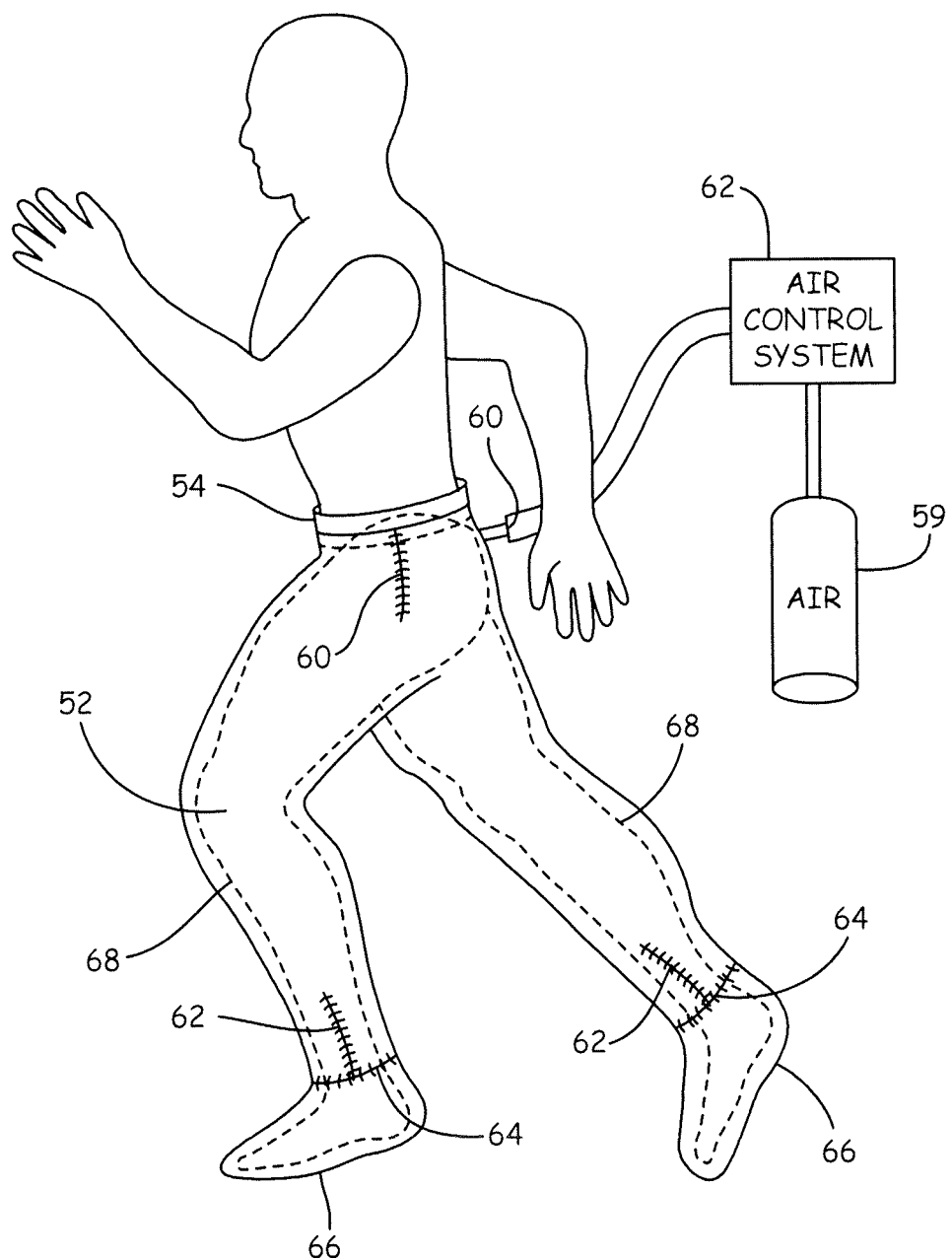
FIG. 9 is a perspective view of a human wearing a full-length pants body suit.

As shown in FIG. 9, when suit 14 is pressurized, it maintains a shape close to the body, while affording mobility of the body and limbs. A port 60 is provided in the suit to allow for pressurizing and depressurizing the suit. An air control system 62 connected to an associated pressurized air source 64 maintains the positive pressure condition P inside the suit. The air control system 62 may also control the humidity and temperature levels existing inside the suit. The suit may be statically pressurized once, and then worn by the person without the control system 62. When operating in this manner, the seal 40 maintains the pressure condition for the duration of the time period that the suit is worn. The suit may be worn for time periods ranging between minutes for brief exercises to days for medical rehabilitation.

While this application discusses the use of pressurized air to fill the suit, other pressurized gases may be employed. Other examples of such pressurized gases include oxygen, nitrogen, carbon dioxide, and argon. Such gases must be non-toxic and not harmful to body skin, or else an inner layer must be worn between the gas and the skin to protect the skin and body.

The differential pressurized suit 14 shown in FIG. 9 comprises a full-length pair of pants which also completely cover the feet. Airtight zippers 66 assist entry into the waist region of the pants. Airtight zippers 68 do the same for ankle regions. Finally, airtight zippers 70 allow the foot portion 72 of the suit 14 to be attached to the pants portion 69 after the feet are inserted through the pant legs.

Figure 10:
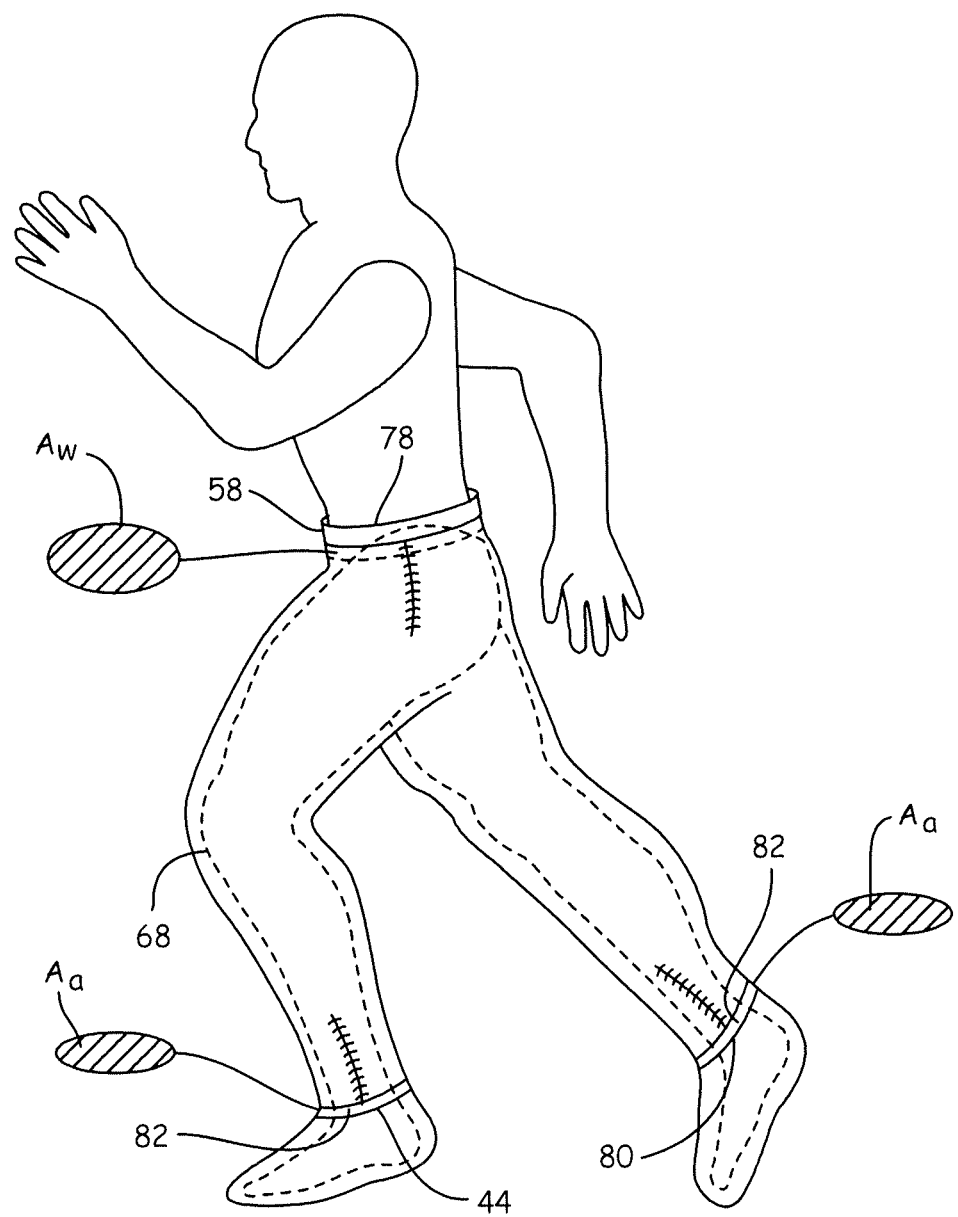
FIG. 10 is a perspective view of a human wearing a pants body suit only extending to the ankles.
Figure 11:
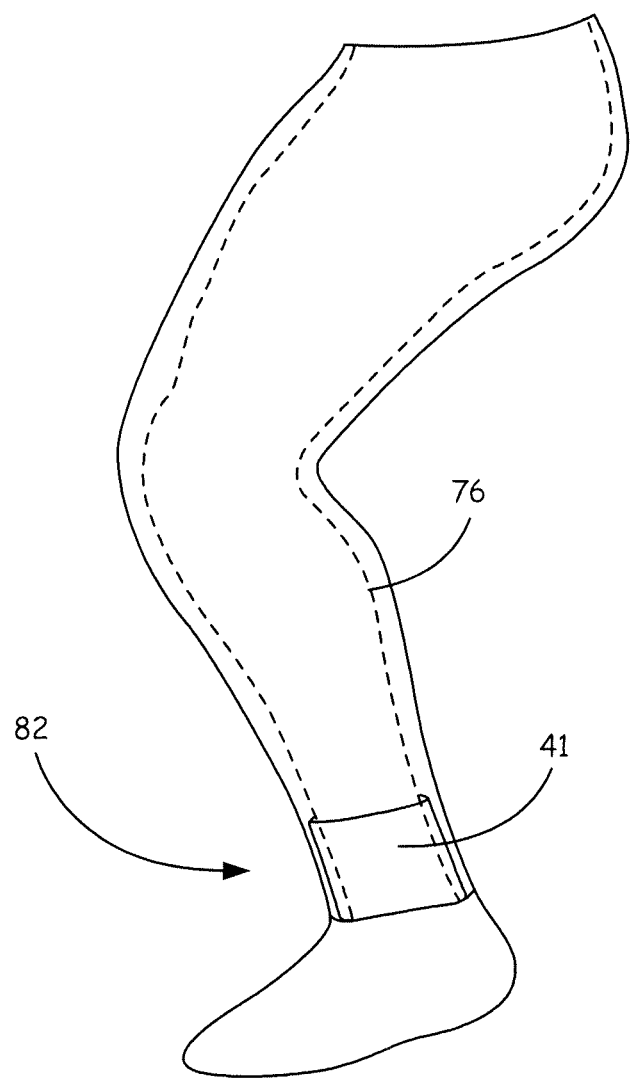
FIG. 11 is a cut-away view of a sleeve seal for the body suit of FIG. 10.

Still another embodiment of a differential pressurize suit 76 is depicted in FIG. 10. In this particular embodiment, the suit extends from the waist 78 to the ankles 80 without covering the feet, and is sealed at the ankle. The waist seal is as described above, and may include a rigid band 58 surrounding an air bladder. The ankle seals 82 are shown in greater detail in FIG. 11, and comprise a sleeve seal 41 connected inside the suit leg that is constructed of elastic neoprene, or another airtight elastic material, such as rubber, latex, or a rubber-coated Lycra. The sleeve seal 41 can be a tight-fitting, airproof neoprene compression sleeve that provides a tight fit over the ankle and lower calf. The sleeve seal 41 should be long enough to provide for a sufficiently airtight closure between the seal and the body skin. The unstretched circumference of the ankle sleeve seal 41 should be less than the circumference of the ankle and lower calf, so that when the sleeve seal 41 is secured around the ankle, a positive pressure is applied by the seal to the underlying skin by the elastic tension of the seals. In this manner, when the suit is pressurized with air to pressure condition P, the pressurized air is substantially contained within the suit 76.

By having suit 76 end at the ankles, motion by the foot will not be impaired by the foot portion of the suit. The suit 76 may also be put on more easily. Moreover, the wearer may wear normal-sized shoes.

The net upward force provided by pressurized air contained within suit 76 may be calculated as:

$$F_b = \Delta P(A_w - 2A_A)$$

where $\Delta P$ is the difference in pressure level P inside the suit and atmospheric pressure $P_{atm}$ outside the suit. $A_w$ is the cross-sectional area of the waist. $A_a$ is the cross-sectional area of each ankle.

Figure 12:
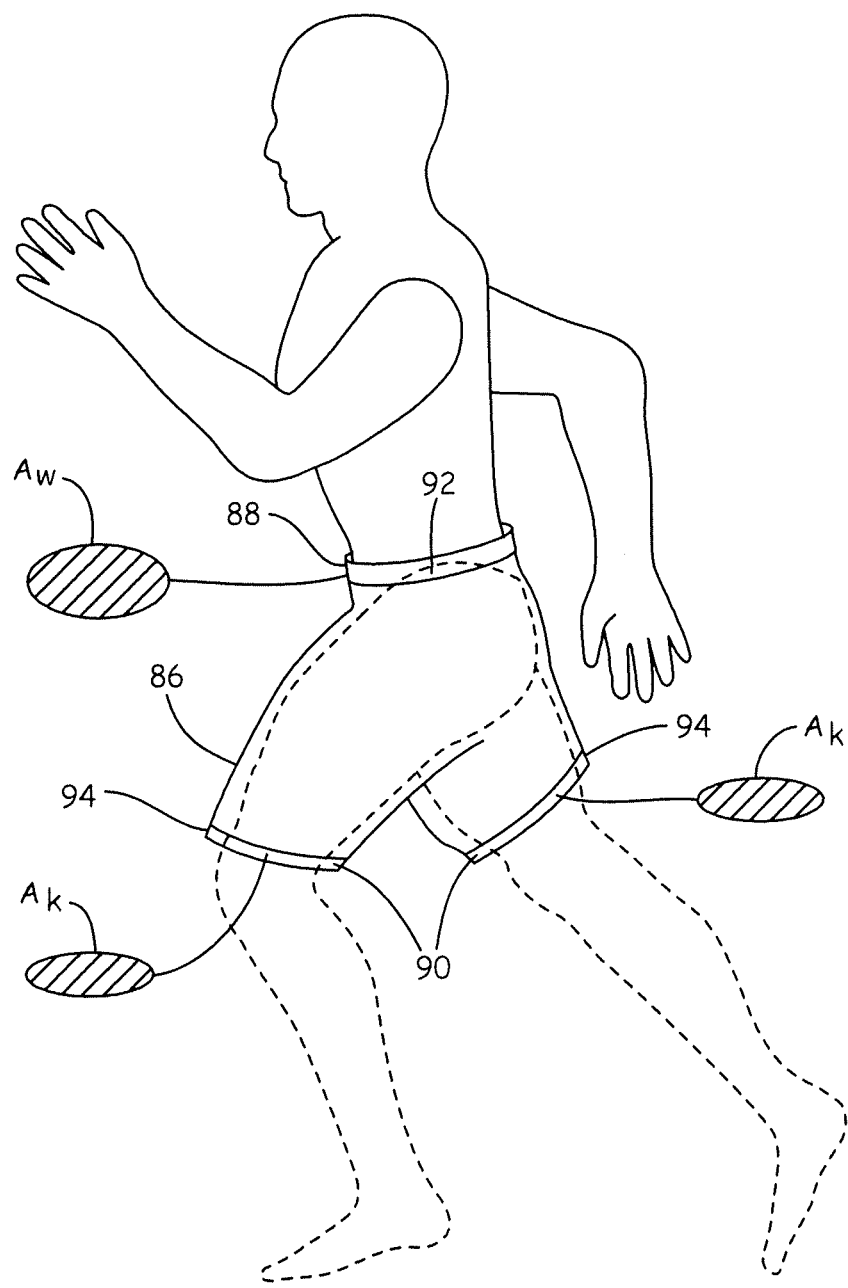
FIG. 12 is a perspective view of a human wearing a pants body suit only extending to just above the knees.
Figure 13:
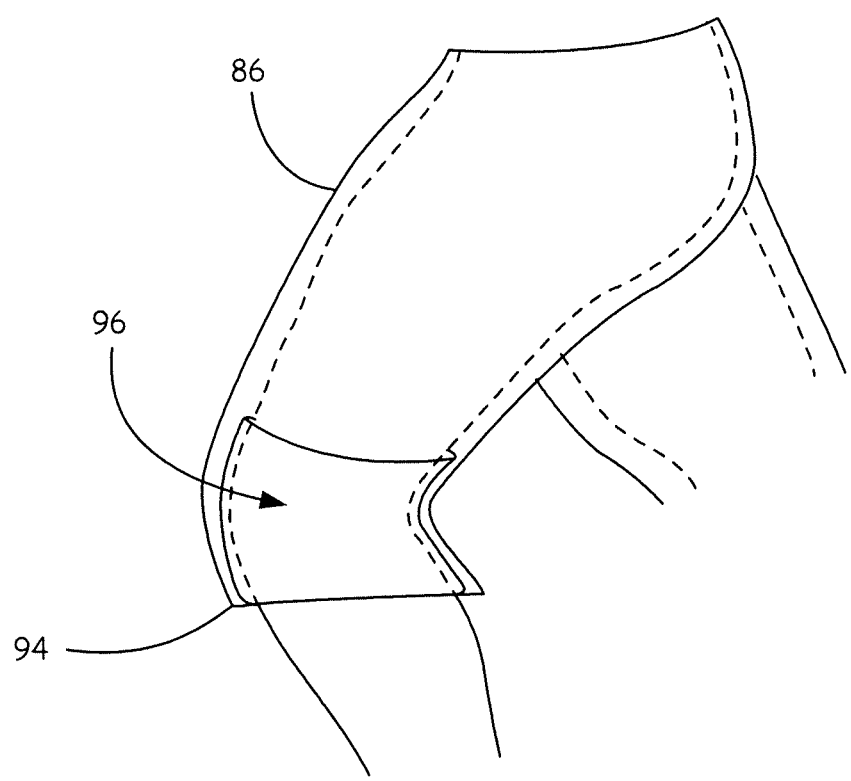
FIG. 13 is a cut-away view of a sleeve seal for the body suit of FIG. 12.

Another embodiment of differential pressurized suit 86 is shown in FIG. 12. In this embodiment, suit 86 extends to just above the knee. It is sealed at the waist 88 and at the knees 90. The waist seal 92 is as describe above. The knee seals 94 are shown in greater detail in FIG. 13. The sleeve seal 96 is an airtight sleeve connected to the interior of the suit 86 that fits tightly over the lower thigh. The sleeve seal should be long enough to provide for a sufficiently airtight closure. The circumference of the knee sleeve seal 96 should be less than the unstretched circumference of the lower thigh, so that when the seal 96 is secured around the knee, a positive pressure is applied by the seal to the underlying skin. This sleeve seal 96 is preferably constructed of elastic neoprene, or any other air-tight material, such as rubber, latex, or rubber-coated Lycra. An advantage provided by this suit 86 is that the person's knee and lower leg are free to move without any restriction posed by suit 86. This suit 86 is also easier to put on and take off.

The net upwards force supplied to the person's body when suit 86 is filled with pressurized air is:

$$F_b = \Delta P(A_w - 2A_k)$$

$\Delta P$ is the difference in pressure between pressure condition P contained inside the suit 80 and atmospheric pressure $P_{atm}$ existing outside the suit 86. $A_W$ is the cross-sectional area of the waist. $A_K$ is the cross-sectional area of the spot on each leg just above the knee where seals 94 engage the leg.

Figure 14:
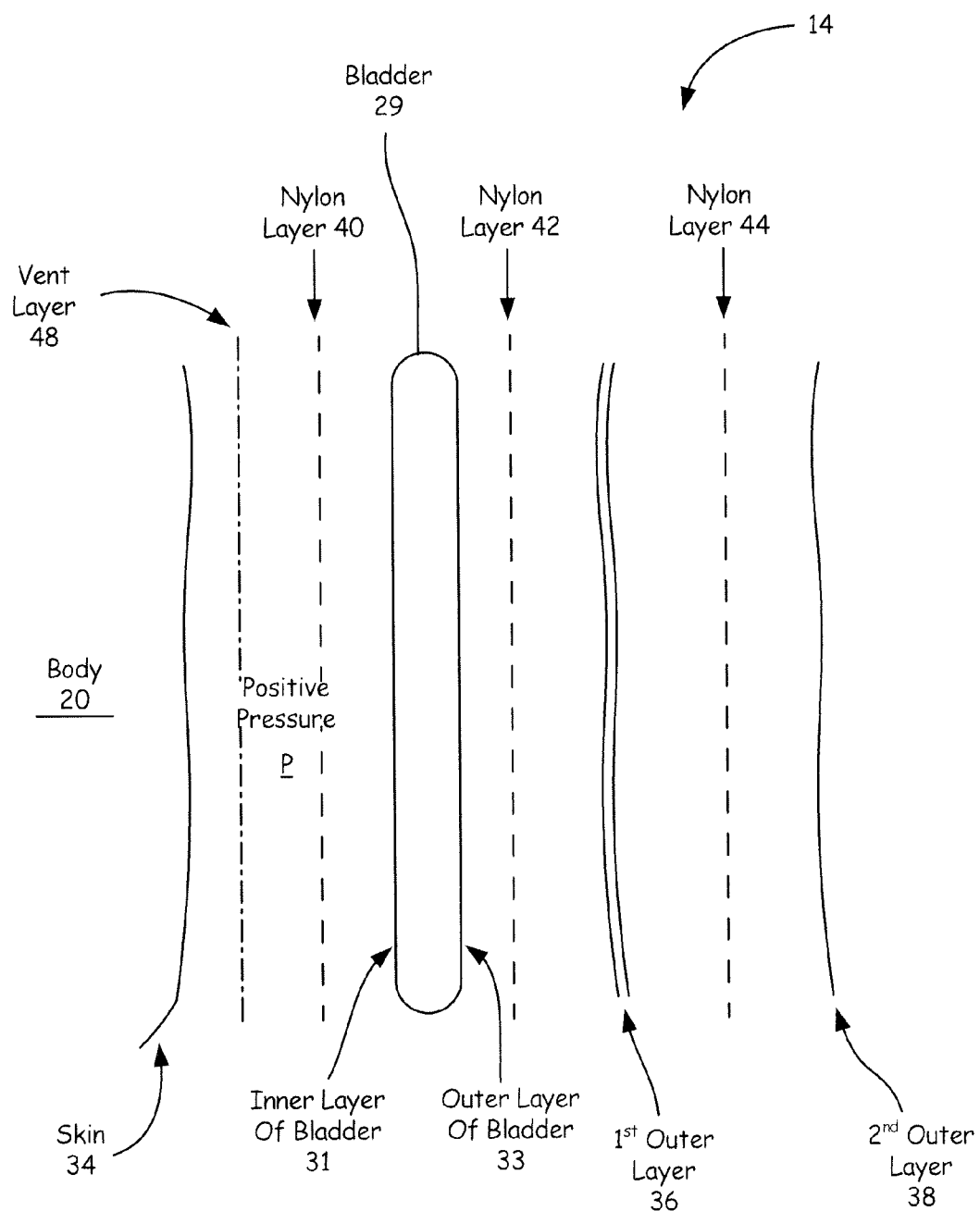
FIG. 14 is a schematic view of the body suit construction further comprising an airtight bladder sealing means.
Figure 15:
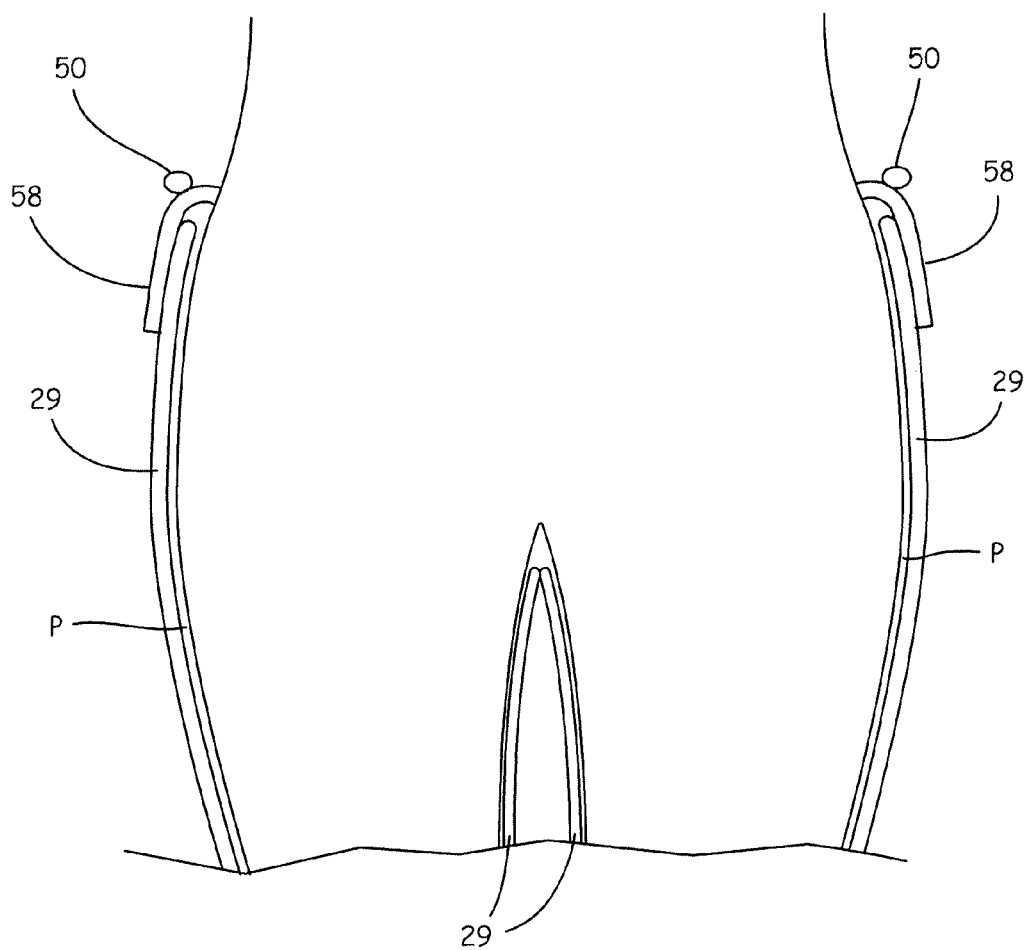
FIG. 15 is a front partial view of the air bladder construction of FIG. 14.
Figure 16:
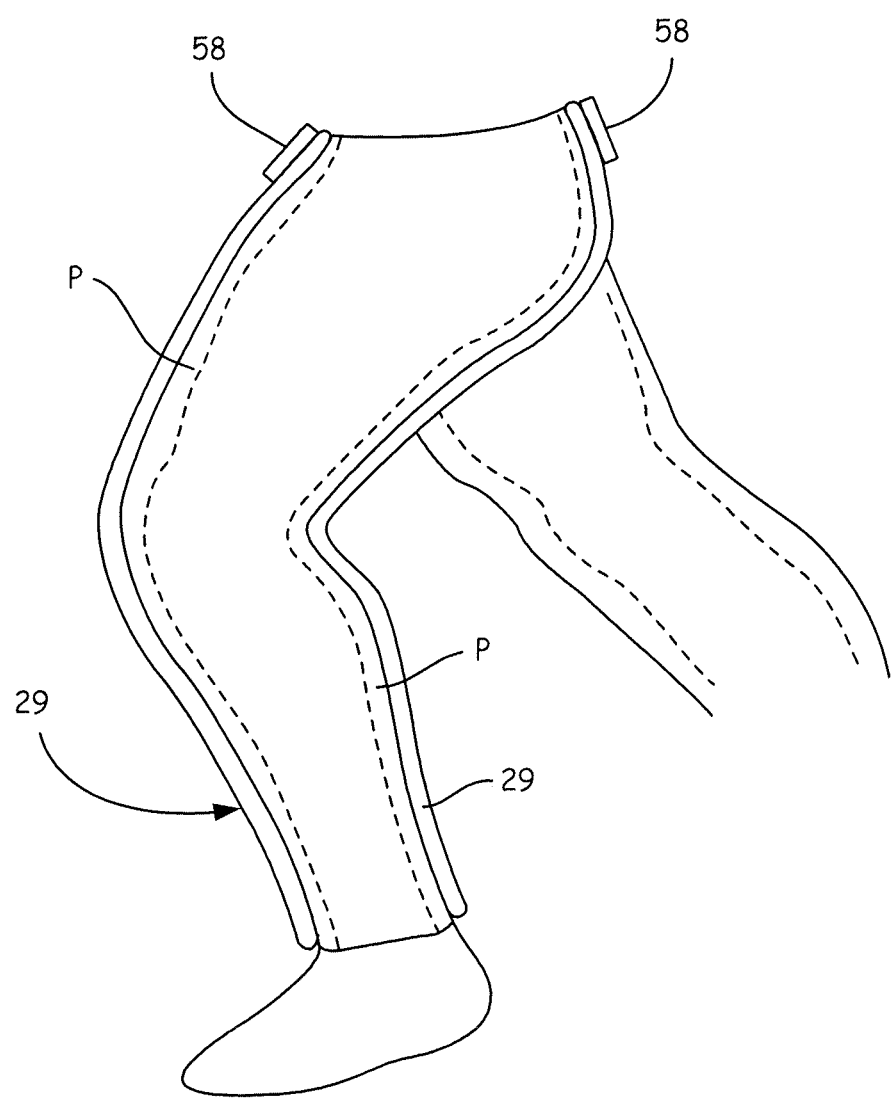
FIG. 16 is a side partial view of the air bladder construction of FIG. 14.

In another embodiment shown in FIG. 14, the pressurized air is contained within the body suit by means of an air-tight bladder 29 illustrated in an expanded view of the layers of the suit. The bladder consists of an airproof inner layer 31 and outer layer 33. The two layers are joined at the top and bottom of the suit to form an air-tight bladder 29. This bladder is essentially two identical air-proof layers, nested one inside the other, and sealed together at the top waist area and bottom of each leg of the suit. When pressurized, the inner layer presses against the skin and the outer layer presses against the outer constraining layers 36 and 38. A frontal view of the bladder 29 is shown in FIG. 15. A side view of the bladder is shown in FIG. 16. The bladder 29 contains air at pressure condition P. The bladder may be used for the various embodiments of the pressure suits described herein, including a bladder that extends from the waist to around the foot, a bladder that extends from the waist to the ankle, and a bladder that extends from the waist to above the knee.

The various configurations of suits described above provide high to lower amounts of upwards force $F_b$ on the body, depending upon the location of the seals. The complete lower body coverage suit 14 of FIG. 1 provides the greatest upper lift to the body, because:

$$F_b = \Delta P \times A_w.$$

The waist-to-ankle suit 76 of FIG. 10 provides the next largest amount of lift, because:

$$F_b = \Delta P(A_w - 2A_a).$$

Next in decreasing progression is the waist-to-just-above-the-knee suit 86 of FIG. 12, because:

$$F_b = \Delta P(A_w - 2A_k).$$

For most humans, their body anatomy is such that $A_a < A_K$. A leg suit with a top seal at the upper thigh and a bottom seal at the ankle (not shown) provides the next highest amount:

$$F_b = 2\Delta P \times (A_t - A_a).$$

A leg suit with a top seal at the upper thigh and a bottom seal at the spot above the knee (not shown) provides the lowest amount:

$$F_b = 2\Delta P \times (A_t - A_k).$$

A rubberized nylon can be utilized to construct a single-layer suit. This can be sewn into the appropriate shape using a standard sewing machine. Thigh seals can be made from a commercially-purchased neoprene compression sleeve. Compression sleeves are available from Advanced Brace of Irving, Tex. Neoprene compression shorts are available from the same supplier. The compression sleeve can be sewn interior to the pant around the thigh opening, and made airtight with seam sealer in the form of Seam Lock sold by REI, Inc. of Sumner, Wash. to make the seam airtight. A shorts-type waist seal can be constructed by sewing the waist area to the outer rubberized nylon suit, and sealing the seams to make it airtight. Alternatively, a compression sleeve may be connected to the rubberized nylon exterior suit, by placing each over an appropriate diameter steel band, and then clamping together the two layers of material with another outer ring. A standard air intake fitting can be installed in the pants to provide a port for pressurizing the suit.

Another important aspect of the body lift-assist walker device 10 of FIG. 1 is the external support structure of the walker 26 that is necessary for preventing the downwardly directed force $F_s$ on the suit created by the positive pressure differential $\Delta P$, from forcing the suit down and off the person's body. The external support structure 26 constitutes a frame 28 and wheels 30 for providing complete mobility to person 12. Such support structures should be designed for the specific range of body motions that the person wearing the suit plans to carry out.

The pressurized suit 14, as described in other embodiments of this invention, will create a force along the vertical axis of pushing the body up, with the reaction force being that of pushing the suit down. The latter is countered in this embodiment by offloading this downward reaction force to the frame 50, thereby effectively delivering part of the person's weight to the frame and thus to the ground through the wheels.

The waist band 58 allows for both rotational and angular pivoting of the person's torso during the motion of walking. In this embodiment, the mechanism simply consists of a flexible pleated material surrounding the region about the waist of the pressure suit, which may bend and twist with the movement of the person's torso. Other mechanical mechanisms for this purpose may also be utilized.

An optional constant force extension mechanism incorporated into the frame 50 of the walker device 26 may be used that provides a constant upwards force on the pressure suit allowing it to move vertically with the vertical motion of the person's body during the walking stride. The constant force of the mechanism is adjustable so that the upwards force on the mechanism is equal to the downwards force of the suit under pressure. The suit can thus float vertically up and down with the motion of the person's torso, while maintaining an essentially constant upward force on the suit. A range of motion of 0-7 inches is provided to accommodate various runners, with 3 to 4 inches being a typical vertical displacement in running motion. A typical displacement for walking is 1-2 inches.

This constant force extension mechanism may comprise pneumatic springs. Preferably, these springs provide a constant force to support the vertical downwards loads from the suit and walker cross bars to which the suit is attached, and allow for vertical motion of the person 12. In other embodiments, the springs may be constant-force mechanical springs, as is known in the art. The springs may also be mechanical or pneumatic springs that are not constant force. The springs are connected to vertical leg members of the walker device.

In usage, the constant-force air cylinders are each set such that the total force equals the desired weight to be subtracted. Air cylinder actuators are available from Bimba Manufacturing Company of Monee, Ill. Prior to pressurizing the pants 14, the person clips into the hooks on the air cylinder apparatus. Once this is done, the pants 14 may be pressurized. By standing on a scale, the pressure may be set to subtract the desired weight. Alternatively, since the pants characteristics should be known a priori, a specific calculated pressure P applied to the pants 14 will yield a specific weight subtraction. The desired weight subtraction set via the pressure P, and the counter force supplied by the air cylinders can be approximately matched. A control system can apply the correct calculated pressure to the constant force springs. During walking or running, a person could move vertically from 1-7 inches, typically 1-4 inches, vertically relative to the walking surface. The function of the air cylinders is to maintain a constant offloading of the reaction force dynamically, in response to this vertical displacement during walking.

Figure 17:
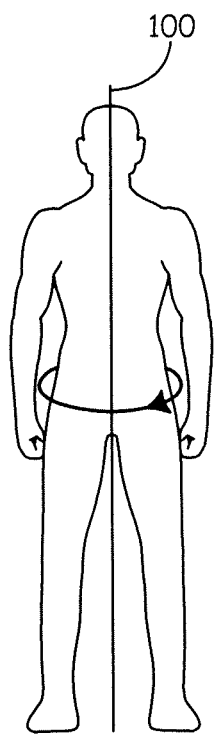
FIG. 17 is a schematic showing the superior-inferior axis of rotation for a human body.
Figure 18:
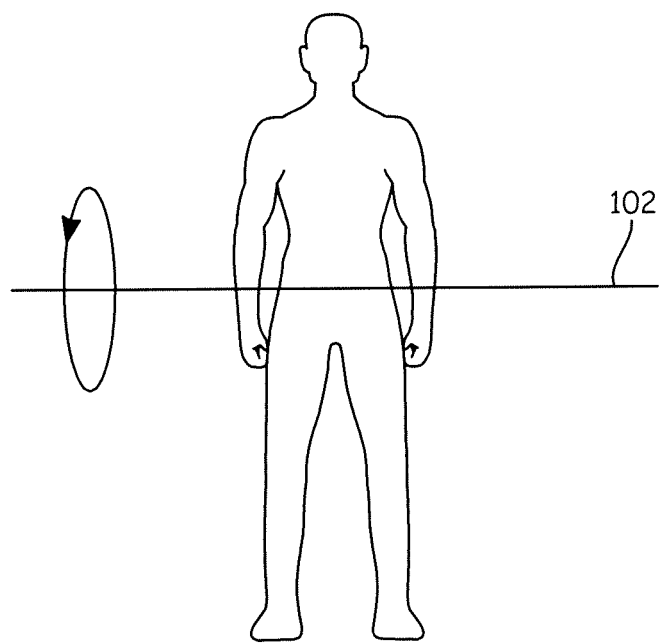
FIG. 18 is a schematic showing the medio-lateral axis of rotation for a human body.
Figure 19:
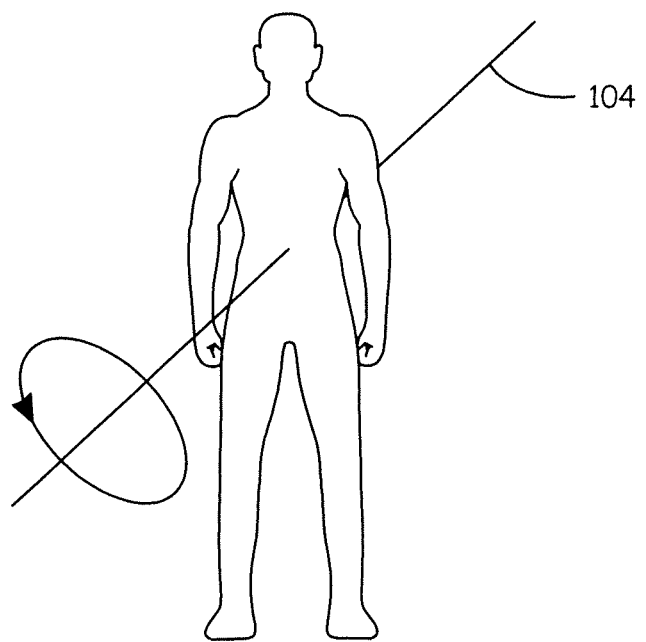
FIG. 19 is a schematic showing the anteroposterior axis of rotation for a human body.
Figure 20:
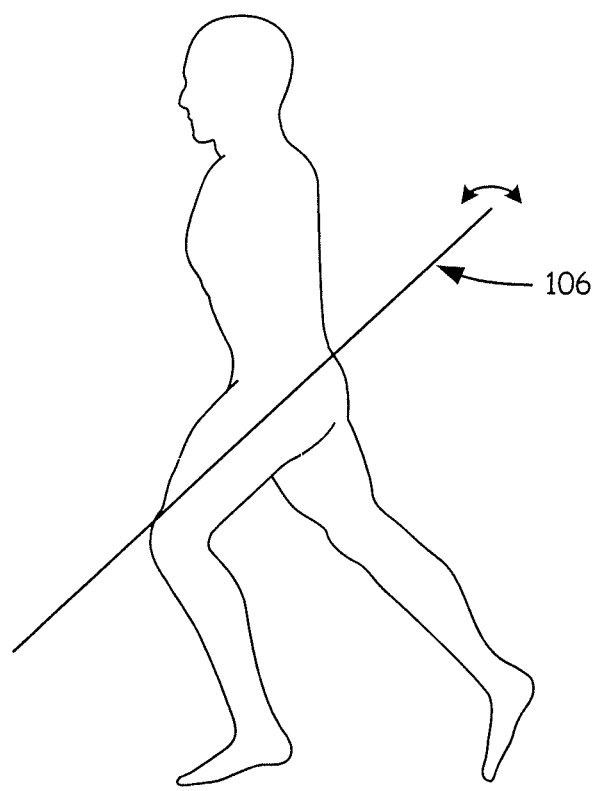
FIG. 20 is a schematic showing the medio-lateral axis of rotation through the hip joints for a human body.

The invention provides body weight support in a way that does not restrict one's natural body movements that occur while walking or running. Specifically the invention is an improved system for a body weight support device for connecting a person's body to the weight off-loading components of the device (referred herein to a constant-force adjustment mechanism) so as not to restrict natural body movements. During walking or running gait the body moves and rotates about various axes of the body shown in FIGS. 17-20. First, the superior-inferior axis 100 (i.e. vertical axis) is shown in FIG. 17. A person's hips and lower body rotates back and forth about this axis when walking or running as the leg and hips are moved forward at the start of a gait cycle and backwards at the end of the cycle. Second, the medio-lateral (i.e. side to side) axis 102 is shown in FIG. 18. A person's body rotates about this axis as the person leans forward from a stationary standing position to run or walk, the degree of lean or rotation depending on the persons running style and speed. Third, the anteroposterior axis (i.e. front to back) axis 104 is shown in FIG. 19. During running or walking, the hips and lower body move up and down about this axis. Fourth, the legs rotate back and forth about a medio-lateral axis 106 through the hip joints as shown in FIG. 20. The present invention provides a means for supporting body weight without restricting body movement and rotation about these four axes of rotation.

Figure 21:
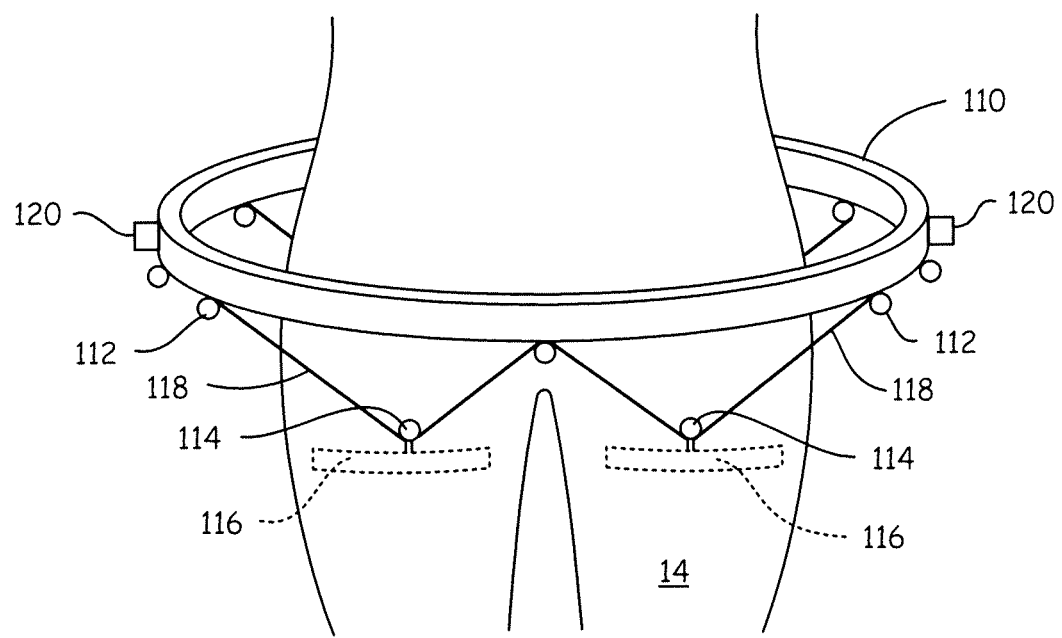
FIG. 21 is a perspective view of the pulley attachment between the body suit and the band of the body weight support device.

An alternative embodiment of the attachment means between the pressurized body suit 14 and the waist band 58 is shown in detail in FIG. 21. A rigid band 110 positioned about the waist of a person at approximately at the waist level. The band is substantially rigid in the vertical direction to support the body weight that is offloaded. In a preferred embodiment the band is a curved rigid aluminum strip 1 inch wide and ⅛ inch thick. The band may also be constructed to be flexible in the horizontal plane so as to be compliant and flexible around the waist, while rigid in the vertical direction to support the weight offloaded. Such a band can be constructed of multiple thin strips to provide flexibility. In one embodiment, the band is constructed from three stainless steel strips 1 inch wide and 1/32 inch thick that are bound together. Pulleys 112 are attached to the band at spaced intervals. Another group of pulleys 114 are attached to the suit at spaced intervals. In a preferred embodiment, a rigid supporting bar 116 is sewn into a sleeve in the suit, and the pulley is attached to it to provide for an even distribution of stress across the fabric of the suit. A cord 118 runs through the pulleys alternating between the pulleys on the body suit and the pulleys on the band. The ends of the cord are joined so that it forms a continuous loop around the body and through the pulleys. In a preferred embodiment the vertical distance between band and the pulleys attached to the suit is approximately 4 inches, however it may be more or less than this. The attachment pegs on the sides 120 provide a means for connecting the band to a supporting mechanism.

Figure 22:
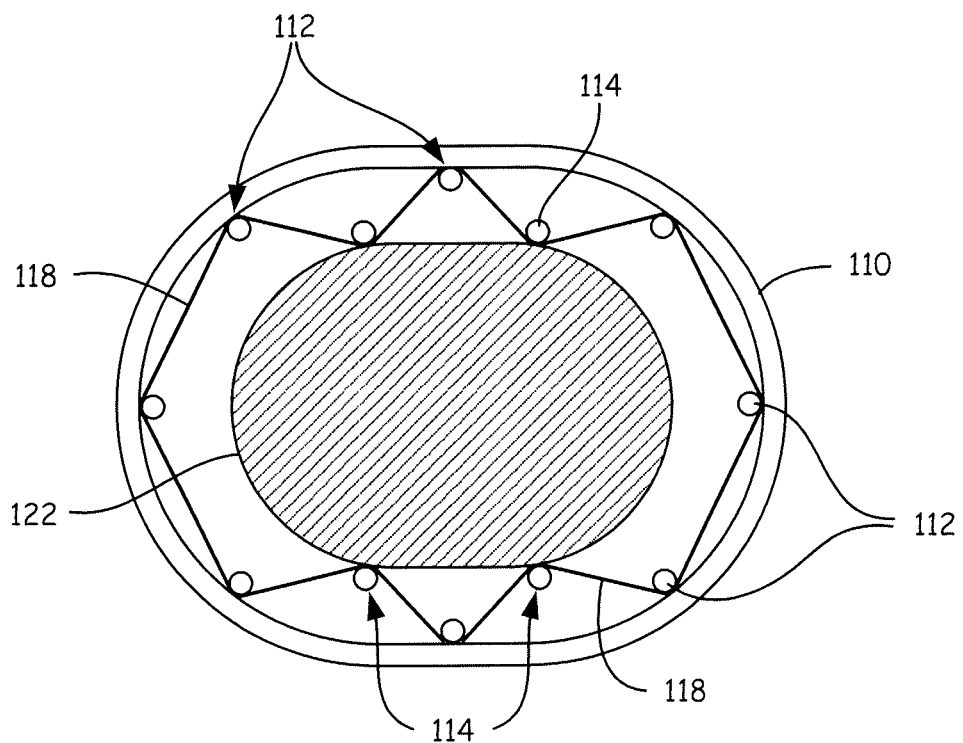
FIG. 22 is a top down cross-sectional view of the band and pulley attachment system of FIG. 21.

FIG. 22 shows a top-down cross-sectional view of the band 110 and pulley attachment system. The cross-section of the body at the waist 122 has a roughly oval shape. In a preferred embodiment the band is approximately oval in shape. In a preferred embodiment, the band is a continuous loop. It may also be hinged and fixed with a clasp to allow for easier doffing and donning. Pulleys 112 are attached to the band at spaced intervals. In a preferred embodiment, eight pulleys are attached to the band. In other embodiments four, six, eight, ten or twelve pulleys are attached. Another group of pulleys 114 are attached to a suit at spaced intervals. Each pulley attached to the lower body suit is positioned at approximately a midpoint between the pulleys on either side of it on the band. Each pulley attached to the body suit 14 is positioned to be at the middle between the pulleys on the band on either side of it. The cord 118 may also pass through several band pulleys in a row to maintain clearances of the cord and pulleys and the body during body movements. The cord may be comprised of either a low stretch material such as nylon or elastic material such as stretch cord.

Figure 23:
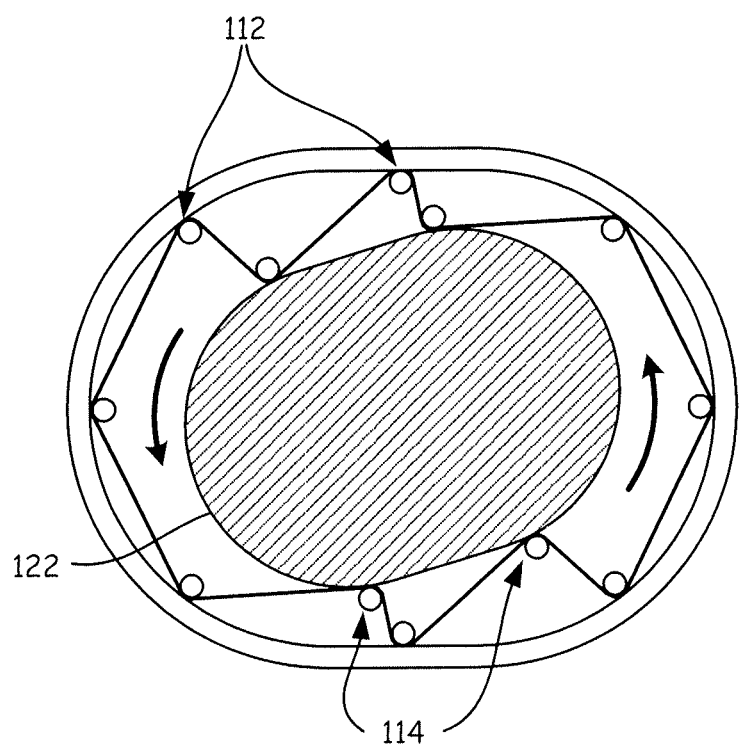
FIG. 23 is a top down cross-sectional view of the band and pulley attachment system of FIG. 21 with the person's lower body and hips rotated.

FIG. 23 shows a top view of the band and pulley attachment system when the lower body and hips have rotated counter-clockwise and the band has remained stationary. When the hips and lower body rotate as part of a normal running or walking, the pulleys on the body suit move along the connecting cord so that their positions change relative to the pulleys on the band. As shown in FIG. 23, as the body has rotated counter-clockwise, each pulley on the body suit 114 has moved along the cord to a new position so that it is closer to the pulley 112 on the band in the direction of rotation and further from the pulley 112 on the band that it is away from the direction of rotation.

Figure 24:
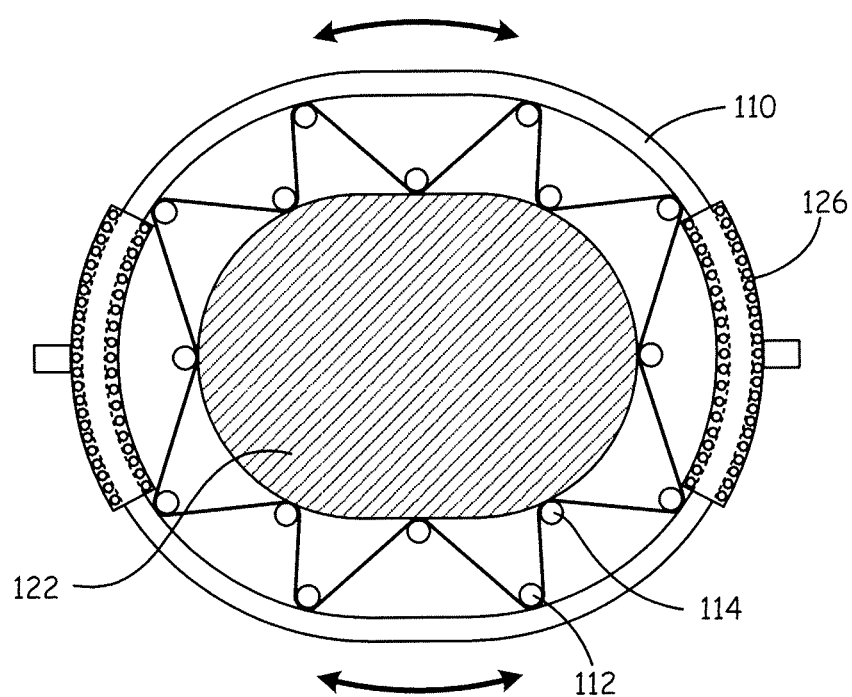
FIG. 24 is a top down cross-sectional view of the band and pulley attachment system of FIG. 21 having curved linear bearings.

FIG. 24 shows a top view of an embodiment of band and pulley attachment system in which curved linear bearings 126 are incorporated at the attachment points at the end. The band in this embodiment is circular in shape. The band is constructed with grooves that match with the curved linear bearing 126. This design allows for free rotation of the band about the superior-inferior axis (i.e. vertical axis) of the person. Other mechanisms that provide for rotary motion such as curved linear rails might also be utilized. Eight pulley's 112 are attached to the band at spaced intervals. The pulleys are attached at the bottom of the band so as to not interfere with bearings. The housing for the curved linear bearings goes over the top of the band. Another group of eight of pulleys 114 are attached to a suit at spaced intervals. Other numbers of pulleys may also be used such as four or six or ten or twelve.

Figure 25:
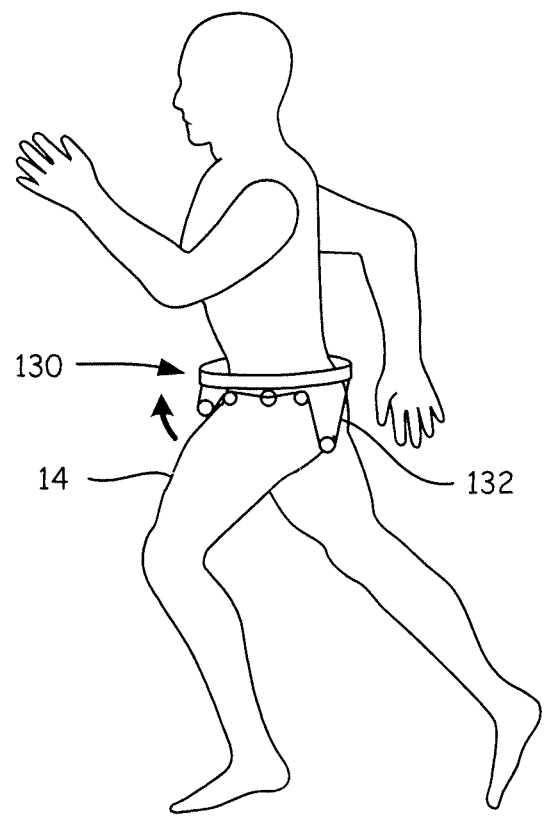
FIGS. 25 and 26 are perspective views showing the adjustment of the band and pulley attachment system to the motion of the person's leg about the hip during the running stride.
Figure 26:
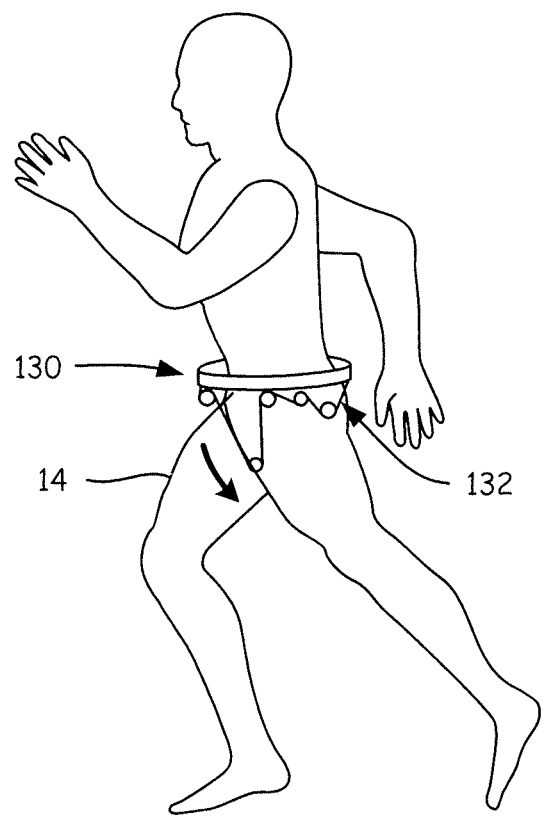

FIGS. 25 and 26 show the adjustments made by the system to the motion of the leg about the hip during a walking or running stride. During a walking or running gait cycle, the legs swing back and forth about a medio lateral axis through the hip joints as shown previously in FIG. 20. FIG. 25 shows the start of a gait cycle as the left leg is placed forward. The lengths of the cords connecting the band pulleys to the suit pulleys are denoted as left-front-cord-lengths 130 and left-rear-cord lengths 132. As the left leg is placed forward at the beginning of the stride, the left-front-cord-lengths shorten and the left-back-cord-lengths lengthen. FIG. 26 shows the change in cord lengths of the cords connecting to the left leg as the leg has moved backward. As the left leg is moves backwards at the end of the stride, the left-front-cord-lengths lengthen and the left-back-cord-lengths shorten. The tension in the cord remains the same throughout the gait cycle so that the system provides body weight support without constraining the back and forth movement of the legs about the hips.

Figure 27:
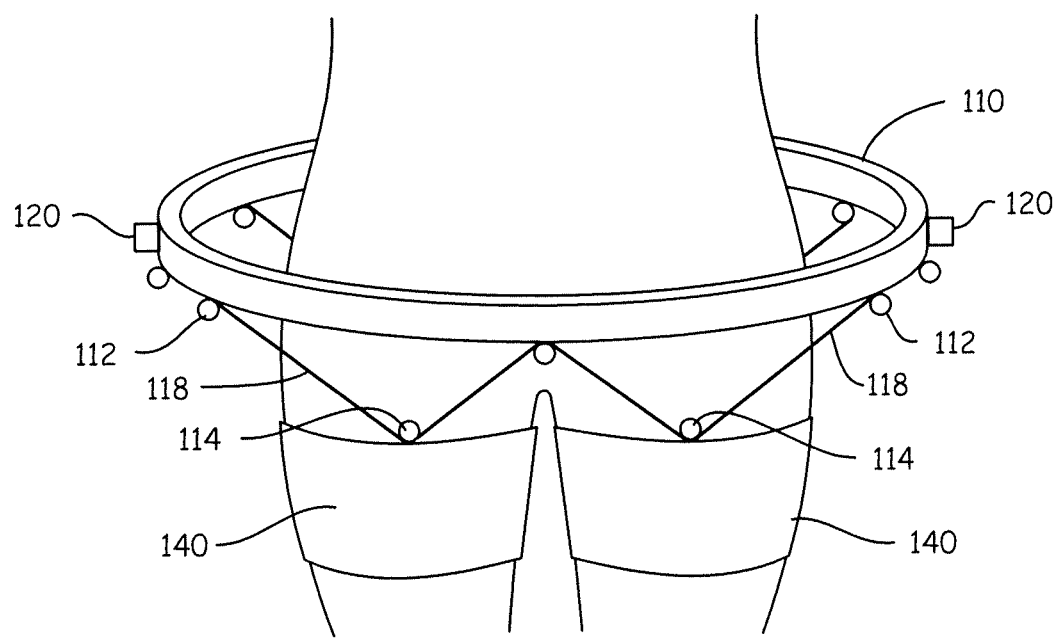
FIG. 27 is a perspective view of an alternative embodiment of the body weight support device featuring a leg harness.

FIG. 27 shows another embodiment of the invention in which the rigid band and pulley system is attached to a leg harness 140 on the lower body rather than a pressurized suit. The leg harness 140 consists of webbing straps that are attached to the person's legs. A suitable harness is constructed from nylon webbing. Velcro closures and nylon straps and buckles allow the harness to be adjusted to fit different body sizes. The harness may have padding and rigid or semi rigid areas to provide additional comfort. The rigid band and pulley and system are the same as previously described and shown in FIG. 21. In this embodiment, the pulleys 114 are attached to a harness at spaced intervals. Pulleys 112 are attached to the rigid band 110 at spaced intervals. A cord 118 runs through the pulleys. The device provides for unrestricted body movements along all body axes of rotation as previously described improving on existing harness systems.

In this manner, the rigid band and pulley system is used with the walker device as a support aid that can be used to assist the mobility of elderly or physically-impaired people undergoing rehabilitation, particularly those recuperating from leg or back injuries. The mobile walker provides body weight support using differential pressure suit is previously described in this application. Another use of the rigid band and pulley system on the mobile device is to provide stability for walking. If a person becomes unstable or loses balance, the pulleys and band inherently provide a counter force as the person tilts from vertical. The pulleys and band make it difficult or even impossible to fall. Falls are a major source of injury and death for the elderly and disabled population. The above-described wheeled walker is also advantageous for those impaired persons with limited or no use of their hands and arms because it does not require the use of their hands and arms for support as is necessary with a traditional walker. The support walker provides the necessary support and stability for that person instead of him having to resort to his arms and hands leaning on a conventional walker. The support aid may also be used to provide body weight support while both walking and running. This is an improved system for rehabilitating a skeletal joint injury, training for injury prevention, or assisting in physical therapy or gait therapy for the physically disabled.

Figure 28:
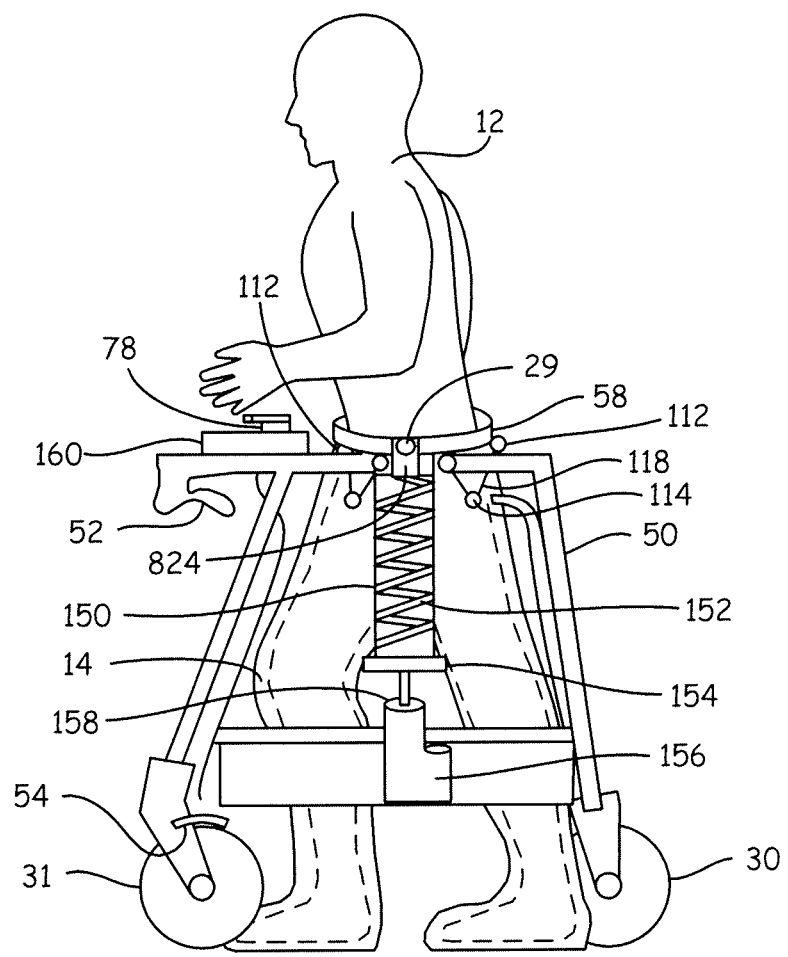
FIG. 28 is a perspective view of the rigid band and pulley system used to provide body weight support to a person on a powered four-wheeled support structure.

FIG. 28 shows in greater detail the incorporation of the rigid band and pulley system into the walker device 26 of FIG. 1. Like numbers have been used for the elements in common shown in the two drawing figures. This support aid utilizes a pressure suit 14 worn by a person, a powered air pressure source, and a powered constant-force adjustment mechanism. Various embodiments of the pressurized suit described earlier can be utilized with this wheeled support aid. The suit can be customized for easy entry and exit by physically impaired persons. A rigid band 58 encircles the lower body at approximately the waist. Pulleys 112 are connected to the band at intervals around the band. Other similar pulleys 114 are connected to a lower body suit at intervals. A cord 118 runs through the pulleys on the band and the pulleys on the suit. The cord alternates passing through a pulley on the band and a pulley on the suit. The ends of the cord are connected together so that it forms a continuous loop around the waist through all the pulleys. The cord and pulleys thus connect the suit to the rigid band. The band is connected to a constant-force adjusting mechanism 150 mounted on each side of the support device. The band is attached to the constant-force adjustment mechanism using an attachment latch. The attachment latch can be either a manually opened and closed latch or automatic coupling latch such that the band is easily attached or detached from the c-shaped horizontal support bar. The latch can be such that the band may rotate or pivot about the attachment point.

The constant-force adjustment mechanism control system and user interface may be similar to the constant-force adjustment mechanism previously described in this application. In the embodiment described herein, compression springs (Century Spring) 152 that yield about 50 pounds for 6 inches of compression are utilized to provide the constant force. Gear motors that displace the springs were used. Other mechanisms that provide a relatively constant force such as constant force air springs might also be utilized in place of the compression springs.

The preferred method of an adjustable compression spring will be described. It is important over small vertical displacements in the range of a typical walker (nominally 1-3 inches) that the counter force is maintained without great variability. Thus a spring constant of only a few pounds per inch is used such that force when the spring is compressed changes only modestly when the individual rises slightly during walking.

At the end of compression spring 152 is an electronic load cell 154 capable of measuring the desired compression from 0 to 100 pounds. Mounted on the bottom side of the compression spring is a gear motor 156 and displacement shaft 158. The motor has a displacement encoder that is fed to the system microcontroller, along with the load cell information. In this embodiment, the user selects two parameters from the input box 160 rotary dials: desired un-weighting level in pounds and a setting that relates to the cross sectional area of the individual. In the preferred embodiment of the input dial, this dial is labeled a 'comfort' setting, and individual users select a value that they determine in practice gives them a balance between the net downward force supplied by the pants air pressure, and the upward force on the pants supplied by the counter-tensioning system. A higher 'comfort' number will yield a higher pressure for a given un-weighting value, and would be necessary for thinner individuals. Conversely, a lower 'comfort' number would yield lower pressure for a given un-weighting value and would be needed for larger individuals. These comfort numbers 1-16 are simply mapped into cross-sectional area values in the control software, such that the following equation is maintained: $Wu=P*A$, where $Wu$ is the desired unweighting value, $P$ is the air pressure, and $A$ is the cross sectional area derived from the comfort dial setting. With $Wu$ and $A$ effectively chosen by the user, the appropriate pressure $P$ to support the un-weighting value is solved for.

Upon startup, the unweighting is not realized all at once, but can only happen as fast as the pants become pressurized, which in the described system requires on the order of 10 to 20 seconds. The counter-tensioning value, supplied by engaging the gear motor to begin compressing the compression springs, is developed at a rate such that the above equation is maintained dynamically, within a 5 pound limit. A 24 lead acid battery source is used to power a portable air pump (Thomas), an air regulator (Bellofram), the gear motor, load cell and pressure sensors, and an electronics PLC controller (Galil Inc). In the preferred control algorithm during build up to a target unweighting value, the load cells and pants pressure are read every 50 milliseconds, and if the above equation, due to increasing pressure can support a further increment of unweighting, the gear motor is engaged for a short increment. Air flow continues until the desired target air pressure is reached, and every few milliseconds further force is applied to the springs such that when the air pressure target is reached, the counter-tensioning value is simultaneously reached. The same lock step algorithm is engaged if the un-weighting set value is changed, or dropped to zero.

A further enhancing mechanism particularly for disabled individuals desiring to walk in the system is power assisted wheels. A phenomenon when one is greatly unweighted by the disclosed walker system, is that one has less 'leaning' ability to nudge the walker into motion, simply because one effectively weighs less. Normal individuals can easily overcome this by pushing with their arms and legs, but the addition of power-assisted wheels are a useful enhancement for frail or rehabilitating individuals. The mechanism is realized by an electric motor and clutch on each of the front two wheels that supply a significant fraction of the force necessary to overcome friction and roll the walker. The motor need not run full time but is engaged with a hand switch on the walker to conserve battery power. This also serves as an optional braking mechanism, in that if the engagement switch is released, the wheels may brake. The clutch mechanism allows users to exceed or overdrive the force supplied by the motor to the extent that they are capable of exceeding the very minimal startup speed supplied by the wheel motors.

Figure 29:
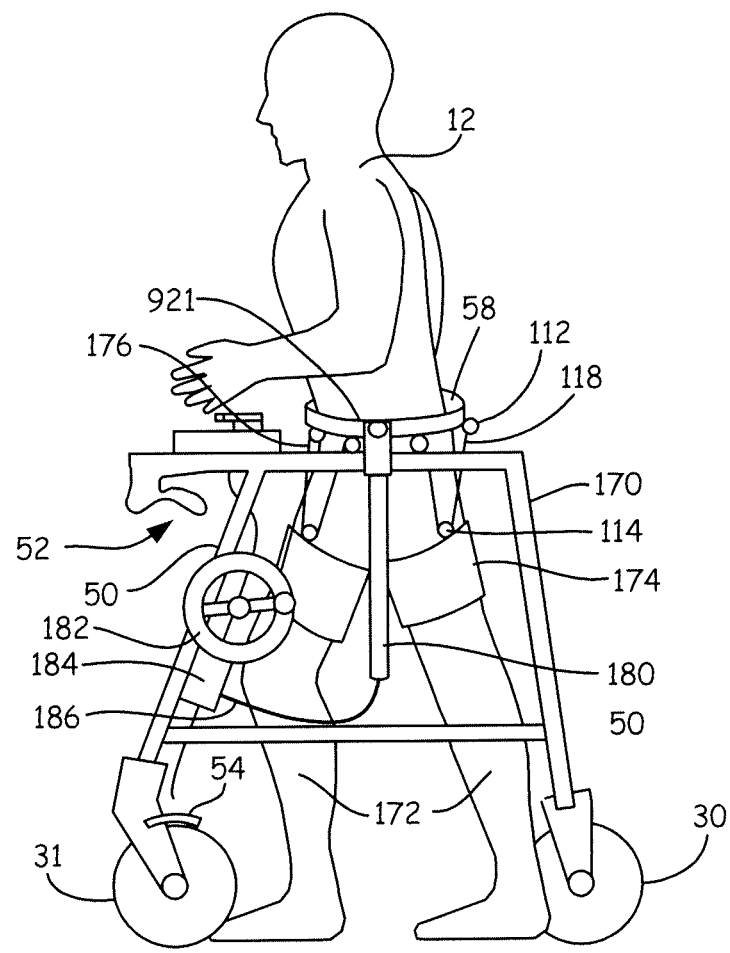
FIG. 29 is a perspective view of the rigid band and pulley system used to provide body weight support to a person on a non-powered, manually-operated four-wheeled support structure.

FIG. 29 shows an embodiment of the rigid band and pulley system used to provide body weight support on a non-powered, manually-operated four-wheeled support walker 170. A leg harness 172 is worn by the person 12 in this embodiment. In other embodiments, a pressurized or non-pressurized suit may be utilized. The harness consists of bands 174 on the legs of the person 12 and is constructed as described previously. The rigid band and pulley system 176 attached to a harness on the legs of the person. This particular embodiment of a wheeled support aid does not require a powered source for pressurized air or a powered constant-force adjustment mechanism. Some advantages of a non-powered, mobile support aid are to provide stability and body weight support are lighter weight, ease of use and lower cost. In this embodiment an elastic cord 118 that runs through the pulleys attached to the band and harness is utilized as a constant force adjustment system. The tension in the cord is manually adjusted by raising or lowering the rigid band. Hydraulic cylinders 180 are attached to each side of the wheeled support aid. The rod end of the hydraulic cylinder is attached to the band by an attachment latch. The attachment latch can be either a manually opened and closed latch or automatic coupling latch such that the band is easily attached or detached from the c-shaped horizontal support bar. The latch can be such that the band may rotate or pivot about the attachment point. The band is raised or lowered by turning a crank 182 that is operated by a hydraulic pump 184. The pump is connected to the hydraulic cylinder by a hydraulic line 186. Other mechanical means of raising and lowering the band might also be utilized in other embodiments. The tension in the band might also be adjusted by lengthening or shorting the elastic cord which runs through the pulleys. The ends of the elastic cord may be connected to each other by a means which allows for easy adjustment. The walker may also be utilized in a mode without a constant-force adjustment mechanism by utilizing a non-elastic cord.

Both the powered and non-powered mobile support aids that utilize the band and pulley suspension system can utilize a pressurized suit, a non-pressurized suit or a harness. The powered mobile support aid's frame 50 and front wheels 31 and rear wheels 30 are designed and sized so that the mobile unit has the functionality of standard wheeled walkers. Similarly, the non-powered mobile support aid's frame 50 and front wheels 31 and rear wheels 30 are designed and sized so that the mobile unit has the functionality of standard wheeled walkers. The front wheels turn and pivot to allow for easy turning. All four wheels may also turn and pivot. Typically the wheels are at least seven inches in diameter—preferably eight inches—to ensure better reliability. Various numbers of and configurations of wheels may also be utilized including configurations with three, five, six or more as in known in the art. The wheels may be combinations of fixed or pivot wheels and may be of different sizes and configurations as is known in the art. The number, size, type and configuration of wheels provides for various handling, maneuverability and stability characteristics required for various therapeutic uses. The wheels may be connected to a steering mechanism, so the person or a person assisting him may manually steer the wheeled support aid. Moreover, to enhance the safety, convenience, and durability of a wheeled walking aid and its parts, the wheeled support aid may utilize tubular seats, back seats, and baskets with spacers and cushions.

The powered wheeled support aid can be incorporated with hand-operated brake levers 52 and brakes 54. Similarly the non-powered wheeled support aid can be incorporated with hand-operated brake levers 52 and brakes 54. The brakes on the wheeled support aid may constitute locking brakes to allow the person to stand while supported in a stationary position. Other means of braking may be provided for those with limited use of their arms and hands. The wheeled support aid can be designed to enable greater range for rotating the body from side to side to enable the person in the wheeled support aid to turn from side to side and stand facing one side or the other, or even the back. It may also have a seat that will allow for resting. The wheeled support aid can have adjustable height mechanism to accommodate various sizes of persons. The wheeled support aid may also be designed with a folding mechanism for compact storage.

The wheeled walker support aid can feature hand supports for assisting the entry and exit from the support aid. The wheeled walker support aid can be constructed from lightweight materials such as aluminum or composites. The wheeled walker support aid may preferably use tubular seats, back seats and baskets with spacers and cushions.

As discussed above, elderly or physically-impaired people undergoing rehabilitation, or people suffering from gait and balance problems due to strokes, Parkinson's disease, and other neurological disorders, or people requiring hospitalization, or recovering from illness or surgery often lack the strength and balance to rise from a sitting to a standing position. Nurses, physical therapists, aids, and other care providers often have to assist in standing and walking. Assisting large persons in standing and walking requires significant physical strength and sometimes requires several people. Furthermore, there is a risk of falls to the patient or harm to the care provider from heavy lifting. Thus, the present invention provides a lift-assisted mobility device that provides both body weight support and lift assistance. It functions to off-load a portion or all of the person's body weight in order to make it easier for him to rise from a sitting position to a standing position.

Figure 30:
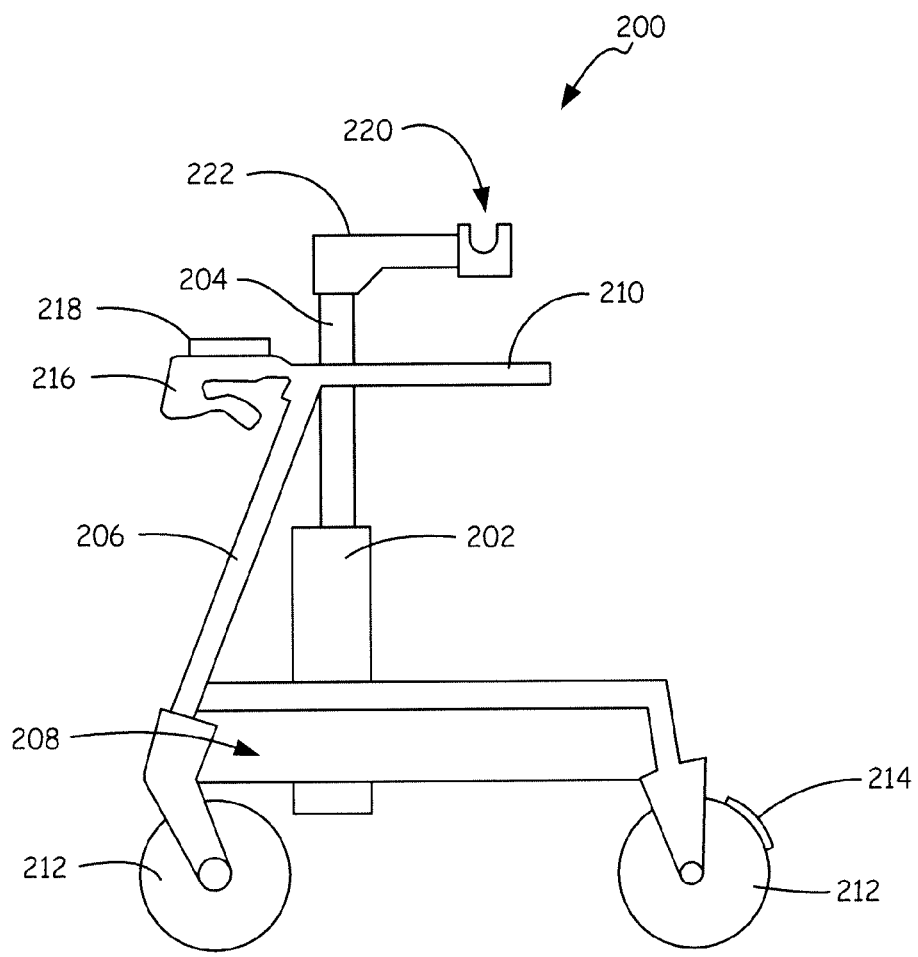
FIG. 30 is a side view of a lift-assisted mobility device of the present invention.

A preferred embodiment of the lift-assisted mobility device 200 is shown in FIG. 30. The lift-assisted mobility device utilizes a constant-force adjustment mechanism 202. This mechanism provides a counter-force to support the vertical downwards load from a differential pressure suit as previously described. The constant-force adjustment mechanism control system and user interface may be similar to the constant-force adjustment mechanisms previously described in this Application. In a preferred embodiment, the constant-force adjustment mechanism 202 is an air cylinder. An air cylinder provides both a constant force and a sufficient range of travel to accommodate the vertical displacement involved in moving from a sitting to a standing position. In other embodiments, the constant-force adjustment mechanism may utilize air springs or mechanical springs, as is known in the art. The constant-force adjustment mechanism may also comprise mechanical springs or pneumatic springs, air cylinders, or air springs that are not constant force. In another embodiment, the constant-force adjustment mechanism may consist of a compression spring, electronic load cell, gear motor and displacement shaft as previously described. A vertical shaft 204 extends from the constant-force adjustment mechanism. The vertical shaft of the constant force adjustment mechanism 202 is sufficiently long to provide a constant load as the person rises from a sitting position to a standing position.

As shown more clearly in FIG. 30, a support frame 206 extends from the base of the device 208 on the right side of the device. The left side of the device is open and without a supporting frame member to enable the base 208 to fit under a chair or bed. A handrail 210 is provided. The lift-assisted mobility device 200 is accompanied by wheels 212 and brakes 214 that are hand-operated and may be power assisted. The brakes may be operated using the hand brake levers 216, or from the control panel 218. The brakes may also be used to lock the wheels to stabilize the lifted assisted mobility aid. The base 208 houses a power supply, compressed air supply, batteries and controls (all not shown).

Figure 31:
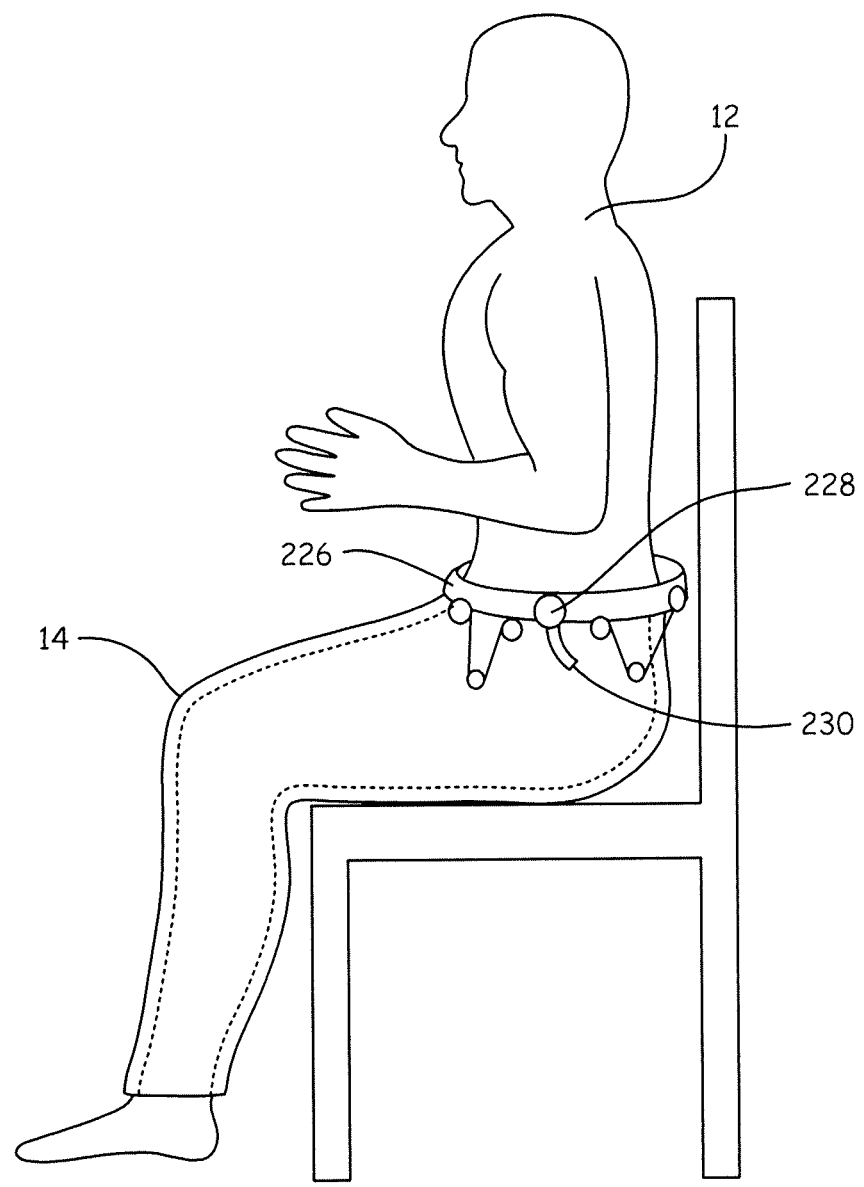
FIG. 31 is a side view of a person wearing a pressurized suit and band and pulley system of the present invention.

A latch 220 is connected to the end of a horizontal support bar 222 that extends from the top end of the vertical shaft 204. The latch 220 couples with a rigid band and pulley system 226, as shown in FIG. 31. The construction and function of the band and pulley system are as previously described in this application. In the present embodiment, the latch 220 is an electro-mechanical latch. It can also be a manually-operated latch. The latch can be electronically coupled and decoupled via the control system. In an emergency, the person can be quickly detached from the device. It has an electronic interconnect sensor, so that the device can be enabled only when the connection is secure. A manual lease is also provided. The attachment latch also contains a coupling for an air supply hose. An air supply hose (not shown) and electronic connections (not shown) are integrated internally in the horizontal bar 222, vertical shaft 204, constant force mechanism 202 and extend to the air supply and controls in the base 208. An air connection (not shown) in the latch couples with an air connection on the rigid band and pulley system (also not shown).

FIG. 31 shows a seated person 12 wearing a differential pressure suit 14 connected to a band and pulley system 226. In this embodiment, the band and pulley system and suit are integrated together as a single garment so that a person is able to simple doff or don the entire unit. They maybe also separate components which can be attached together as needed. Coverings may be applied so that the band and pulleys so the mechanisms are not obtrusive and don't interfere with doffing and donning.

The differential pressurized suit 14 shown in FIG. 31 comprises a full-length lower body suit that extends from the waist to above the ankles. The suit is sealed at ankles and the waist. Alternatively, the suit may extend from the waist to cover the feet, or only extend from the waist to the knees, or upper thigh as described in this Application. The seal may constitute any of the sealing methods described in this Application, including a neoprene band, an inflatable tube, or an inflatable bladder. The rigid band has a coupler 228 which mates with the latch mechanism 220 on the lift assisted mobility device 200. An air hose 230 is connected to the coupler 228 and the differential pressure suit 14.

Other embodiments of the lift-assisted mobility device can utilize a non-pressurized body suit, or a harness assembly rather than a pressurized differential pressure suit. For example, the band and pulley system of the lift-assisted mobility device may be attached to a leg harness 172 as shown in FIG. 29. The harness consists of bands on the legs of the person and is constructed as described previously. The rigid band and pulley system attaches to a harness on the legs of the person. In another embodiment, a non-pressurized suit may be utilized. The non-pressurized suit can be constructed as previously described for pressurized suits with the exception that seals and air supply and connections are not provided or necessary. These embodiments are generally utilized where a lesser amount of body weight support is needed.

Figure 32:
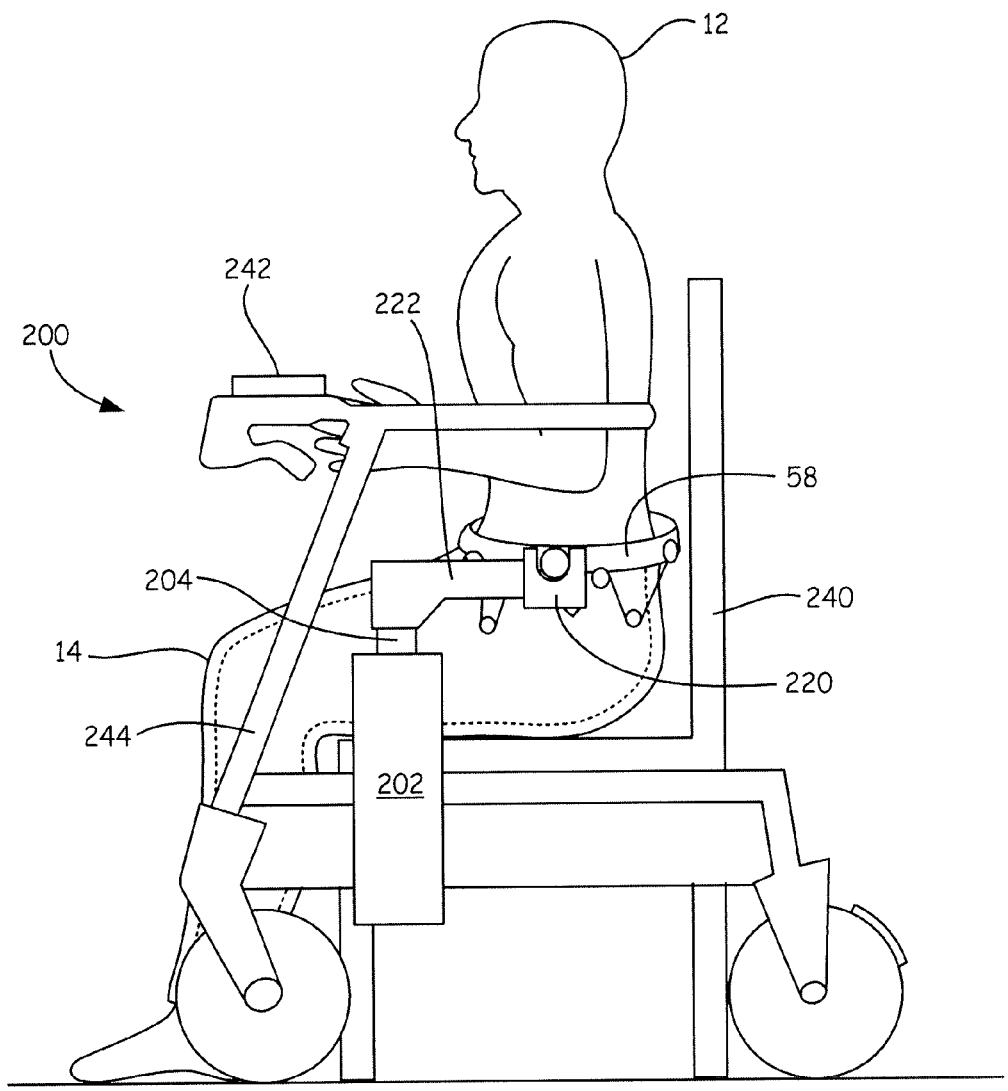
FIG. 32 is a side view of a person wearing the pressurized suit with the band and pulley system operatively attached to the lift-assisted mobility device in a seated position.

FIG. 32 shows the lift-assisted mobility device 200 in place adjacent to and connected to the band pulley system and differential pressure suit of a person seated on a chair 240. The vertical shaft 204 and horizontal bar 222 are at a low position, so that the level of the latch 220 is at the level of the band and pulley system. The person or a therapist may use the control panel 242 to activate the device and set the amount of body weight support. A control system as previously described in this Application provides the correct air pressure to the pants, and operates the constant-force adjustment mechanism to off-load the selected amount of body weight support. Once the system has reached the selected level of body weight support, the person may then stand easily with reduced or even minimal effort, and without needing the assistance of a caregiver. Once standing, the person may then use the device as mobility assist device with body weight support.

Figure 33:
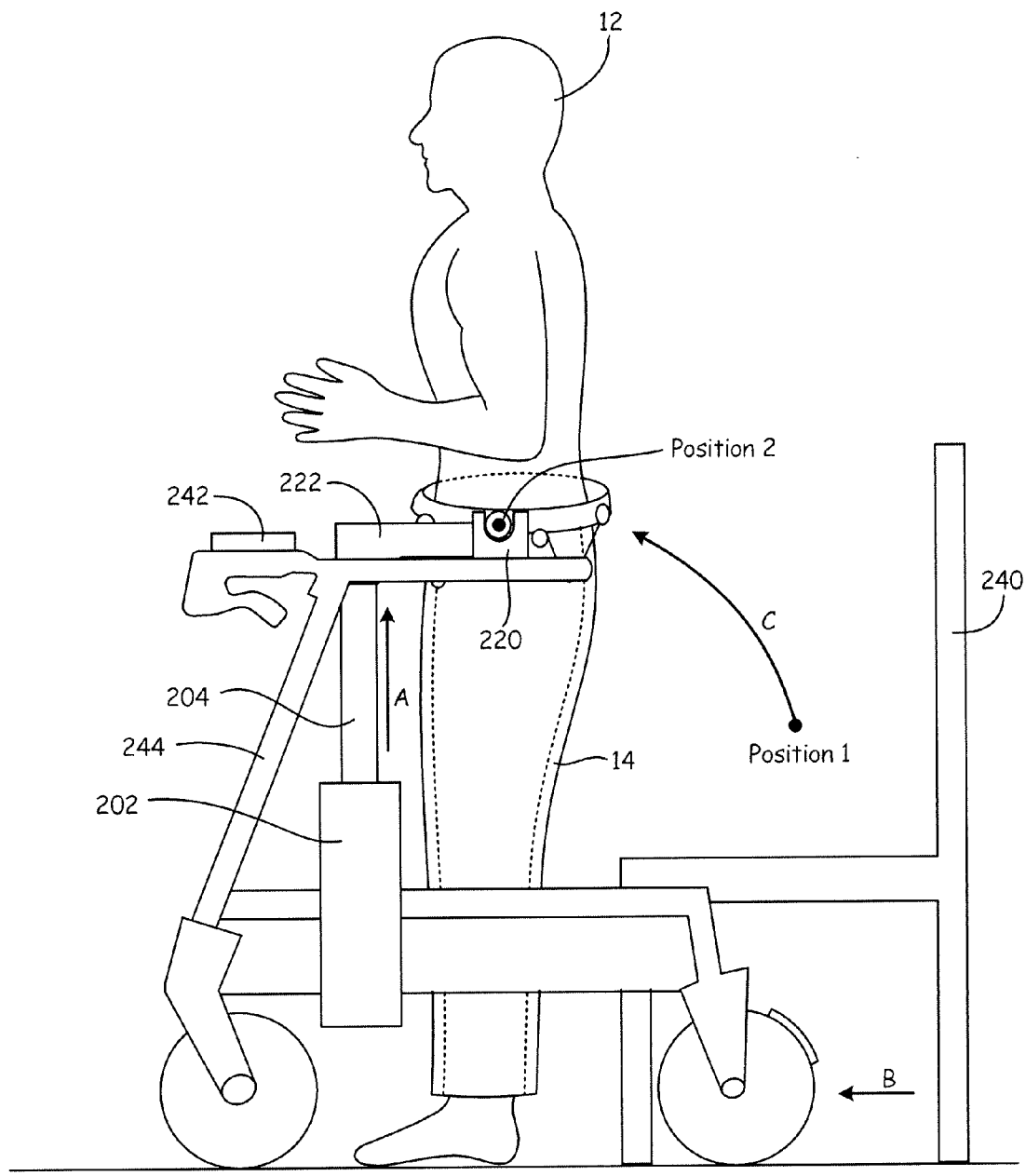
FIG. 33 is a side view of the person operatively attached to the lift-assisted mobility device of FIG. 63 in the standing position.

FIG. 33 shows the person 1701 having moved to a standing position. The person's center of mass is approximately at the position of the latch 220. As the person rises from the chair 240, the center of mass moves both vertically and horizontally in the motion shown by Arrow C. The device accommodates this motion, while providing a constant uplifting force to unweight the person. The arrows in the drawing show the directions of travel of various components. First the vertical shaft moves upwards as the person rises, as shown by Arrow A. The constant-force adjustment mechanism 202 moves the vertical shaft upwards and provides a constant force. The entire device also moves forwards horizontally, as indicated by Arrow B. The wheels allow the unit to move horizontally as the person stands up. This horizontal motion of the device allows the device to stay centered with the center of mass of the person providing safety and preventing falls. The person is able to safely rise to a standing position with minimal effort and immediately began walking with reduced weight.

In some rehabilitation settings, there are advantages to being able to use a mobile support device in stationary mode in conjunction with a treadmill. For example, in traumatic brain injury patients, the added stimulation of ambulating about the rehabilitation facility may be overwhelming, making the fixed treadmill setting desirable, or a physical therapist may need to remain in a seated position to access the patient's legs while the patient ambulates. It will also be economical to be able to utilize a hospital's mobile support device on a standard treadmill, rather than purchasing a separate overhead harness system for treadmill-based therapy.

Figure 34:
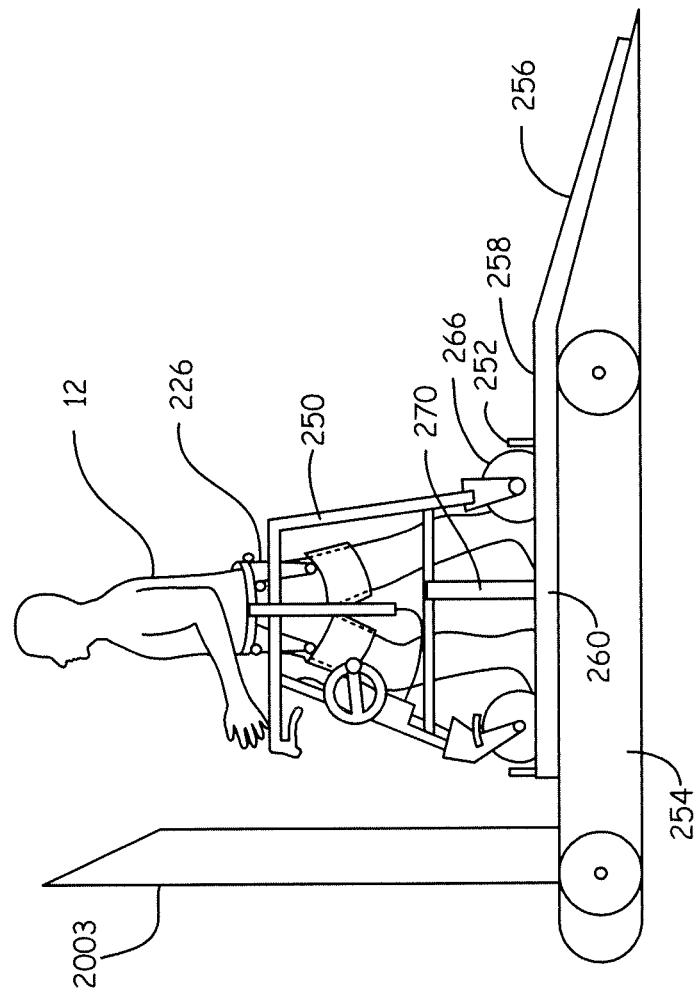
FIG. 34 is a side view of the person operatively attached to the lift-assisted mobility device in the standing position of FIG. 33 secured to a moving treadmill.

A means of mounting a mobile support device (walker) on a stationary treadmill frame is shown in FIG. 34. The patient 12 is shown using a walker 250 situated in a mount 252 on a treadmill 254. The mount consists of an incline platform 256 section utilized to roll the walker up onto the horizontal frame 258 section of the mount. The horizontal frame sections rest on each side of the treadmill 254 on the solid portion of the treadmill that is separate from the moving track 260 shown in FIG. 34.

Figure 35:
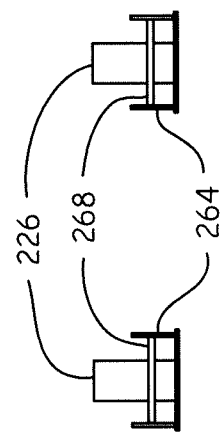
FIG. 35 is a view of the means used to secure the wheels of the lift-assisted mobility device in place to the treadmill.

A rear view of the mounting system of the treadmill-walker system is shown in FIG. 35. The horizontal frame section 258 has U-shaped channels 264 that are located at the left and right sides of the treadmill on the surface that is separate from the moving track 260. The U-shaped channels 264 serve as tracks that the wheels 266 travel in, thereby preventing lateral movement of the walker. Cross pins 268 are placed across the channels 264 once the walker is in place, behind the rear wheels 266 and in front of the front wheels (not shown) to prevent any forward or backward movement of the walker 1902. Clamp member 270 shown FIG. 34 connects from the treadmill mount to a cross member of the walker, and prevents any vertical movement of the walker, thereby enhancing stability. Thus, the walker is fixed in place, and the patient 12 is engaged in the walker as previously described in this Application. The patient 12 may then be unweighted as previously disclosed, and may walk at the desired treadmill speed as required for therapy.

Figure 36:
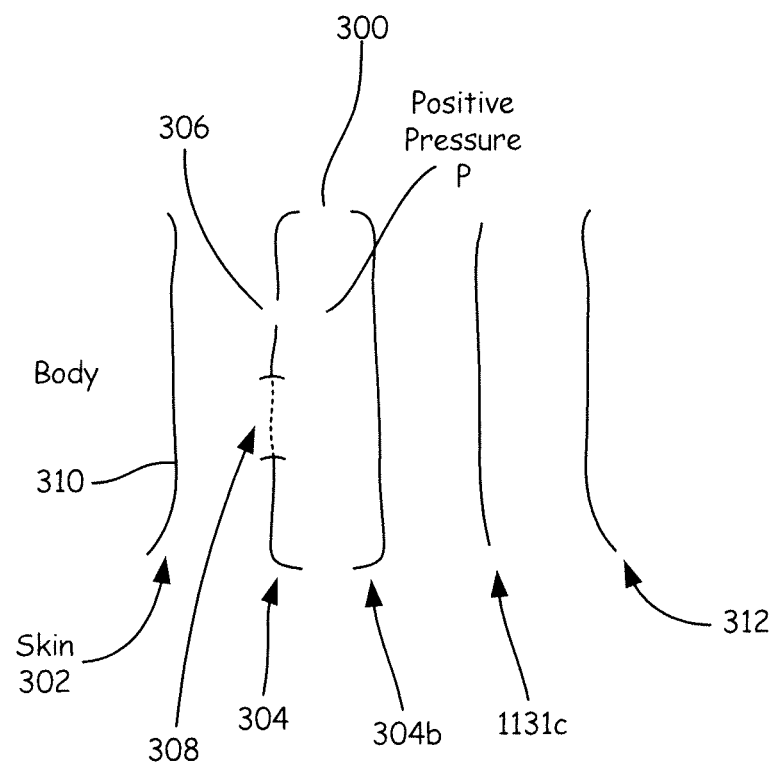
FIG. 36 is a schematic view of the layers of the close-fitting differential pressure body suit.

An improved embodiment of the close fitting differential pressure suit is described below. A construction of the layers of embodiment is shown in FIG. 36. An air-tight inner bladder 300 maintains the positive pressure P condition inside the suit against the person's body skin 302. The bladder consists of two layers, an inner layer 304 and an outer layer 304*b*. The fabric for the bladder may be formed from any pressure-tight material that is also sufficiently flexible to afford mobility by the person. Preferably the fabric consists of a material that is air impermeable and moisture vapor permeable. An example bladder fabric is TC92 a four-way stretch polyurethane coated fabric available from Dartex coatings 22 Steel Street, PO Box 70 RI. This both allows the bladder to maintain a positive air pressure P and allows moisture vapor from sweat to permeate through the material to keep the person dry and comfortable. The bladder may also be constructed to have holes 306 that are permeable to air on the inner side next to the skin. The bladder may also be constructed to have sections of another material 308 that are permeable to air on the inner side next to the skin. This allows for air to circulate between the bladder and the skin. A continuous supply of pressurized air can be supplied from a pressure source and pressure control system as described in this application. The pressure system can be sized to provide the required amount of air flow to maintain cooling. Outer layers 310 and 312 of the differential pressurized suit 14 composition prevent the suit from expanding due to the force applied by positive pressure P, while maintaining the shape of the suit to fit closely to the body.

The bladder can be sized to the same size as the outer constraining layers 310 and 312, or it maybe sized to be smaller or larger than the outer constraining layers. The bladder can be sized to extend various lengths up the waist of the suit, so that positive pressure is applied only in sections that the bladder extends to beneath the constraining layers. The bladder can extend upwards from the legs just to the hips, or just to approximately the pelvic area, or all the way to the waist. The bladder may be patterned so that it conforms to zippers incorporated into the suit. The bladder may be constructed from identically sized sections of fabric, so that one section forms an inner layer 304 and one section forms the outer layer 304b or the bladder. The bladder may be constructed by sewing the sections together with a heat sealing film at the seams to make an airproof seam. One suitable heat-seal film is Bemis 3218 adhesive film available from Bemis 100 Ayer Rd—Shirley, Mass. 01464 USA.

The fabric for these first and second outer constraining layers 310 and 312 should be composed two way stretch fabric. This type of fabric is constructed to mostly be non-extending along one axis, and elastic or extensible along a second axis perpendicular to the first axis. Exemplary two-way stretch materials include, without limitation, nylon-Lycra that can be knit or braided, or a monofilament like nylon or Dacron. Two-way stretch fabrics are available from Shoeller Textile USA of Seattle, Wash.

Figure 37:
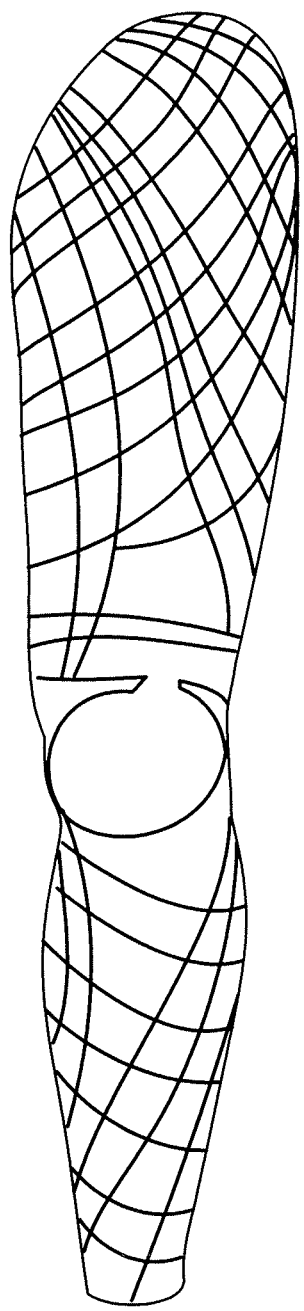
FIG. 37 is a view of the mapping lines of non-extension on a lower body.

The fabric can be more specifically oriented so that its non-extending axis follows lines on the body in which the skin does not stretch or extend during bending or other movement. These lines are known within the industry as "lines-of-non-extension." The concept of lines of non-extension is described in a published technical report: THE USE OF LINES OF NONEXTENSION TO IMPROVE MOBILITY IN FULL-PRESSURE SUITS, ARTHUR S. IBEIALL, RAND DEVELOPMENT CORPORATION, AMRL-TR-64-118. AMRL-TR-64-118. Lines-of-non-extension represent directions on the skin of the body in which the skin does not stretch or extend. A picture from the report which maps the lines of non-extension on a mannequin is shown in FIG. 37. There are two sets of lines-of-non-extension on the lower body shown in FIG. 37. One set runs roughly perpendicular to the longitudinal axis of the body, while the second set runs roughly parallel to the longitudinal axis of the body.

The constructions of the two outside layers 310 and 312 are such that the stretch and non-stretch directions of the fabric are mapped into the lines-of-non-extension as best as possible. This is accomplished by constructing the suit of multiple sections of two-way stretch fabric in a pattern which maps the non-stretch direction of the individual fabric sections onto the lines of non-extension as best possible.

Figure 38:
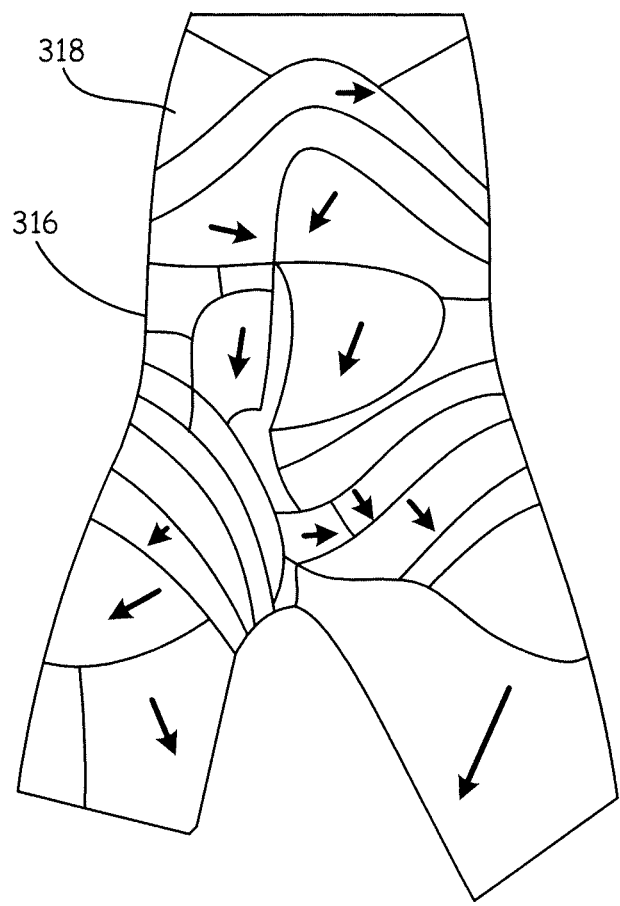
FIG. 38 is a view of a pattern for the first outer layer of the body suit.

A pattern 316 for the first outer layer 310 is shown in FIG. 38. The arrows indicate the direction of stretch. The individual sections of fabric are indicated by the sections, for example 318, shown in the pattern. Lines indicate where seams are sewn between the pieces. The individual layers are sewn together at the seams and the outer edges are sewn together to form a suit. The same method is applied to the outer layer 312. The first outer layer 310, second outer layer 312, and sealed bladder are sewn together to form a single lower body suit. Zippers may be incorporated in the design to facilitate donning and doffing of the suit. In particular zippers may be incorporated from crotch area (to the waist) and at the calves as in common in pants and close fitting tights designs. Generally, the first outer layer 310 serves to prevent the suit from expanding, generally circumferentially, due to pressure inside the suit. The second outer layer 312 prevents the suit from expanding, generally, longitudinally.

The suit also can incorporate sections of four-way stretch fabric as necessary in areas that require stretch in both directions. Where appropriate in sections of the body which do not stretch as much, such as the thigh area or lower calves, cloth, mesh, or net material that is non-extendible along both axes may be used.

The suit 300 may have a lacing system. The lacing system facilitates closely fitting the suit to various body shapes and sizes. The lacing system has unique features that enable it to work for long lengths including the length of the entire suit. The lacing system consists of low friction components. Nylon coated boot hooks are used in the lacing system. Military spec known as "Nato Hooks" are utilized for the low friction hooks. Low friction high strength cords are utilized. Exemplary line is Laser Pro Gold 300 lb test line available from The Kite Shop at.thekiteshoppe.com.

While the suit is described above as having multiple layers of fabric including air impermeable and two way stretch fabrics orientated and located as described, the functions of these various layers can be combined into fewer layers of fabric so that at a minimum the suit is comprised of a single layer of fabric with the functionality of the layers combined. For instance, two-way stretch fabrics that is also air impermeable and or water vapor permeable can be utilized to both contain pressurized air and constrain the suit as a single function. Or two or more layers of fabric can be laminated together so that the fabric consists of a single layer with the functionality of the individual layers.

Figure 39:
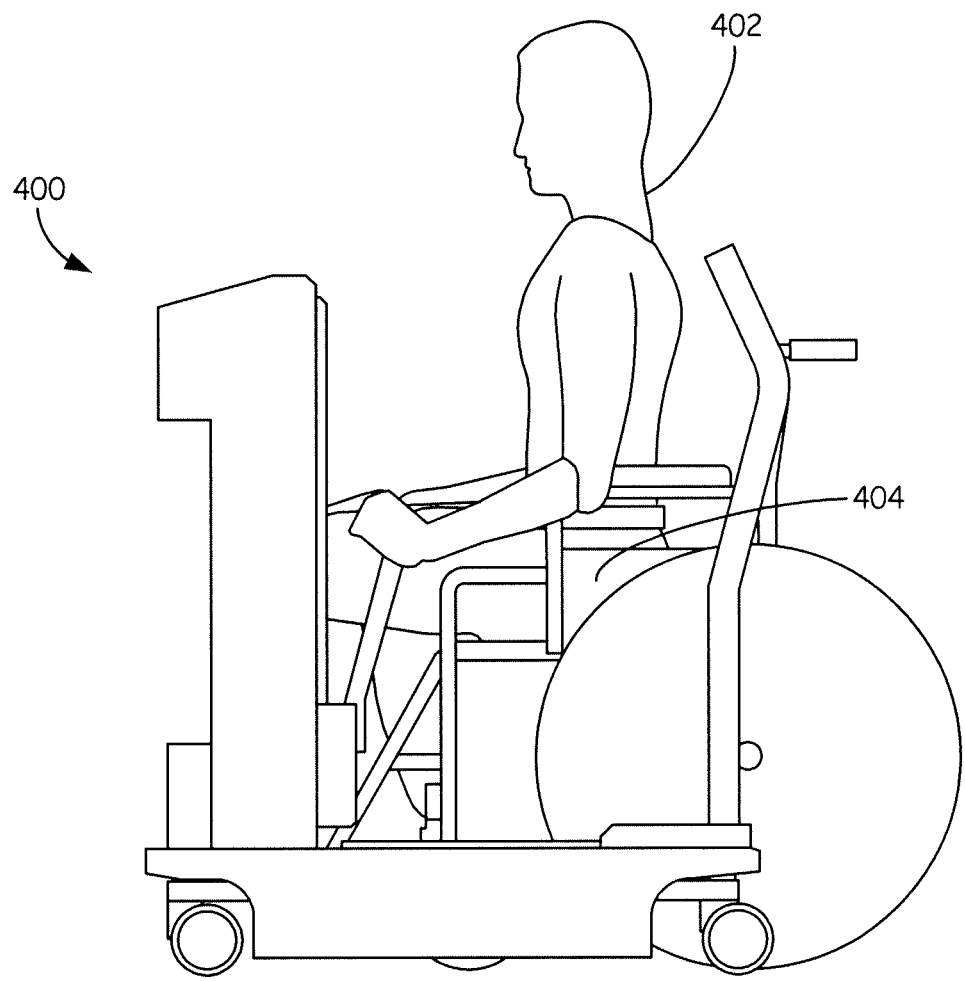
FIG. 39 is a perspective view of the body lift-assist walker device of the present invention with a patient in a wheel chair attached thereto for assistance with the sit-to-stand motion.
Figure 40:
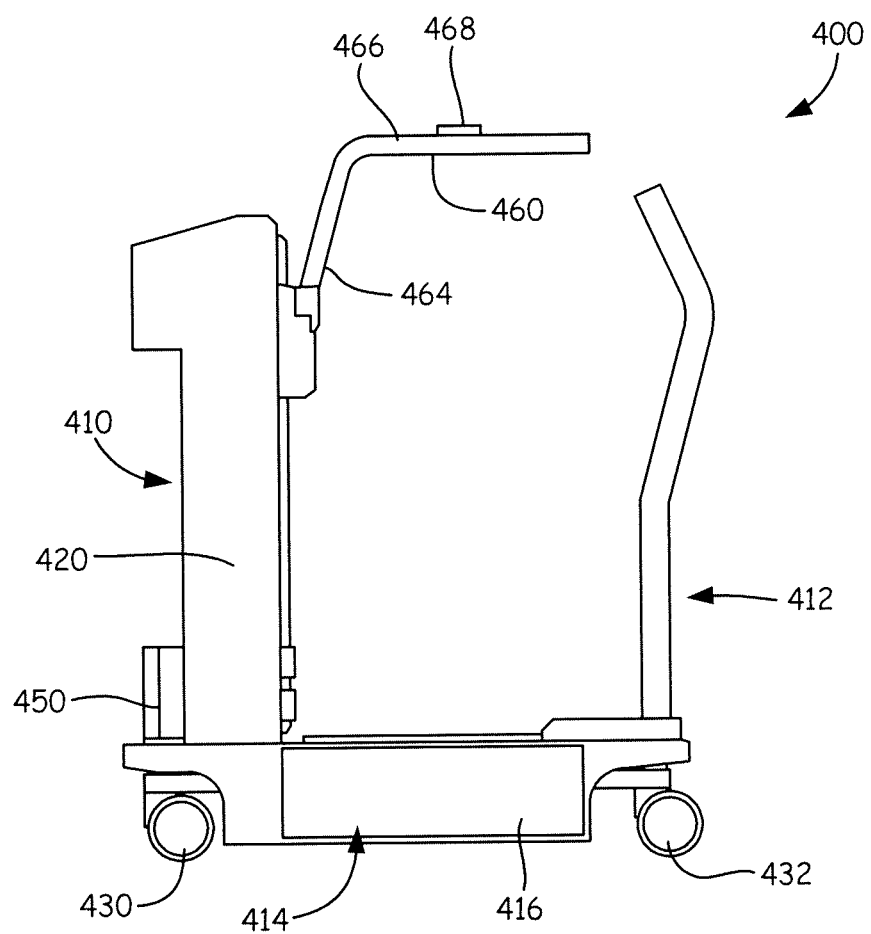
FIG. 40 is a left-side elevation view of the body lift-assist walker device of the present invention.

A preferred embodiment of the body lift-assist walker device 400 of the present invention is shown in FIG. 39 with a patient 402 sitting in a wheel chair 404 operatively engaged with the device. The body lift-assist walker device 400, itself, is shown in side view in FIG. 40, top plan view in FIG. 41, and perspective rear view in FIG. 42.

The body lift-assist walker device 400 has a front end 410 and back end 412 and symmetrical right and left sides 414. The frame of the device consists of left base unit 416 and right base unit 418 to which are vertically mounted left and right frame uprights 420 and 422, respectively. Connected horizontally to the left frame upright 420 and right frame upright 422 is crossbar 424. The crossbar 424 is located at a sufficient height so as to provide open frontal area 426 that does not interfere with a patient's legs as the patient swings his legs forward while walking. A preferred height for the bottom surface 425 of the crossbar 424 is 32 inches. It is preferable that the overall height of the device be similar to that of an ordinary walker in order to provide a compact design, and to enable the therapist to have access to the front of the patient. A preferred height for the top surface 428 of the crossbar 424 is 40 inches.

Mounted to the bottom of left base 416 are front caster 430 and rear caster 432. Similarly, front caster 434 and rear caster 436 are mounted to the bottom of right base 418. These casters are preferably power-operated casters that can readily be controlled to change states by the user or by system logic. The casters can have different states. Preferably the casters have three states: 1) unswiveling; 2) free swiveling and 3) braked. Suitable powered casters are Trinity EBC electronic braking castors available from Fallshaw Wheels & Castors, Victoria, Australia. The powered casters may also be manually adjusted to change states by depressing a pedal on the caster. Other casters may be only manually operated. The use of controllable casters in the walker device allows for various physical or gait therapy modes. When the front castors 430 and 434 are allowed to freely swivel, and the rear casters 432 and 436 are fixed, the device is most easily steered by the patient. On the other hand, when the rear castors are set to freely swivel while the front casters are fixed, the device is easiest to steer by the therapist or provides more steering stability if operated by the patient. When both the front casters and rear casters are set to freely swivel, the device is more maneuverable. Finally, when both of the front casters are set to a fixed forward position, the device only moves in a straight line, which can be a beneficial for patients who have difficulty balancing or walking in a straight direction. The casters may be placed in a braked mode when desired by the therapist. The caster modes can be easily set by the therapist during use from the user interface 440 mounted on top of the crossbar 424, from controls buttons 445 positioned on the push handles 444 and 446 (see FIG. 42), or manually on the individual castors.

Extending vertically from left base 416 and right base 418 are left push handle 444 and right push handle 446, respectively. The right and left push handles attached at the rear of the base units enable a therapist to guide the device during therapy. The push handles 444 and 446 move forward and backward along a track 448 located within the top surface of the left and right base units. The push handles lock and unlock to move along the track by means of controls located on the handles. When the push handles are in their forward position with respect to the front end 410 of the walker device 400, the device may be positioned with the rearward portions of the base units extended under a bed or therapy table. This feature allows the patient to be attached to the body lift-assist walker device 400 without interference with the bed or therapy table from the handles. In a preferred mode, the push handles 444 and 446 are moved forward and backward manually by the therapist. The device may also have a powered means for moving the handles forward and backward along the tracks 448.

Figure 42:
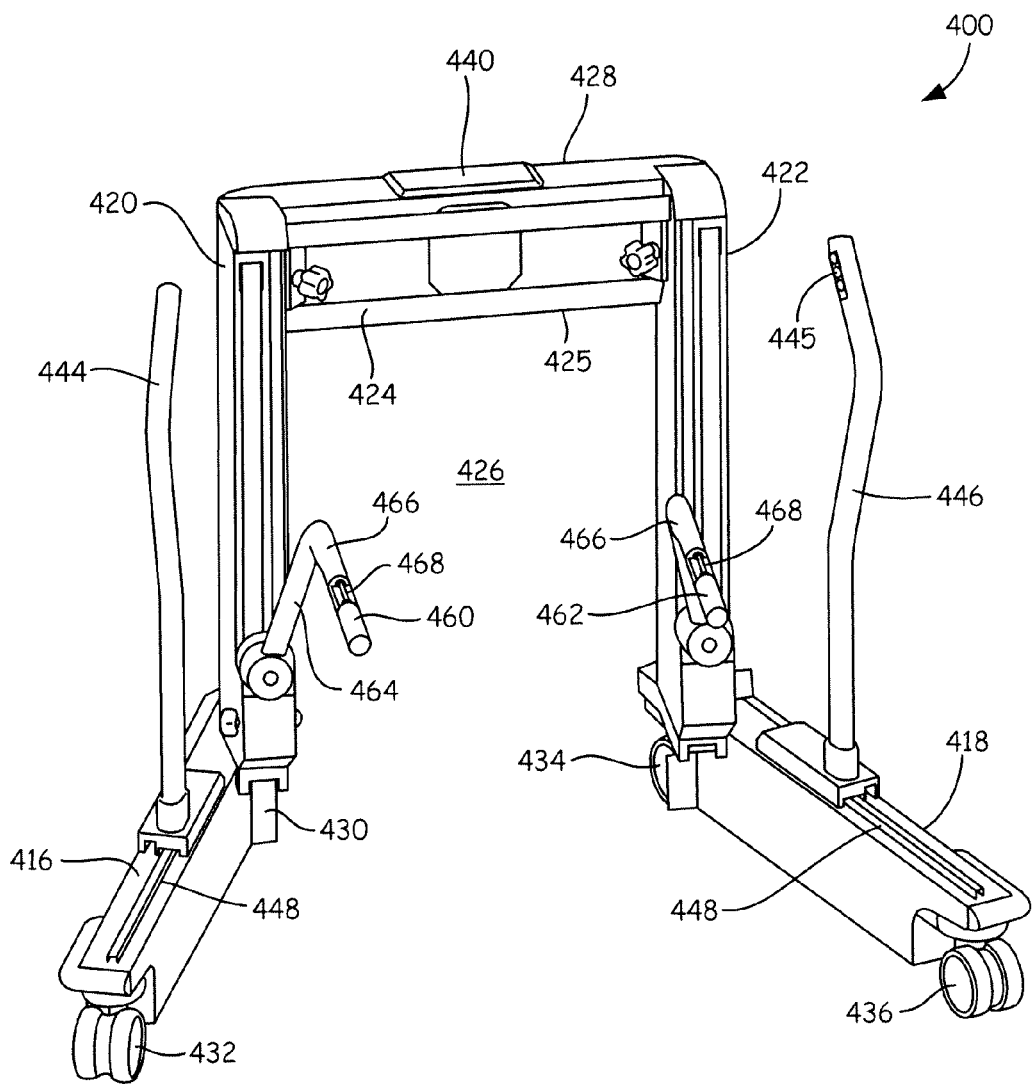
FIG. 42 is a rear perspective view of the body lift-assist walker device of FIG. 40.

The left base unit 416 is attached to the left upright unit 420 by means of left pivot mechanism 450. Similarly, right base unit 418 is attached to the right upright unit 422 by means of right pivot mechanism 452 (not shown). The pivot mechanisms are attached to their respective frame uprights. This pivot attachment allows the left and right base units 416 and 418 to be pivoted outwardly to spread the bases units apart, as shown in FIG. 42. This feature allows the walker device with its spread base units to be positioned further under a bed or therapy table so that the device may be positioned close to the patient when attaching or detaching the device to the patient to lift the patient from a wheel chair, bed, therapy table, chair or other furniture. This feature is also helpful when the patient is sitting in a wheel chair, which can be accommodated by the more widely spread base units. Another use for the pivot mechanism is to provide additional lateral room for the patient's legs during therapy by spreading the base units, in particular for the patient to practice lateral stepping during gait therapy.

Extending back from the rear surface of left upright 420 and right upright 422 is left lift arm 460 and right lift arm 462, respectively. Each lift arm has an angled section 464 and a horizontal bearing arm 466. Positioned along the top surface of each horizontal bearing arm 466 is latch mechanism 468.

Figure 43:
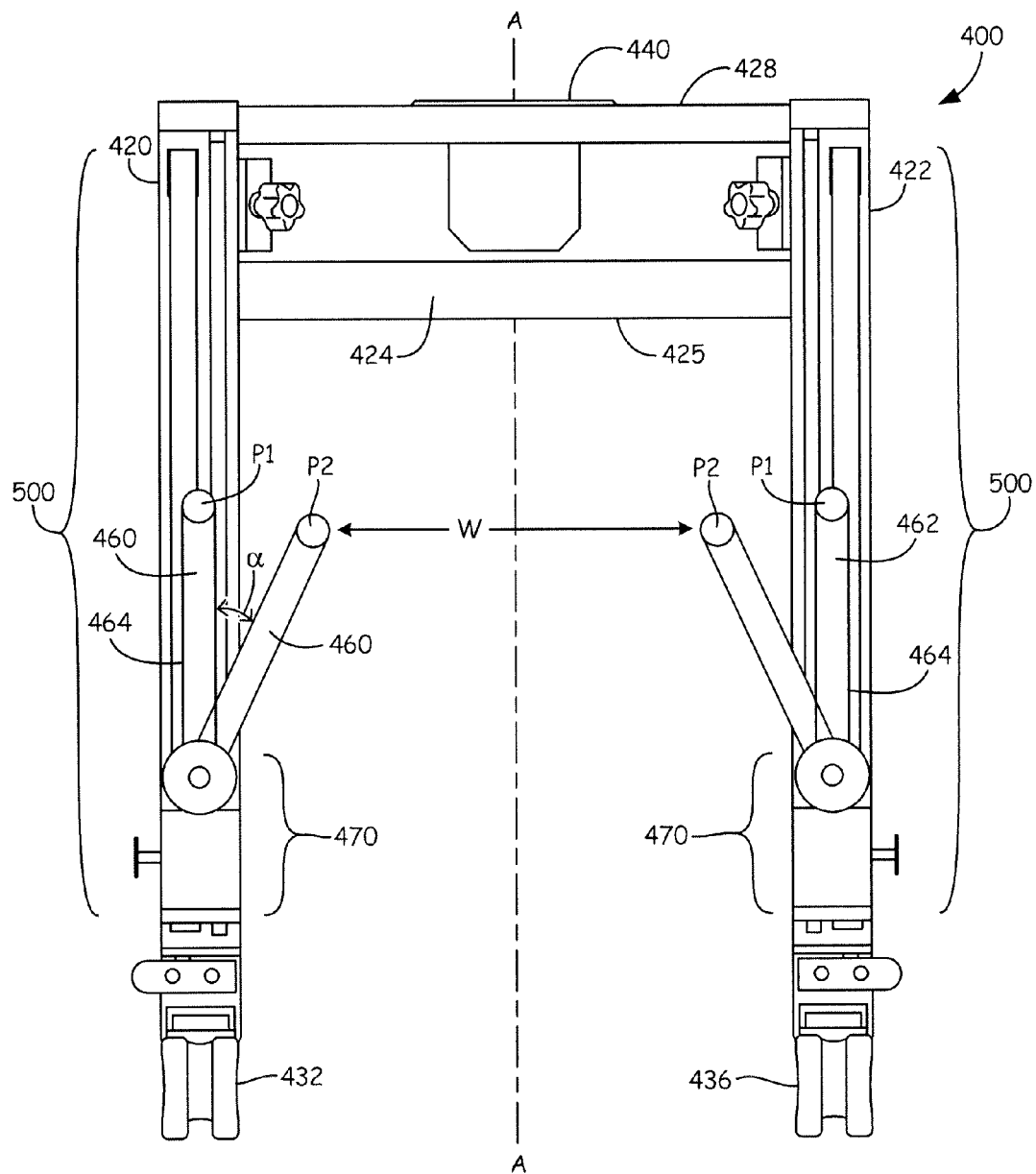
FIG. 43 is a partial rear elevation view the body lift-assist walker device of FIG. 40.
Figure 44:
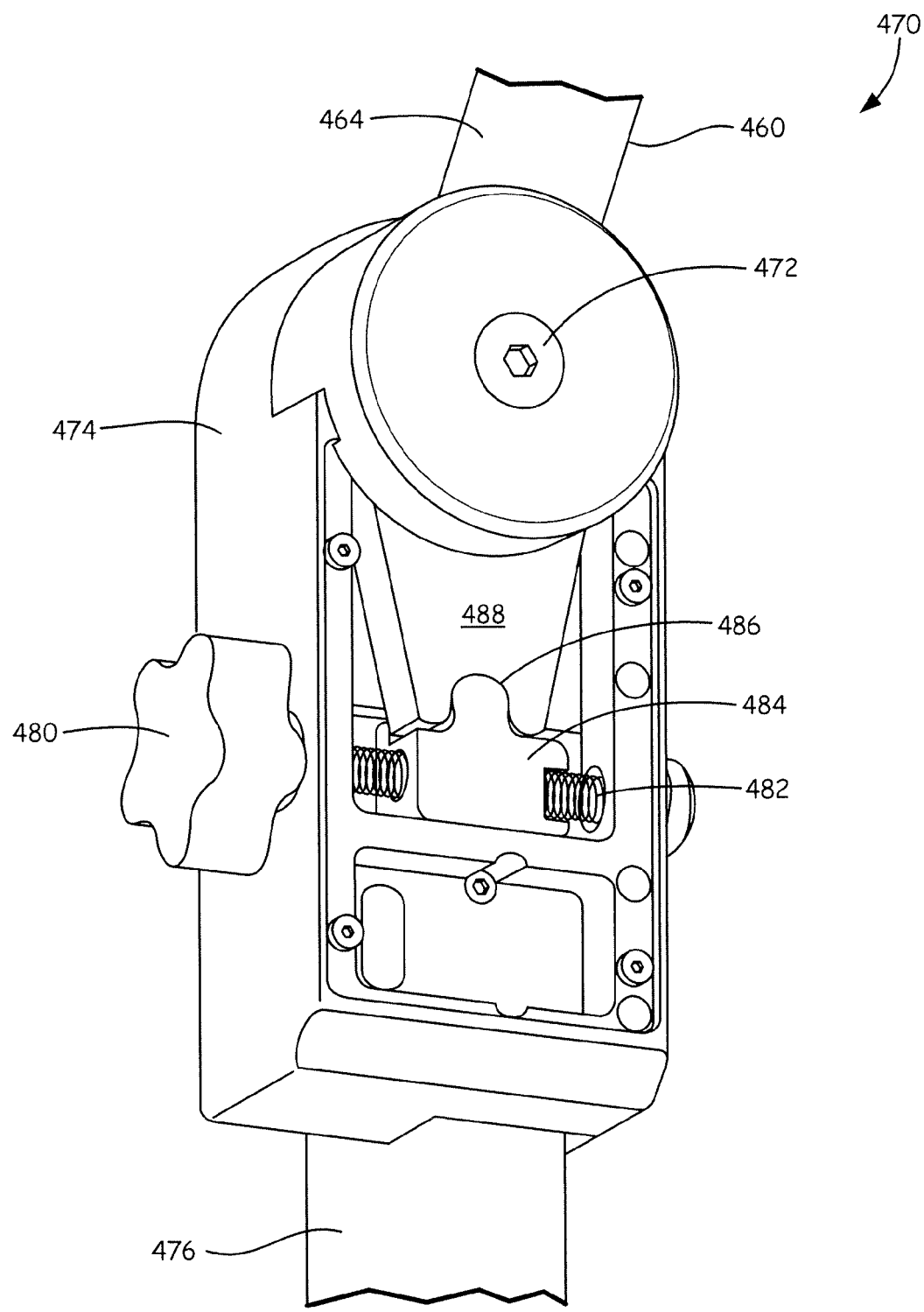
FIG. 44 is a cut-away view of the left-side lift arm width adjustment mechanism for the walker device.

FIG. 43 is a cross-sectional rear view of the walker device without the push handles shown. The angled sections 464 of lift arms 460 and 462 are attached to their respective upright units 420 and 422 by means of lift arm width adjustment mechanism 470. FIG. 44 shows a detailed interior view of the left lift arm width adjustment mechanism 470. The angled section 464 of the lift arm 460 attaches at the shoulder bolt 472. This mechanism has a lift arm mount 474 which attaches to a linear rail (not shown) and belt 476. The lift arm mount travels vertically along the linear rail as the belt moves to raise or lower the lift arm 460. The lift arm adjustment mechanism 470 utilizes an acme screw and nut mechanism to change the angle of the lift arm relative to the axis A-A of the walker device, which in turn adjusts the width W between the two lift arms. The mechanism has a knob 480 attached to an acme screw 482 that moves an acme nut 484 that meshes with a slot 486 in the lift arm pivot 488. Turning the knob changes the angle $\alpha$ of the lift arm 460 to move the arm inwards or outwards around pivot point 472 between, e.g., alternative position P1 and P2 as needed to adjust the width W between the lift arms to fit various patient width sizes. When the arms are position P1 the horizontal support bars are open for the widest setting. When the lift arms are in position P2 the lift arms are at a narrower width. Other mechanisms suitable for adjusting the angle of the lift arms include a power-actuated mechanism.

Figure 45A:
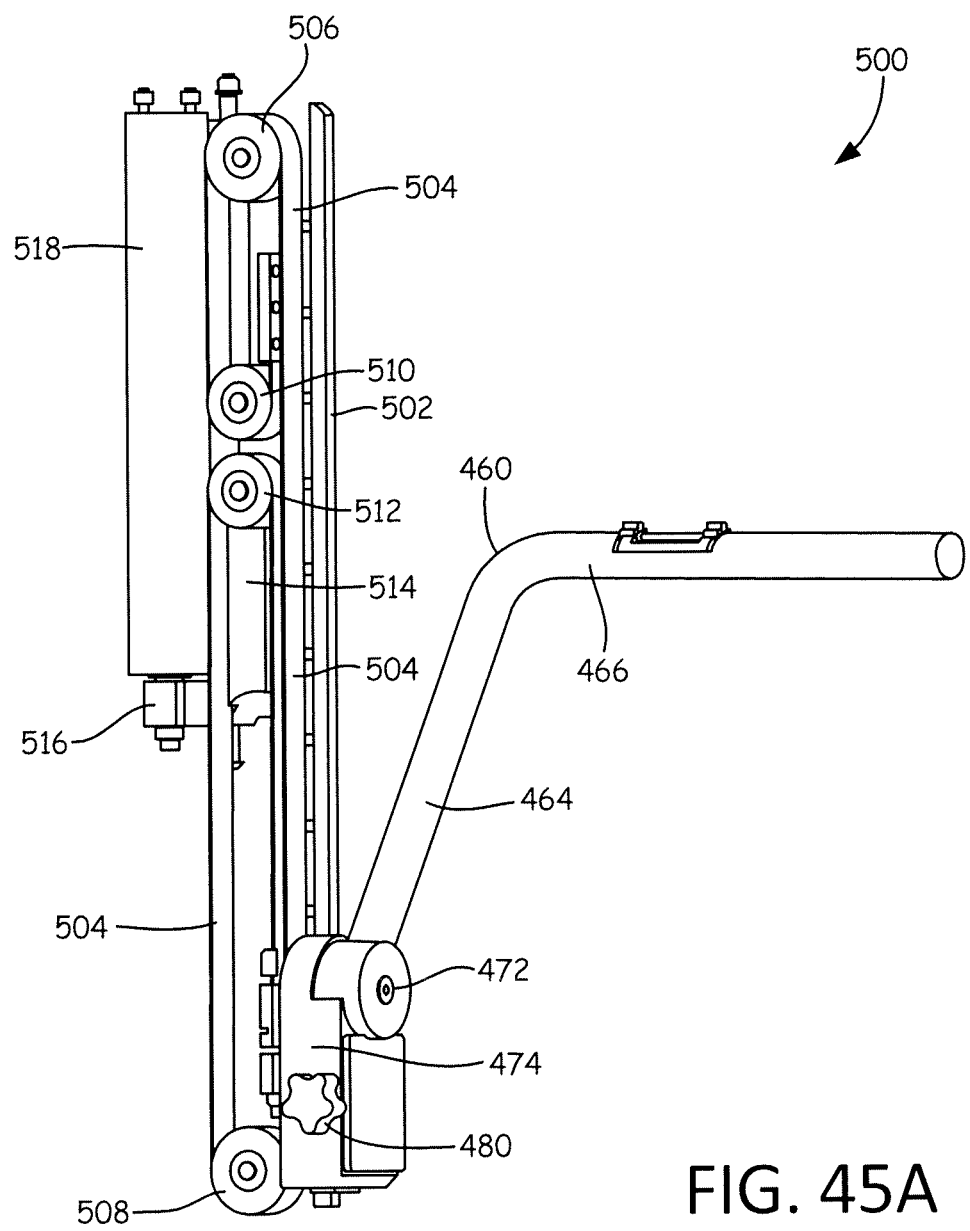
FIG. 45A is a cut-away view of the left-side lift mechanism for the walker device in the lowered position.
Figure 45B:
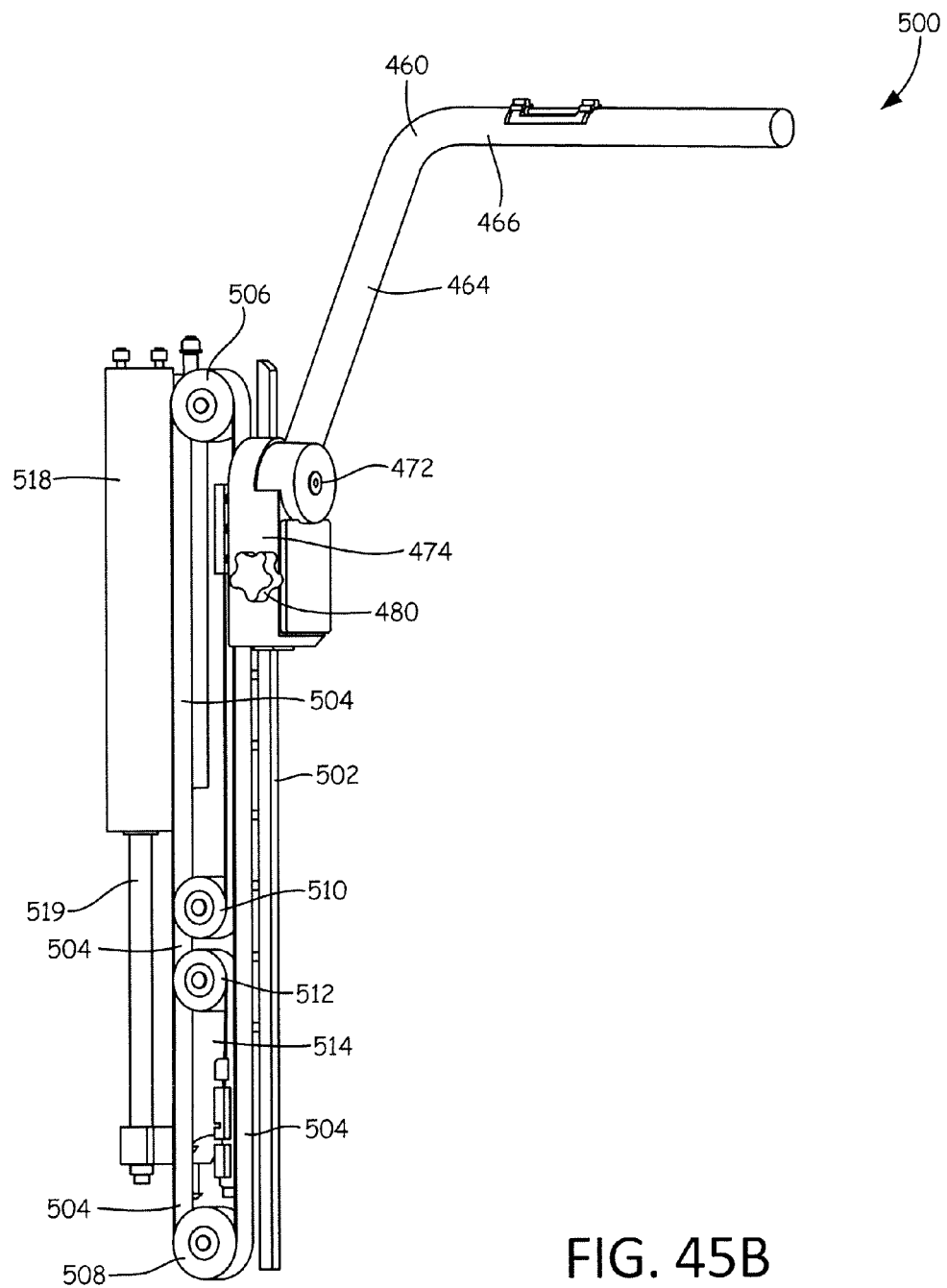
FIG. 45B is a cut-away view of the left-side lift mechanism for the walker device in the raised position.

Details of the lift mechanisms 500 for raising and lowering the lift arms 460 and 462 are shown in FIGS. 45A and 45B. The lift mechanism 500 is designed to have enough travel to accommodate a sit-to-stand motion for patients of all heights. Thus, the mechanism must have a range of travel so that the lift arms extend vertically at the proper height for the tallest person. A preferable range of travel is 24 inches.

As shown in FIG. 45A, the lift arm 460 is attached to the lift arm mount 474. The lift arm mount connects to a linear rail 502 via bearings in the mechanism housing allowing it to move up and down vertically while under load. Suitable linear rails and bearings are available from Thomson Linear Rails and Bearings, Radford Va. The lift arm mount 474 is attached to a belt 504. Suitable belts are the ATLF Belt available from Gates Mectrol Inc, Salem N.H. The lift arm mount 474 bearing the lift arm 460 is actuated by the travel of the belt 504. The belt passes around upper idler roller 506 and lower idler roller 508 and moveable idler rollers 510 and 512. These moveable idler rollers 510 and 512 are connected to linkage 514, which is connected to the cylinder lift arm 516 of air cylinder 518. The air cylinder 518 provides a relatively constant force over the range of travel. A regulator in the control system maintains the pressure in the air cylinder within a narrow range as required by the amount of body weight offloading for the patient that is needed.

The lift mechanism 500 is shown in FIG. 45A with the lift arm 460 in the bottom position that has a height corresponding to a patient sitting in a wheel chair, on a chair, or on a bed or therapy table. When the air cylinder 518 is pressurized, its piston rod 519 provides a constant downwards force on the moveable idler rollers 510 and 512, as shown in FIG. 45B. This provide an upwards force via the belt 504 on the lift arm mount 474. The ratio between the distance of travel of the air cylinder and the width adjustment mechanism is 1 to 2. And the resulting ratio between the force provided by the air cylinder and the force on the lift arms is 2 to 1. When a patient transitions from the sitting position to the standing position, the lift arms move vertically upwards while providing a constant lifting force on the lift arms 460 and 462 to assist the patient in standing. The lift mechanism 500 includes a dampener which prevents excessive movement of the lift arms in the event that the bar is suddenly unloaded, and provides for a controlled descent if the patient collapses or pressure is lost. In a preferred embodiment, the constant force mechanism is an air cylinder. Alternatively, it can comprise an air spring, torsion spring, or helical spring.

Figure 46:
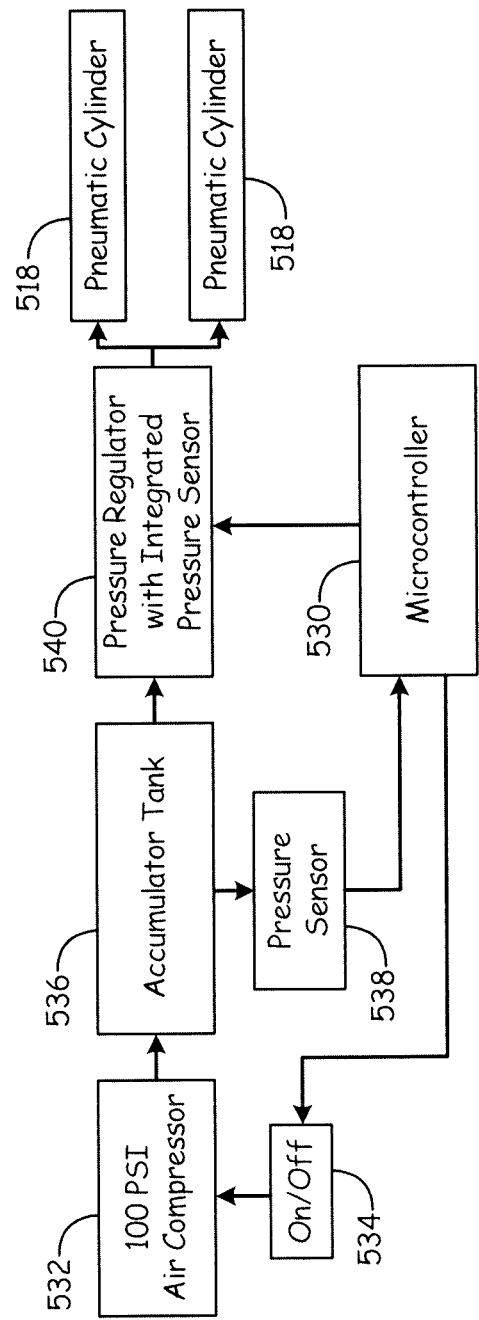
FIG. 46 is a schematic view of the controller circuitry for the pneumatic cylinder-actuated lift mechanism for the walker device.

FIG. 46 shows a schematic of the pneumatic control system. The counter tensioning pneumatic system of the lift mechanism 500 is operated by the controller interface 440, and is under the supervision of microcontroller 530. An air compressor 532 capable of delivering about 100 psi of pressure is turned on or off via the microcontroller 530 using electronic switch 534. An Thomas 415CDC30/24 air compressor sourced from Gardner Denver Thomas, Munich Germany is one such suitable device. An accumulator tank 536 is charged to about 90 PSI, and the microcontroller software receives knowledge of the pressure condition via pressure sensor 538 to maintain the target accumulator pressure of 90 PSI. The accumulator tank 536 may actually be a network of tanks of dimension for efficient packaging. A useful tank is the 1750VCS-8.00 model sourced from American Cylinder Inc., Peotone Ill. Six such cylinders, 8 inches long by 1.75 inches in diameter, yield efficient packaging and about 115 cubic inches of volume. This is of sufficient volume such that a large displacement movement and thus volume change desired on the pneumatic cylinders 518 may be accommodated readily by the accumulator volume.

Suitable pneumatic cylinders are model 6461K35-12 by McMaster Inc. Using a pair of these 12 inch by 2 inch bore cylinders yields about 75 cubic inches of pneumatic cylinder displacement. With said cylinders, each of cross sectional area of 3.14 square inches, a pressure of about 45 PSI delivered through generates about 300 pounds of lift, which is reduced by a factor of two using the previously described belt drive. For example, a delivery of 45 psi pressure desired to yield complete displacement of the lift cylinders results in a PV product of 45*75=3375 pound cubic inches. The accumulator at 90 psi contains 90*115=10350 pound cubic inches, so it would only be reduced to about 60 psi with this maneuver. The desired pneumatic cylinder pressure, and thus lift force, is maintained under microcontroller 530 supervision, which provides a control signal to pressure regulator 540, such as the ER09 series manufactured by Wilkerson Inc., Richland Mich.

Figure 41:
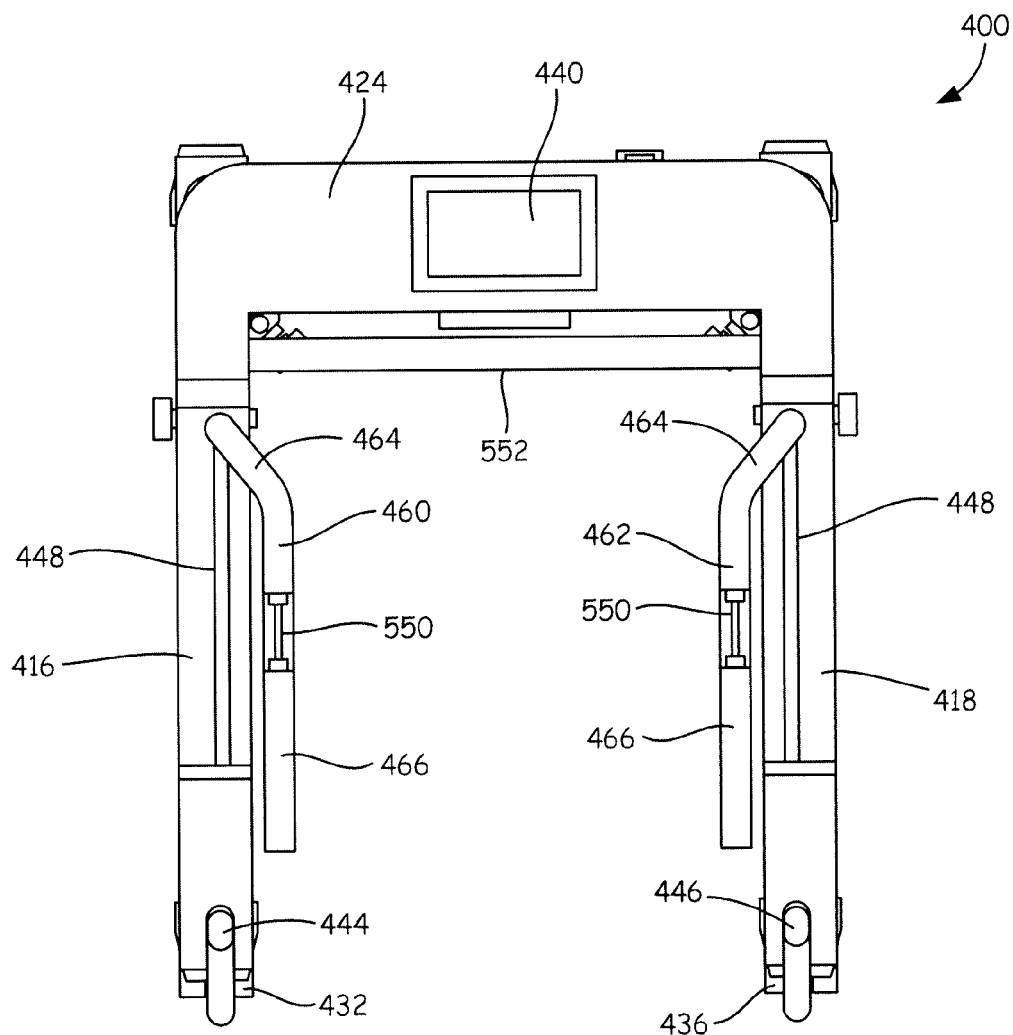
FIG. 41 is a top plan view of the body lift-assist walker device of FIG. 40.

Built into the top surface of each lift arm 460 and 462 is attachment latch mechanism 550, as shown in FIG. 41 from a top plan view. Push handles 444 and 446 are positioned in their forward position. The attachment latch mechanisms 550 are utilized to attach the lower body suit 14 to the lift arms 460 and 462. A touch screen user interface 440 is provided on top of the crossbar 424. A handle bar 552 is provided which allows the patient to hold onto and steer the walker device 500.

FIG. 47 shows the attachment latch mechanism 550 of the device in greater detail. The latch body 556 fits into the horizontal bearing segment of the lift arm so that the body is flush with the support arm. The latch pin 558 is shown without the webbing from the pressurized body suit 14. Right and left latch thumb knobs 560 and 562 rotate around latch pivot shaft 566, and secure the latch pin 558 securely in the latch. The right and left latch thumb knobs 560 and 562 are mechanically coupled so that opening either opens the other as well. A torsion spring 564 allows the latch to spring back into place when the thumb knobs are released. The dowel pin 565 acts as a stop for the torsion spring 564. The therapist may release the patient in an emergency when the latch is under a load by opening the thumb knobs and pulling up on the strap that the latch pin 558 is attached to it. Other attachment means can be quick release buckles. Preferably these could be quick release buckles that release under load so that the patient can be detached quickly in an emergency.

FIGS. 48A, 48B, and 48C show respectively a front view, side view, and rear view of a pressurized body suit 580 of the present invention that covers the lower portion of the body from the person's waist down. It allows unrestricted body and leg movements and allows for quick attachment and detachment of the patient. Preferably the body suit is pressurized which may be used in a differential pressure body weight support device. Alternatively, the lower body suit may also be unpressurized.

The lower body suit 580 may consist of various patterns and layers of two-way stretch fabrics. Right front support section 582 is attached to the pants at the right front seam 584. Left front support section 583 is attached to the pants at the left front seam 585. Left rear support section 586 it attached to the pants at the left rear seam 587. Right rear support section 588 is attached to the pants at the right rear seam 589. The support pieces are made from sturdy fabric that does not stretch in at least one direction under load. The support fabric piece can be made of the same two-way stretch fabric as the lower body suit, itself. The direction of non-stretch is aligned so that the fabric does not stretch when the pants are loaded with a pressurized condition. This is approximately 45 degrees to the longitudinal direction of the pants. The left front and left rear support pieces 583 and 586 are sewn together onto a left webbing strap 590. Right front and rear support pieces are similarly attached to a right webbing strap 592. A left latch pin 594 is sewn between the webbing straps.

Figure 49:
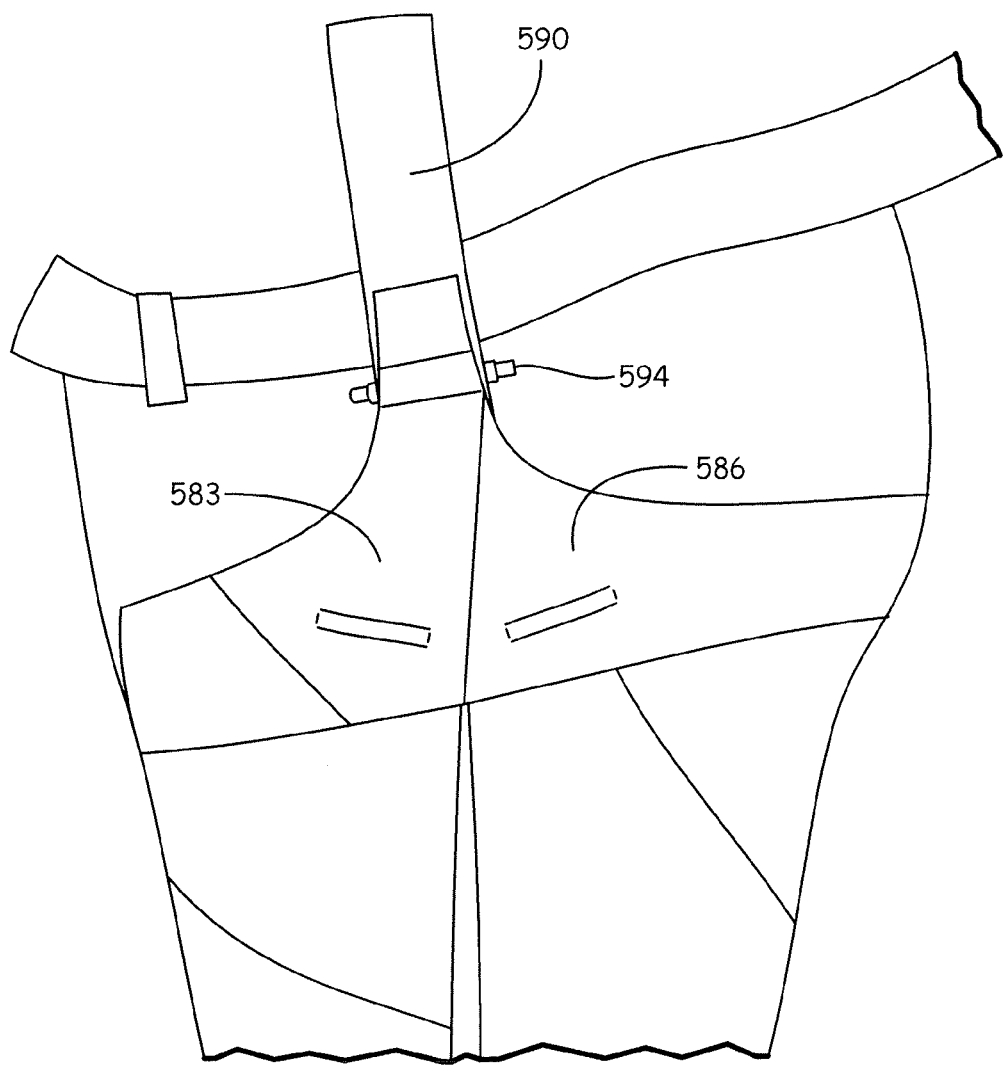
FIG. 49 is a partial perspective view of the lower body suit of FIG. 48 containing support pieces attached to the webbing and the latch pin.

FIG. 49 shows a detailed view of the support pieces attached to the webbing and latch pin. The left front support piece 583 and the left rear support piece 586 are joined together. A left latch pin 590 is sewn together onto the left webbing strap 590. The latch pin attaches to the latch mechanism 550 in the support arms 460 of the body weight support device. The support strap 590 is used to position the latch pin 594 into the latch and to remove the latch pin from the latch when detaching the patient from the body lift-assist walker device 400. This support mechanism provides for a pivot point for the latch located at the approximate position of the hip joint. This allows the patient's legs and suit to pivot about this point during movement. Thus this support mechanism supports body weight while allowing for unrestricted movement of the legs as they swing back and forth about the hip joint during walking. Since the pivot point of the suspension device is located at the approximate angle of the hip joint, the legs can swing back. The pivot bearing attachment allows the patient's legs to approximately pivot about his medio-lateral (i.e. side-to-side) axis in the device which allows for unrestricted rotation of the person so that they can lean forwards or backwards somewhat during the walking gait. In summary, the support mechanism provides a means for supporting body weight allowing for free swinging of the legs' medio-lateral axes of rotation through the hips and front to back leaning through the medio-lateral axes of rotation through the waist.

Figure 50:
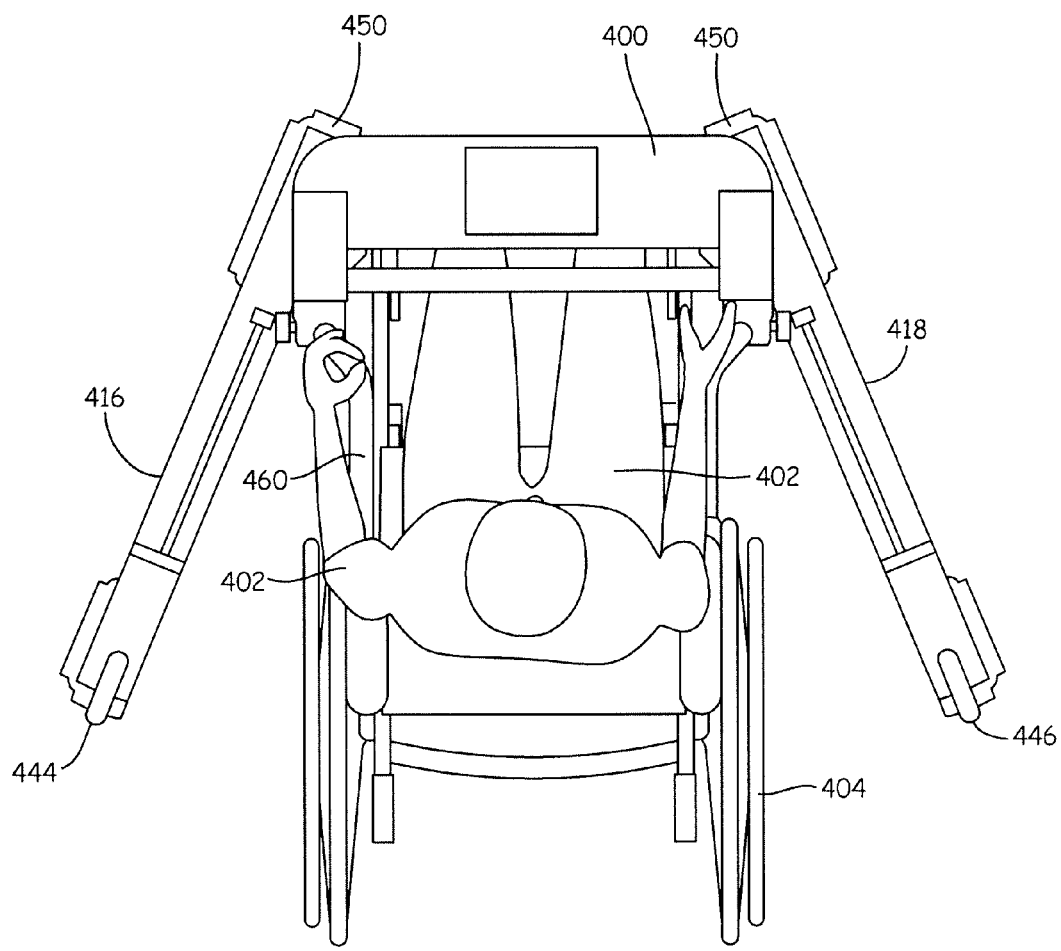
FIG. 50 is a top plan view of the body lift-assist walker device of FIG. 40 with a patient wearing a pressurized lower body suit in a wheel chair attached thereto ready to undergo the sit-to-stand motion.
Figure 51:
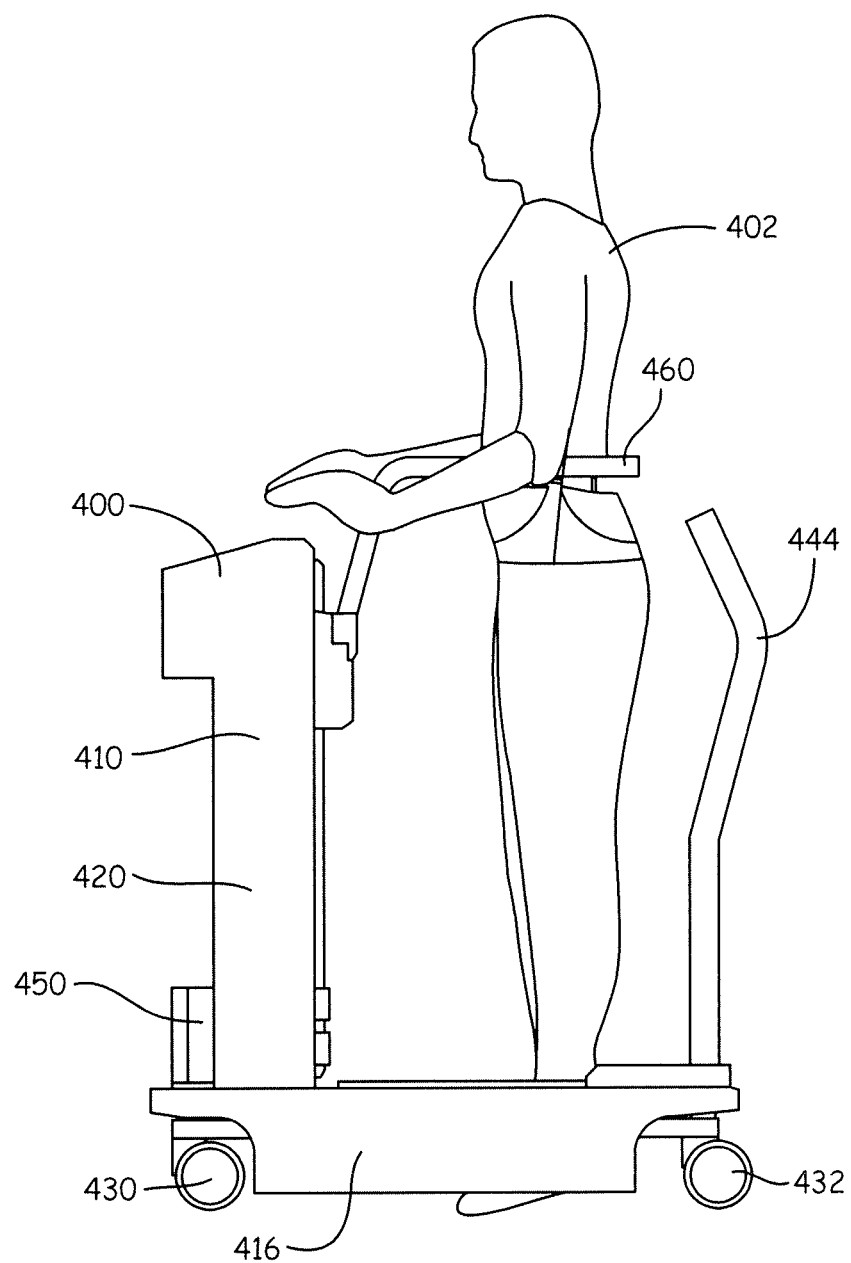
FIG. 51 is a left-side elevation view of FIG. 50 after the patient has completed the sit-to-stand motion.
Figure 52:
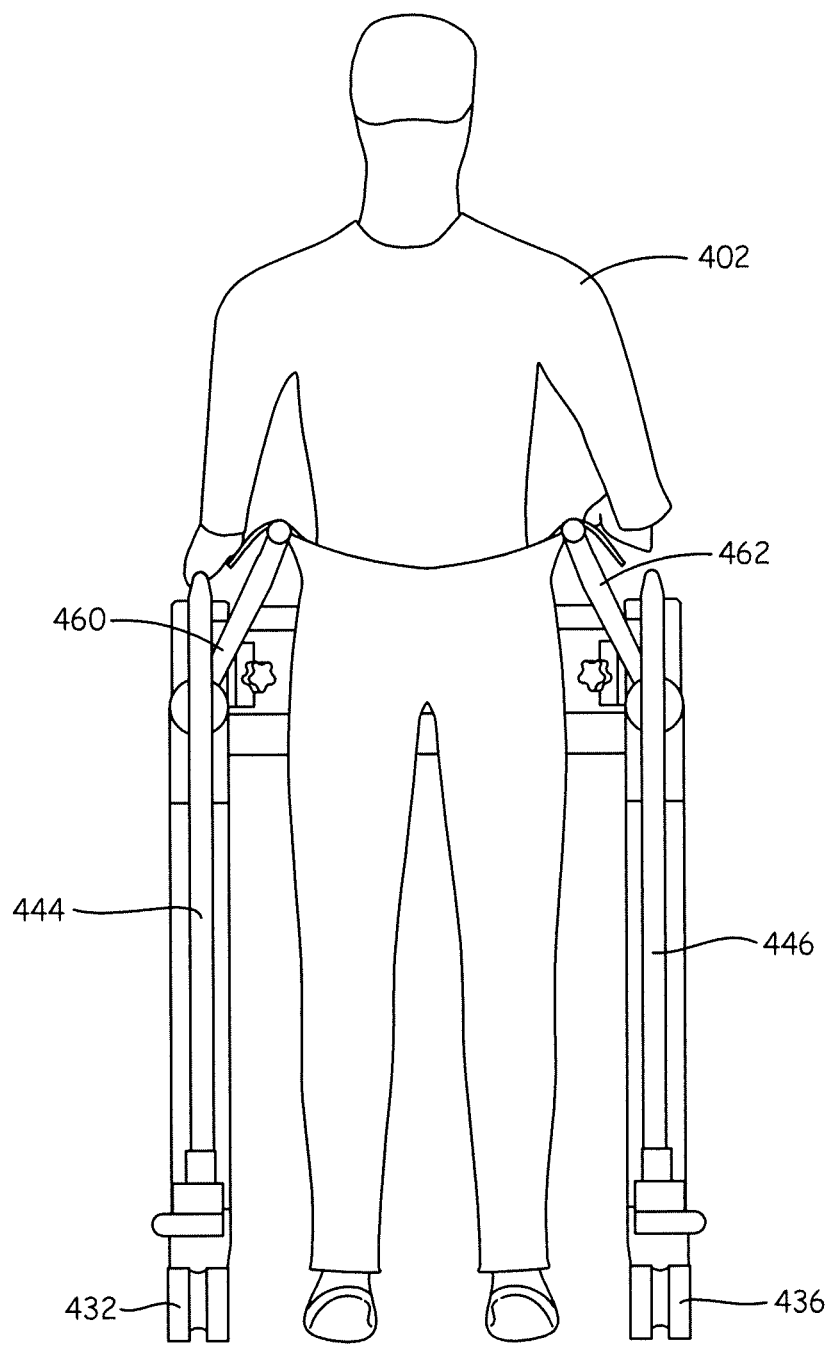
FIG. 52 is a rear elevation view of FIG. 51.

FIG. 50 shows an overhead view of the patient 402 sitting in a wheel chair 404 in operative engagement with the body lift-assist walker device 400 of the present invention. FIG. 51 shows a side view of the patient standing up with respect to the walker device aided by its sit-to-stand assistance functionality. FIG. 52 shows a rear view of the patient standing up with respect to the walker device. It is desirable for the device 400 to be capable of being positioned relative to the patient 402 in the wheel chair 404 so that the patient attaches to the lift arms 460 and 462 of the device while seated. This is accomplished in the device by having the base units 416 and 418 spread out to accommodate the wheel chair. A locking means is provided in the pivot mechanism 450 to lock and unlock the base units in the open and closed position. The device may also have means for locking the bases in other intermediate positions between the opened and closed positions. When in the closed position and with the pivot mechanism unlocked, the therapist may then open the base units by pushing the push handles 444 and 446 outward to their open position. When in the fully open position, the pivot mechanism 450 locks in that open position. When the pivot mechanism 450 is unlocked for spreading the base units, the control system also changes the state of the front casters 430 and 434 to their braked condition, so that the device is stabile during movement, and the state of the rear casters 432 and 436 is set to their unbraked condition to freely swivel in order that the rear casters can track during the spreading movement. In a preferred mode, the base units are manually spread by the therapist by pushing the rear push handles 444 and 446 outwards. The device may also have a powered means for spreading the bases. Thus, in this spread position, the device can accommodate an extra-large sized wheelchair so that the wheelchair can be positioned with the front close to the front of the lift arm width adjustment mechanism 470. When the chair is positioned directly in front of the device as far as it can go, the attachment points to the patient are at the mid-point of the wheelchair approximate to the patient's waist, thereby facilitating attachment without the patient having to move to the edge of the wheelchair.

FIG. 39 shows a side view the view depicted in FIG. 50. The horizontal base has been spread to allow the wheelchair to be put into position close front of the device. The lift arms 460 and 462 are in a lower position. The lift arms have a minimum height that is slightly greater than the seat height of the wheel chair. This allows for easy attachment of the attachment latch mechanism 550 of the lift arms to latch pin 594 on the pressurized body suit worn by the patient. Preferably the lift arms can be lowered to a minimum height of 16 inches or less, which is less than the height of a standard wheelchair seat.

The lower body suit can be a pressurized to provide a differential pressure condition across the suit. When pressurized, this differential air pressure condition provides an upwards lift on the patient and a downwards force on the lift arms 460 and 462. The lift arms 460 and 462 support the downward force applied by the differential air pressure condition on the lower body suit. An air hose from the device is connected to the lower body suit at attachment point 600. The attachment has a quick release fitting which allows for easy attaching and detaching of the air hose. Or the suit can be non pressurized suit in which case the suit pulls up directly on the patient to provide the lift. The lift arm consists of a horizontal section (464) and angled section (466). The angled section of the lift arm 464 attaches to the lift arm mount 470. The inventive advantage of having lift arms of this geometry is that it allows the therapist unobstructed access to the patients lower body from the side.

Upon operation of the air cylinders 518 to raise the lift arms 460 and 462 as described above, the patient 402 will be greatly assisted in the sit-to-stand motion to rise to the standing position. This is accomplished both by the upwards movement of the lift arms, and by the offloading of the patient's body weight caused by the differential pressure condition across the lower body suit. In patients for whom extra boost is needed to move from sitting to standing, the system may provide short-term increased air pressure in the pressurized pants to aid lift. The effect of the lift force is instantaneous over the entire range of travel of the lift arms 460 and 462. Thus, the device can allow a patient to rise from a sitting position to a standing position within two seconds or less.

It is desirable for the body lift-assist walker device to have a small footprint during use, and in particular a width that is not much wider than that of the widest patient. In particular it is preferable that the device be able to navigate through doorways. A preferred maximum width for the device is 27 inches. A preferred maximum length for the device is 35 inches. This allows it to be turned within a small radius. It is preferred that the maximum height of the device be similar to that of a standard walker and that there are no overhead components to the device. Otherwise, overhead and above-waist components can interfere with the visual view of the patient, the face-to-face interaction between the therapist and the patient, with access to the patient's upper body, and even with passage through doorways.

Figure 53:
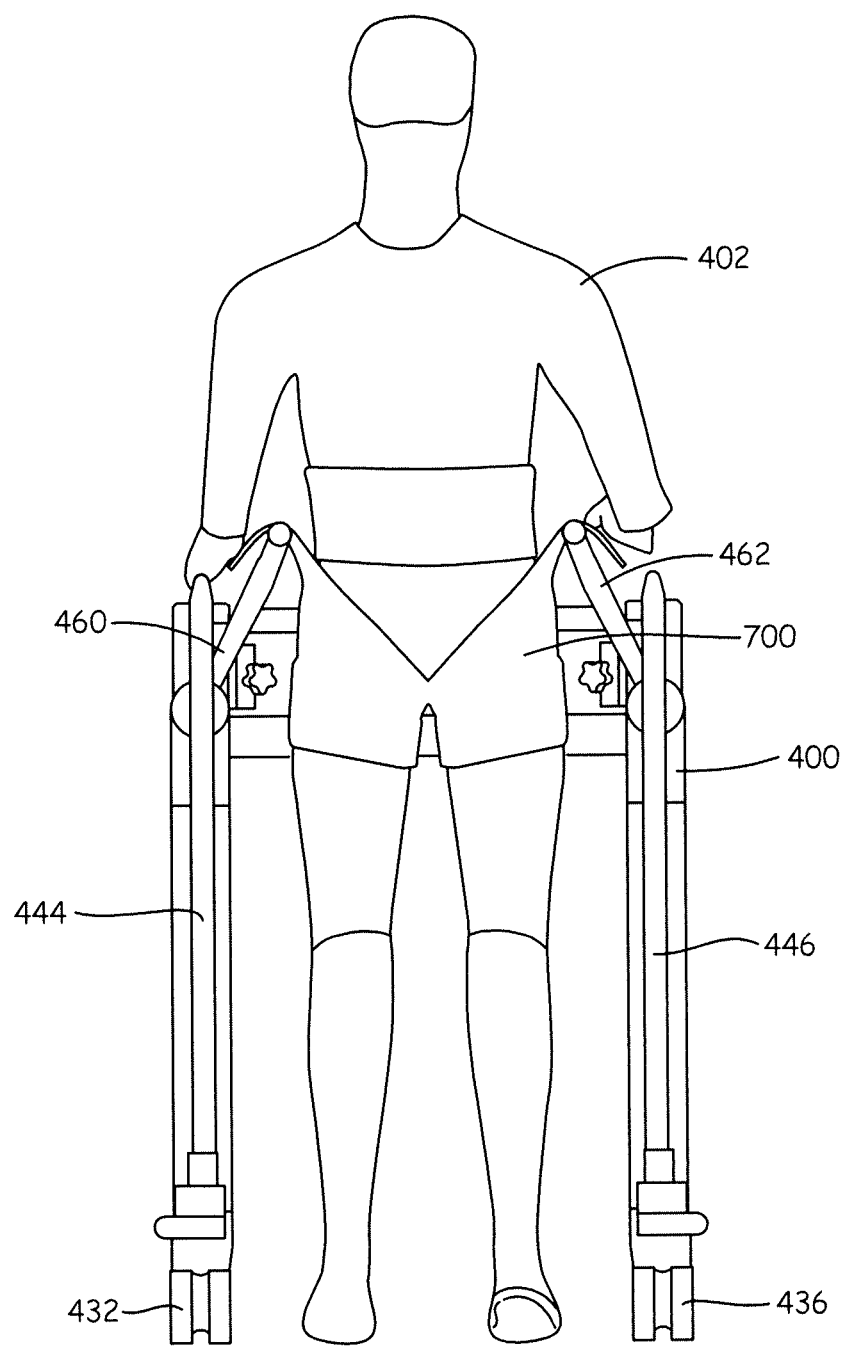
FIG. 53 is a rear elevation view of the body lift-assist walker device of FIG. 40 with a patient wearing a harness after he has completed the sit-to-stand motion.

FIG. 53 depicts a harness 700 to be used with the body lift-assist walker device 400 of the present invention. Such a harness may be used in cases where only a smaller amount of body weight support is needed such that body weight support may be provided to the patient without discomfort. The harness 700 can also be used without weight offloading or minimal off loading in order to help the patient with just maintaining balance and walking safely. The harness may also be utilized where support is also needed only for a short time such as getting up from a hospital bed and walking a short distance safely to use the bathroom.

Figure 54:
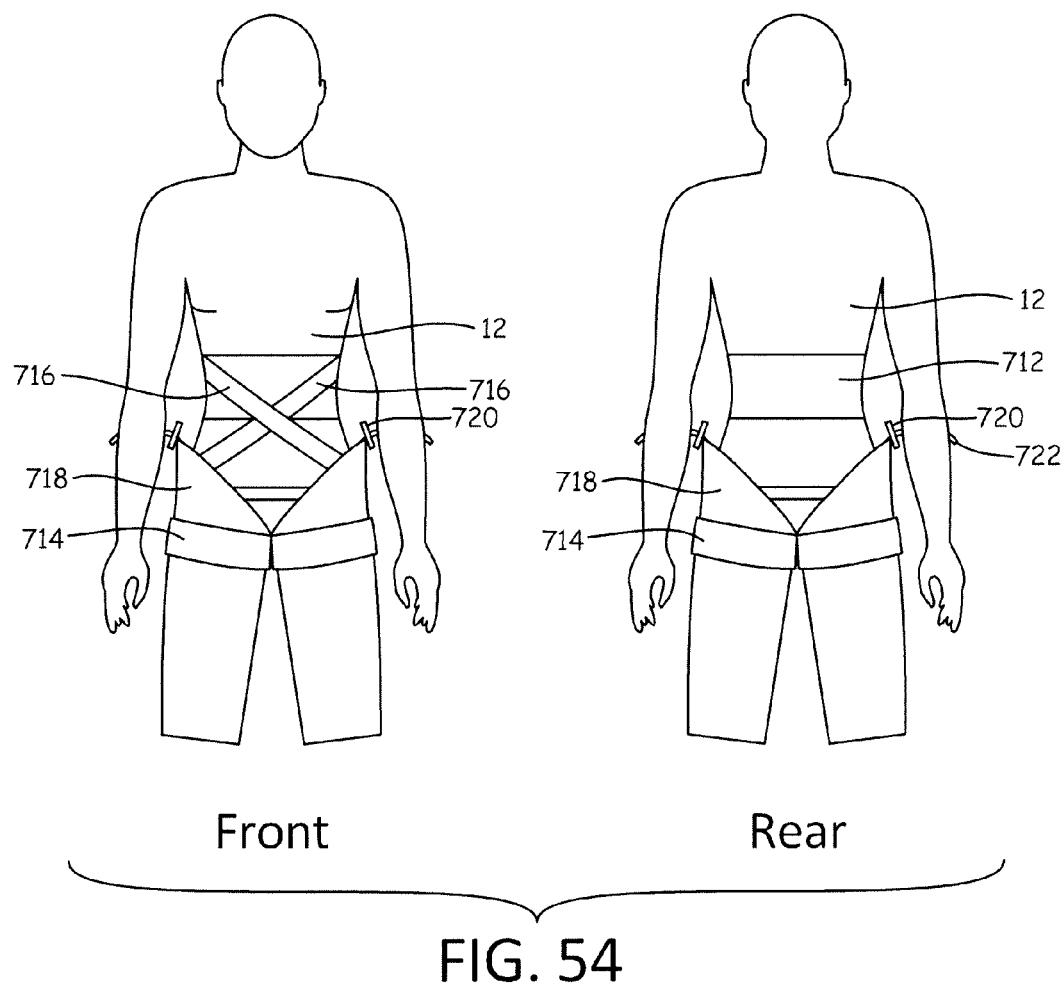
FIG. 54 shows front and rear views of another design for a harness system that can be used with the body lift-assist walker device of the present invention.

The person depicted in FIG. 54 is wearing a body harness 710. A waist strap 712 goes around the waist of the person. Leg straps 714 go around the upper thighs and or lower buttocks of the person. Cross straps 716 connect the lower leg straps 714 to the waist strap 712. Front support pieces 718 are utilized to connect the harness 710 to the lift arms of the walker device via a latch pin 720 incorporated into the upper end of the support piece. The design of the latch pin and latch mechanism are similar to that used on the lower body suit. A webbing strap 722 is attached to the support piece to facilitate placing the latch pin into the latch on the support arms. The support pieces are attached to lower leg straps 718. The lower leg straps provide support. The harness is made from sturdy fabric and webbing. Buckles are provided to connect and cinch the harness tight against the body. The harness may also be constructed of lighter-weight fabrics similar to those used in the lower body suits in order to provide additional comfort and wearing for extended time periods. For instance a light-weight harness may be worn by a patient in a hospital bed and utilized from time to time when the patient needs to get up and walk short distances. Or the harness may be worn by a patient when the device is used for home use where smaller amounts of body weight support are needed for stability and safety. The use of a non-pressurized compact body weight support systems allows for providing a simpler light weight device for home use, because the means for providing pressurized air are not required.

It is important that the attachment of the body lift-assist walker device 400 to the pants or harness allow supporting body weight without restricting body movement. A cord and pulley suspension system, as described above, provides a means for supporting body weight without restricting body movement and rotation about all four axes of rotation. However, such a cord and pulley attachment system may make it more difficult to quickly attach the patient to the walker device. In particular it may be difficult to attach to a person who is seated, especially when seated in a wheel chair. Another requirement for a therapeutic body weight support system suspension system is that it the therapist must be able to quickly detach a patient from the device in an emergency.

The operational theory of the differential pressure unweighting suit has previously been described in U.S. Pat. No. 8,663,133, which is incorporated hereby in its entirety. While various embodiments have been previously described that detail the cross sectional area calculations of the pressure, they may be represented by a single net area term $A_n$, such that:

$$F_b = \Delta P A_n$$

where $F_b$ is the net upwards force on the body developed by the differential air pressure $\Delta P$, and $A_n$ refers to the net effective cross sectional area of the body suit, which may represent the cross sectional area of the waist minus the cross sectional area of the ankles. In the specific embodiment described herein, the pants size donned by a subject is known at the outset of usage, denoted in belt size. Using this information, a lookup table in the software provides an initial estimate of cross-sectional area, $A_n$. Preferably from a graphical user interface, the therapist or other operator enters the desired unweighting value in pounds or other suitable units which represent the desired unweighting force $F_b$. The governing equation, arranged with the pressure $\Delta P$ on the left hand side is:

$$\Delta P = F_b / A_n$$

Thus, a target value $\Delta P$ is determined as the desired pressure to introduce into the unweighting suit. Also as described previously, a vertically upwards counter force $F_c$ must be applied to the unweighting suit, identical in magnitude to the downwards force generated by the air pressure on the unweighting suit, and also identical to the upwards force on the subjects body. If these forces are not balanced, or equal in magnitude, the unweighting suit will either travel upwards or downwards on the subject's body uncomfortably.

As it is not practical to instantaneously pressurize the pants with a pressure $\Delta P$, the target pressure is attained starting from a pressure of 0 over a period of time, typically 10 to 30 seconds. Preferably it is most comfortable to continuously adjust the counter tension force to match the force generated by the suit pressure in intermediate steps, where an intermediate counter tension $F_{ci}$ is applied as a function of the time domain measured intermediate pressure $\Delta P_i$. Preferably, the pants pressure $\Delta P_i$ is sampled about every 100 milliseconds, and the counter tension is adjusted according to the equation:

$$F_{ci} = \Delta P_i A_n$$

In a sit-to-stand maneuver, it is often desired to have a somewhat larger assistive unweighting force than will be desired for normal unweighting. For example, a 200 lbs. subject may be suitably unweighted during normal therapy at perhaps 70 pounds such that he or she effectively weighs 130 pounds; however in transitioning from sit to stand position, it may be desirable to provide a temporary boost of lift, perhaps an additional 50 pounds, such that the subject effectively only weighs 80 pounds to go from sitting to standing. A "boost" feature actuated by the operator is useful to accomplish this, which temporarily suspends the close pressure-counter tension tracking rule described above. Suspending the counter tension tracking rule is useful because there is a significant drop in the pants pressure during the sit to stand transition, but it is not desirable during this short time interval to lower the counter tension $F_c$. Thus, for this brief time, normally on the order of two to ten seconds, the counter-tension is allowed to exceed the value called for by the foregoing equation, and the counter tensioning functions as a simple additive assisted lift. As soon as the subject is standing, the "boost" may be cancelled, or the software may automatically cancel within a suitable time period such as 30 seconds.

The above specifications and drawings provide a complete description of the structure and operation of the body lift-assist walker device 10 under the present invention. However, the invention is capable of use in various other combinations, modifications, embodiments, and environments without departing from the spirit and scope of the invention. Therefore, the description is not intended to limit the invention to the particular form disclosed, and the invention resides in the claim and hereinafter appended.

We claim:

1. A lift-assisted mobility device for assisting the ambulatory motion of a person having a body weight, and ease the movement by that person between a seated position and a standing position, such device comprising:
    (a) a wheeled supportive frame upon which the person may lean while walking or running;
    (b) a pressure-tight suit adapted to being worn over at least one part of the person's lower body having at least one opening for inserting the body part into the suit;
    (c) means for providing a pressure-tight seal connected adjacent to the opening of the suit for operative engagement of the body part surface of the person;
    (d) inlet means in the suit for introduction of at least one source of positive pressure or vacuum to an interior of the suit between the person's body and the suit to create a differential pressure condition therein between the positive pressure or vacuum condition inside the suit, and a pressure condition existing outside the suit;
    (e) a lift-assistance device having a constant force mechanism attached to the supportive frame with a linkage connected thereto;
    (f) at least one lift arm operatively connected to the linkage for movement between a lowered position and a raised position;
    (g) an attachment mechanism connected to the lift arm providing a detachable connection to the suit;
    (h) wherein the differential pressure condition is adapted to exert an upwards force upon the body part to offload a desired portion of the weight of the body to the lift-assistance device and the supportive frame with the supportive frame counteracting a downwards force applied to the suit when it is placed under the differential pressure condition; and (i) wherein actuation of the constant force mechanism raises the lift arm via the linkage from the lowered position to the raised position to lift the suit vertically as the person rises from the seated position to the standing position, whereupon the person may stand easily with reduced effort aided by the reduced body weight, and move about with body weight support.

2. The lift-assisted mobility device of claim 1, wherein the lift arm is operatively connected to a linear rail positioned within an upright portion of the wheeled supportive frame to enable the lift arm to move up and down vertically by means of the linkage operated by the lift assistance device.

3. The lift-assisted mobility device of claim 2, wherein the linkage comprises a belt.

4. The lift-assisted mobility device of claim 3, wherein the belt is adapted to travel around at least one roller.

5. The lift-assisted mobility device of claim 2, wherein the linkage comprises:
(a) a belt to which the lift arm is attached, the belt being adapted to travel around a plurality of vertically disposed rollers, the rollers comprising a fixed upper idle roller, a fixed lower idle roller, and a movable upper idle roller and a movable lower idle roller positioned between the fixed upper idle roller and the fixed lower idle roller;
(b) the constant force mechanism being movable between an extended position and a retracted position to which the upper movable idle roller and the lower movable idle roller are attached; and
(c) wherein the constant force mechanism supplies a force against the upper movable idle roller and the lower movable idle roller to apply an upwards force via the belt upon the lift arm to contribute to the raising of the lift arm to its raised position as the person moves to the standing position.

6. The lift-assisted mobility device of claim 1, wherein the amount of force supplied by the constant force mechanism is reduced to contribute to the lowering of the lift arm as the person moves to the seated position.

7. The lift-assisted mobility device of claim 1, wherein the constant force mechanism comprises an air cylinder, air spring, torsion spring, or helical spring.

8. The lift-assisted mobility device of claim 1 further comprising a dampener.

9. The lift-assisted mobility device of claim 1 further comprising a pneumatic control system for regulating the operation of the constant force mechanism that operates the lift assistance device comprising a an air compressor, at least one accumulator tank pressure sensor, at least one accumulator tank pressure regulator, or an air cylinder.

10. The lift-assisted mobility device of claim 9 further comprising a boost algorithm that provides an extra counterweighting force against the lift arm during the movement of the person between the seated position and the standing position.

11. The lift-assisted mobility device of claim 1, wherein the range of travel of the lift arm between its lowered position and its raised position is at least 12 inches.

12. The lift-assisted mobility device of claim 1, wherein the range of travel of the constant force mechanism within the lift-assistance device is multiplied by a factor of at least two in producing the range of travel of the lift arm between its lowered position and its raised position.

13. The lift-assisted mobility device of claim 1, wherein the constant force mechanism of the lift-assistance device is fast-operating to provide lift assistance for the person to move from the seated position to the standing position within ten seconds or less.

14. The lift-assisted mobility device of claim 1, wherein the attachment mechanism comprises:
(a) a latch body positioned within the lift arm, the latch body having a cavity that accommodates a latch "male" fitting;
(b) the latch male fitting attached to the pressure tight suit by means of a web or strap;
(c) a locking means for maintaining the latch male fitting securely within the cavity of the latch body;
(d) wherein when the latch male fitting attached to the suit is inserted inside the cavity of the latch body, and the locking means is engaged, the pressure-tight suit is operatively connected to the lift arm to be raised or lowered as the lift arm is moved between its raised position and lowered position in response to actuation of the constant force mechanism.

15. The lift-assisted mobility device of claim 14 further comprising:
(e) a latch pivot shaft disposed inside the latch body
(f) the locking means comprising at least one latch actuator knob that is rotated around the pivot shaft of the latch body to cover the latch male fitting to lock it in place inside the cavity of the latch body.

16. The lift-assisted mobility device of claim 15, wherein the actuator knob comprises a thumb knob.

17. The lift-assisted mobility device of claim 1 further comprising a rotatable linkage disposed between the lift arm and the supportive frame, wherein a width distance between two lift arms movably attached to the supportive frame can be adjusted to accommodate the size of the person using the lift-assisted mobility device.

18. The lift-assisted mobility device of claim 17, wherein the rotatable linkage comprises a cooperating screw and nut assembly for adjusting the angle of the lift arms relative to the wheeled supportive frame.

19. The lift-assisted mobility device of claim 1, wherein the wheeled supportive frame is open along its back end to enable the mobility device to be positioned around the person seated on a chair or bed.

20. The lift-assisted mobility device of claim 1, wherein the supportive frame comprises two separate base units attached to the supportive frame adapted to be disposed on either side of the person using the walker device.

21. The lift-assisted mobility device of claim 20, wherein the two base units are rotatably attached to the supportive frame so that they can be pivoted away from each other to more easily accommodate the attachment of the person's pressure tight suit to the lift arms when the person is seated in a chair, wheelchair, or bed.

22. The lift-assisted mobility device of claim 21 further comprising a control system and an associated user interface for regulating the rotatable opening and closing the base units with respect the supportive frame.

23. The lift-assisted mobility device of claim 1, wherein the supportive frame comprises a left base section, a right base section, a left upright section attached to the left base section, a right upright section attached to the right base section, a crossbar horizontally disposed with one of its ends attached to an upper end of the left upright section, and its other end attached to an upper end of the right upright section.

24. The lift-assisted mobility device of claim 23, wherein the maximum width of the walker device is 36 inches.

25. The lift-assisted mobility device of claim 23, wherein the maximum height of the walker device is 52 inches.

26. The lift-assisted mobility device of claim 23, wherein the maximum length of the base units is 48 inches.

27. The lift-assisted mobility device of claim 23, wherein the width between the two base units is adjustable.

28. The lift-assisted mobility device of claim 1 further comprising at least one push handle attached to the wheeled supportive frame adapted to be used by an assistant to help the person move the mobility device.

29. The lift-assisted mobility device of claim 28 further comprising a horizontal track disposed on the supportive frame to enable the push handle to be positioned forwards along the supportive frame.

30. The lift-assisted mobility device of claim 29 further comprising a control system and user interface for unlocking, moving, and locking the push handles into their desired position along the horizontal track.

31. The lift-assisted mobility device further of claim 1 further comprising a plurality of wheels that pivot with respect to the supportive frame to enhance the maneuverability of the walker device.

32. The lift-assisted mobility device of claim 31, wherein the pivotable wheels comprise controllable castors.

33. The lift-assisted mobility device of claim 32, wherein the controllable castors are power-operated.

34. The lift-assisted mobility device of claim 33 further comprising means for braking the power-operated controllable castors, and setting the controllable castor states between a fixed position and a free-swivel position.

35. The lift-assisted mobility device of claim 34 further comprising a control system and a user interface for changing the operating states of the controllable castors.

36. The lift-assisted mobility device of claim 1 further comprising a seat attached to the supportive frame to enable the person to sit to rest while using the walker device.

37. The lift-assisted mobility device of claim 1, wherein the pressure-tight suit comprises a support mechanism comprised of support fabric pieces extending from the suit for connection to the attachment mechanism of the lift arm.

38. The lift-assisted mobility device of claim 37, wherein the support mechanism comprises a piece of webbing connected at its one end to the support fabric piece, and connected at its other end to a "male" fitting of the attachment mechanism.

39. The lift-assisted mobility device of claim 38, wherein the attachment mechanism comprises a latch pin connected to the end of the webbing for insertion inside a cavity formed inside a latch body positioned within the lift arm, and locking means for securely retaining the latch pin inside the cavity to releasably connect the pressure-tight suit to the lift arm of the walker device.

40. The lift-assisted mobility device of claim 37, wherein the support fabric pieces of the suit are adapted to accommodate freedom of body movement of the person during ambulation in the form of at least one of swinging of the person's legs about a medio-lateral axis through the person's hips, or leaning of the person's torso forwards and backwards about a medio-lateral axis through the person's waist.

41. The lift-assisted mobility device of claim 1, wherein the mobility device is used to provide stability to the person during the sit-to-stand movement, walking, or assist the mobility of elderly or physically impaired persons undergoing rehabilitation from injuries.

42. A method of therapy for a person having a body weight undergoing rehabilitation from injuries or providing stability to an elderly or physically impaired person comprising:
  (a) providing to the person a pressure-tight suit adapted to being worn over at least one part of the person's lower body, the suit having:
    (i) at least one opening for inserting the body part into the suit;
    (ii) means for providing a pressure-tight seal connected adjacent to the opening of the suit for operative engagement of the body part surface of the person;
    (iii) inlet means in the suit for introduction of at least one source of positive pressure or vacuum to an interior of the suit between the person's body and the suit to create a differential pressure condition therein between the positive pressure or vacuum condition inside the suit, and a pressure condition existing outside the suit;
  (b) providing a lift-assisted mobility device comprising:
    (i) a wheeled supportive frame upon which the person may lean while walking or running;
    (ii) a lift-assistance device having a constant force mechanism attached to the supportive frame with a linkage connected thereto;
    (iii) at least one lift arm operatively connected to the linkage for movement between a lowered position and a raised position;
    (iv) an attachment mechanism connected to the lift arm providing a detachable connection to the suit;
  (c) supplying the at least one source of positive pressure or vacuum to the interior of the suit;
  (d) actuation of the constant force mechanism;
  (e) wherein the differential pressure condition is adapted to exert an upwards force upon the body part to offload a desired portion of the weight of the body to the lift-assistance device and the supportive frame with the supportive frame counteracting a downwards force applied to the suit when it is placed under the differential pressure condition; and
  (f) wherein the actuated constant force mechanism raises the lift arm via the linkage from the lowered position to the raised position to lift the suit vertically as the person rises from the seated position to the standing position, whereupon the person may stand easily with reduced effort aided by the reduced body weight, and move about with body weight support.

43. A method of therapy for a person having a body weight undergoing rehabilitation from injuries or providing stability to an elderly or physically impaired person comprising:
  (a) providing to the person a pressure-tight suit adapted to being worn over at least one part of the person's lower body, the suit having:
    (i) at least one opening for inserting the body part into the suit;
    (ii) means for providing a pressure-tight seal connected adjacent to the opening of the suit for operative engagement of the body part surface of the person;
    (iii) inlet means in the suit for introduction of at least one source of positive pressure or vacuum to an interior of the suit between the person's body and the suit to create a differential pressure condition therein between the positive pressure or vacuum condition inside the suit, and a pressure condition existing outside the suit;
  (b) providing an assisted mobility device comprising:

(i) a wheeled supportive frame, the supportive frame having a forward section and two base sections pivotably attached to the forward section;
(ii) an attachment mechanism connected to the supportive frame providing a detachable connection to the suit;
(c) supplying the at least one source of positive pressure or vacuum to the interior of the suit;
(d) pivoting at least one of the base sections outwards with respect to the forward section of the supportive frame to widen the distance between the two base sections;
(e) wherein the differential pressure condition is adapted to exert an upwards force upon the body part to offload a desired portion of the weight of the body to the lift-assistance device and the supportive frame with the supportive frame counteracting a downwards force applied to the suit when it is placed under the differential pressure condition to assist the motion of the person ambulating laterally with respect to the mobility device with the widened distance between the base sections providing more freedom of leg movement to the person.

* * * * *